United States Patent
Boral et al.

(10) Patent No.: US 9,371,314 B2
(45) Date of Patent: Jun. 21, 2016

(54) PYRIDYL BENZOTHIOPHENES AS KINASE INHIBITORS

(71) Applicant: Allergan, Inc., Irvine, CA (US)

(72) Inventors: Sougato Boral, Irvine, CA (US);
Thomas C. Malone, Irvine, CA (US);
Shimiao Wang, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/511,112

(22) Filed: Oct. 9, 2014

(65) Prior Publication Data

US 2016/0102080 A1    Apr. 14, 2016

(51) Int. Cl.
| | |
|---|---|
| C07D 409/04 | (2006.01) |
| C07F 5/02 | (2006.01) |
| C07D 409/14 | (2006.01) |
| C07D 213/81 | (2006.01) |
| C07F 9/58 | (2006.01) |
| C07D 213/79 | (2006.01) |

(52) U.S. Cl.
CPC ............ *C07D 409/04* (2013.01); *C07D 213/79* (2013.01); *C07D 213/81* (2013.01); *C07D 409/14* (2013.01); *C07F 5/02* (2013.01); *C07F 5/025* (2013.01); *C07F 9/587* (2013.01)

(58) Field of Classification Search
CPC ................................. C07D 409/04; C07F 5/02
USPC ............................ 546/13, 281.1; 514/64, 337
See application file for complete search history.

(56) References Cited

U.S. PATENT DOCUMENTS

| | | | |
|---|---|---|---|
| 8,501,713 | B2 | 8/2013 | Wynne et al. |
| 8,518,980 | B2 | 8/2013 | Wynne et al. |
| 8,642,660 | B2 | 2/2014 | Goldfarb |
| 2009/0163545 | A1 | 6/2009 | Goldfarb |
| 2011/0166132 | A1 | 7/2011 | Hitchcock et al. |
| 2011/0195932 | A1 | 8/2011 | Wynne et al. |

FOREIGN PATENT DOCUMENTS

| | | |
|---|---|---|
| KR | 2011033395 A | 3/2011 |
| WO | 99-62890 | 12/1999 |
| WO | 2005-082001 | 9/2005 |
| WO | 2006-026034 | 3/2006 |
| WO | 2007-091106 | 8/2007 |
| WO | 2009-019504 | 2/2009 |
| WO | 2009-075874 | 6/2009 |

OTHER PUBLICATIONS

Binder et al., "Preparation of, etc.," CA 123:313993 (1995).*
Nobuo Jo, Carolina Mailhos, et al., Inhibition of Platelet-Derived Growth Factor B Signaling Enhances the Efficacy of Anti-Vascular Endothelial Growth Factor Therapy in Multiple Models of Ocular Neovascularization, American Journal of Pathology, vol. 168, No. 6, Jun. 2006.

Justine R Smith, et al., Expression of vascular endothelial growth factor and its receptors in rosacea, Br J Ophthalmol 2007;91:226-229. doi: 10.1136/bjo.2006.101121.
S. W. Cowan-Jacob, et al., Structural biology of protein tyrosine kinases, Cell. Mol. Life Sci. 63 (2006) 2608-2625.
Regina Heidenreich, et al., Angiogenesis: The New Potential Target for the Therapy of Psoriasis?Drug News Perspect 21(2), Mar. 2008.
Aimee V. Chappelow et al., Neovascular Age-Related Macular Degeneration, Potential Therapies, Drugs 2008; 68 (8): 1029-1036.
Mark Rami Barakat, et al., VEGF inhibitors for the treatment of neovascular age-related macular degeneration, Expert Opin. Investig. Drugs (2009) 18(5).
Xinyuan Zhang, et al., Vascular endothelial growth factor-A: A multifunctional molecular player in diabetic retinopathy, The International Journal of Biochemistry & Cell Biology 41 (2009) 2368-2371.
Zhang Ni, et al., Emerging Pharmacologic Therapies for Wet Age-Related Macular Degeneration, Ophthalmologica 2009;223:401-410.
Jayne M. Stommel et al., Coactivation of Receptor Tyrosine Kinases Affects the Response of Tumor Cells to Targeted Therapies, www.sciencemag.org, Science vol. 318 Oct. 12, 2007.
Akulapalli Sudhakar et al., Phosphorylation of Serine 51 in Initiation Factor 2α (eIF2α) Promotes Complex Formation between eIF2α(P) and eIF2B and Causes Inhibition in the Guanine Nucleotide Exchange Activity of eIF2B†, Biochemistry 2000, 39, 12929-12938.
Madhusudan Dey et al., Mechanistic Link between PKR Dimerization, Autophosphorylation, and eIF2α Substrate Recognition, Cell, vol. 122, 901-913, Sep. 23, 2005.
Neysan Donnelly et al., The eIF2α kinases: their structures and functions, Cell. Mol. Life Sci. (2013) 70:3493-3511.
Qiaozhu Su et al., Interferons induce tyrosine phosphorylation of the eIF2α kinase PKR through activation of Jak1 and Tyk2, EMBO reports vol. 8, No. 3, 2007.
Masamitsu Shimazawa et al., Involvement of Double-Stranded RNA-Dependent Protein Kinase in ER Stress-Induced Retinal Neuron Damage, IOVS, Aug. 2007, vol. 48, No. 8.
Silva et al., Protein Kinase R (PKR) Interacts with and Activates Mitogen-activated Protein Kinase Kinase 6 (MKK6) in Response to Double-stranded RNA Stimulation, J. Biol. Chem. 2004, 279:37670-37676.
Howard C.H. Yim et al., Protein Kinase R and the Inflammasome, Journal of Interferon & Cytokine Research, vol. 34, No. 6, 2014.
Matthew Campbell et al., An eye on the future of inflammasomes and drug development in AMD, J Mol Med (2013) 91:1059-1070.
M. A. Garcia et al., Impact of Protein Kinase PKR in Cell Biology: from Antiviral to Antiproliferative Action, Microbiol. Mol. Biol. Rev. 2006, 70(4):1032.
Ben Lu et al., Novel role of PKR in inflammasome activation and HMGB1 release, Nature. Aug. 30, 2012; 488 (7413): 670-674, www.nature.com/nature.

(Continued)

Primary Examiner — Patricia L Morris
(74) Attorney, Agent, or Firm — Jonathan Bass

(57) ABSTRACT

This invention is directed to compounds, which are useful as protein kinase (PK) inhibitors and can be used to treat such diseases as cancer, blood vessel proliferative disorders, fibrotic disorders, mesangial cell proliferative disorders, metabolic diseases inflammatory disorders and neurodegenerative disorders.

18 Claims, No Drawings

(56) References Cited

OTHER PUBLICATIONS

Siddharth Balachandran et al., Activation of the dsRNA-dependent protein kinase, PKR, induces apoptosis through FADD-mediated death signaling, The EMBO Journal vol. 17 No. 23 pp. 6888-6902, 1998.

Goh et al., The protein kinase PKR is required for p38 MAPK activation and the innate immune response to bacterial endotoxin, The EMBO Journal vol. 19 No. 16 pp. 4292-4297, 2000.

Arora, Amit et al., Role of Tyrosine Kinase Inhibitors in Cancer Therapy, The Journal of Pharmacology and Experimental Therapeutics 2005, 315: 971-979.

Bergers, Gabriele et al., Benefits of targeting both pericytes and endothelial cells in the tumor vasculature with kinase inhibitors, The Journal of Clinical Investigation 2003, 111: 1287-1295 (9).

Cross, L.C. et al., Rules for the Nomenclature of Organic Chemistry Section E: Stereochemistry, Pure & Appl. Chem. 1976, 45: 11-30.

Stahl, Heinrich et al., Handbook of Pharmaceutical Salts, Properties, Selection, and Use, Zurich, Switzerland 2002, pp. 329-345.

* cited by examiner

PYRIDYL BENZOTHIOPHENES AS KINASE INHIBITORS

FIELD OF THE INVENTION

The invention relates to inhibitors of VEGFR2 kinase or VEGFR, PDGFR kinases or PDGFR and Protein Kinase R (EIF2AK2), and methods of using such compounds. The present invention is also directed to methods of regulating, modulating or inhibiting protein kinases, whether of the receptor or non-receptor class, for the prevention and/or treatment of disorders related to unregulated protein kinase signal transduction, including cell growth, metabolic, and blood vessel proliferative disorders.

DESCRIPTION OF THE RELATED ART

Protein kinases (PKs) comprise a large and diverse class of proteins having enzymatic activity which catalyzes the transfer of the terminal phosphate of ATP to the hydroxyl group of a serine, threonine or tyrosine group in a protein. Protein kinases (PKs) are involved in numerous diseases which result from dysregulation of their normal function.

There are numerous examples where protein kinases, have been found to be involved in cellular signaling pathways leading to pathological conditions. In the VEGFR2 kinase protein kinase, which is a receptor tyrosine kinase, pathological conditions involving aberrant angiogenesis include cancer, wet age-related macular degeneration (Ni et al. Opthalmologica 2009 223 401-410; Chappelow et al. Drugs 2008 68 1029-1036), diabetic retinopathy (Zhang et al Int. J. Biochem. Cell Biol. 2009 41 2368-2371), cancer (Aora et al. J. Path. Exp. Ther. 2006, 315, 971), psoriasis (Heidenreich et al Drug News Perspective 2008 21 97-105) and hyper immune response. In ophthalmic diseases such as neovascular age-related macular degeneration and diabetic retinopathy aberrant activation of VEGF receptors can lead to abnormal blood vessel growth. The importance of VEGFR signaling in the neovascular age-related macular degeneration disease process is evident by the clinical success of multiple anti-VEGF targeting agents including Lucentis®, Avastin®, and EYLEA™ (Barakat et al. Expert Opin. Investig. Drugs 2009, 18, 637). Recently it has been suggested that inhibition of multiple protein kinase signaling pathways may provide a greater therapeutic effect than targeting a single signaling pathway. For example in neovascular ocular disorders such as neovascular age-related macular degeneration and diabetic retinopathy the inhibition of both VEGFR and PDGFRβ may provide a greater therapeutic effect in by causing regression of existing neovascular blood vessels present in the disease (Adamis et al. Am. J. Pathol. 2006 168 2036-2053). In cancer inhibition of multiple PK signaling pathways has been suggested to have a greater effect than inhibiting a single PK pathway (DePinho et al. Science 2007 318 287-290; Bergers et al. J. Clin Invest. 2003 111 1287-1295).

It has also been suggested that misregulated protein kinases are involved in neurodegenerative disease. In particular Protein Kinase R has been implicated in neurodegenerative disease. Protein Kinase R (PKR, also known as interferon-induced, double-stranded RNA-activated protein kinase, or eukaryotic translation initiation factor 2-alpha kinase 2) is one of four known mammalian kinases that phosphorylate eukaryotic translation initiation factor 2-alpha (eIF-2α) in response to a variety of stress conditions (Donnelly et al., Cell. Mol. Life Sci. 2013, 70, 3493-3511). PKR plays a central role in the innate immune system and serves to prevent viral replication and viral infection (for a detailed review see Garcia et al., Microbiol. and Mol. Bio. Rev. 2006, 70, 1032-1060). It is proposed that in chronic conditions like AMD, innate immune players respond to modified host derived elements (ROS/Alu) and external particulate matter (drusen) by activation of inflammasome complex. Emerging evidence indicates that PKR has a key role in NLRP3 inflammasome activation (Yim & Williams; J of Interferon & Cytokine Res, 2014, Campbell & Doyle, J Mol Med, 2013, Lu et.al; Nature, 2012).

The binding of double stranded RNA to the double stranded RNA regulatory domains of PKR induces dimerization and autophosphorylation which leads to activation of the kinase (Dever et al., Cell 2005, 122, 901-913). Once activated by dimerization PKR can suppress protein synthesis by phosphorylation of serine-51 on eukaryotic translation initiation factor 2-alpha (eIF-2α). In its phosphorylated form eIF2alpha increases its affinity for eIF-2B by 100-fold effectively converting it into a competitive inhibitor of eIF-2B. By this mechanism a small amount of phosphorylated eIF2alpha can effectively inhibit the guanine nucleotide exchange activity of eIF-2B and shut down protein translation (Ramaiah et al., Biochemistry 2000, 39, 12929-12938).

In addition to PKR's role in regulation of protein synthesis it also plays an important role in signal transduction linked to apoptotic cell death. PKR has been shown to be activated by dsRNA, number of growth factors and cytokines including INF, PDGF, TNF-alpha, and IL-1 and by the activation of Toll receptors. PKR has also been shown to be phosphorylated by JAK1 and Tyk2 kinases (Su et al., EMBO Reports 2007, 3, 265). Activation of PKR leads to the activation of multiple signaling pathways that are involved in inflammation and cell death. PKR is required for phosphorylation of MKK6 (Williams et al., J. Biol. Chem. 2004, 279, 37670-37676) and subsequent p38 MAPK signaling (Williams et al., The EMBO Journal 2000, 19, 4292-4297). PKR induces the expression of the pro apoptotic factor CHOP and has been shown to induce apoptosis by the FADD/Caspase 8 pathway (Barber, G. et al, The EMBO Journal 1998, 17, 6888-6902).

Due to its key role in regulation of apoptotic cell death PKR inhibition may be useful in prevention of the rod and cone photoreceptor cell death and ganglion cell death associated with the atrophic form of macular degeneration (Shimazawa et al, IVOS 2007, 48, 3729-3736).

The identification of effective small compounds which specifically inhibit signal transduction by modulating the activity of receptor and non-receptor protein kinases to regulate and modulate abnormal or inappropriate cell proliferation is therefore desirable and one object of this invention.

Certain small compounds are disclosed in PCT publication No. WO/1999/062890, PCT publication No. WO/2005/082001 and PCT publication No. WO/2006/026034 as useful for the treatment of diseases related to unregulated TKS transduction. These patents disclose starting materials and methods for the preparation thereof, screens and assays to determine a claimed compound's ability to modulate, regulate and/or inhibit cell proliferation, indications which are treatable with said compounds, formulations and routes of administration, effective dosages, etc.

US2009/0163545 refers to methods of using lifespan-altering compounds for altering the lifespan of eukaryotic organisms and screening for such compounds.

WO2009/019504 refers to the preparation of benzoxazoles, benzimidazoles, indoles and their analogs for the treatment of muscular dystrophy and cachexia.

WO2007/091106 refers to the preparation of benzoxazoles, benzimidazoles, indoles and their analogs for the treatment of muscular dystrophy and cachexia.

KR 2011033395 refers to the preparation of benzoxazolyl-pyridine derivatives as protein kinase inhibitors.
WO2009/075874 refers to the preparation of N-[4-pyridin-4-yl)phenyl]amides as gamma-secretase modulators.

SUMMARY OF THE INVENTION

The present invention relates to organic molecules capable of modulating, regulating and/or inhibiting protein kinase signal transduction, useful for treating diseases related to protein kinase signal transduction, for example, cancer, blood vessel proliferative disorders, fibrotic disorders, and neurodegenerative diseases. In particular, the compounds of the present invention are useful for treatment of mesangial cell proliferative disorders and metabolic diseases, lung carcinomas, breast carcinomas, Non Hodgkin's lymphomas, ovarian carcinoma, pancreatic cancer, malignant pleural mesothelioma, melanoma, arthritis, restenosis, hepatic cirrhosis, atherosclerosis, psoriasis, rosacea, diabetic mellitus, wound healing, inflammation and neurodegenerative diseases and preferably ophthalmic diseases, i.e. diabetic retinopathy, retinopathy of prematurity, macular edema, retinal vein occlusion, exudative or neovascular age-related macular degeneration, high-risk eyes (i.e. fellow eyes have neovascular age-related macular degeneration) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, atrophic macular degeneration, geographic atrophy, central serous retinopathy, cystoid macular edema, diabetic retinopathy, proliferative diabetic retinopathy, diabetic macular edema, rubeosis iridis, retinopathy of prematurity, Central and branch retinal vein occlusions, inflammatory/infectious retinal, neovascularization/edema, corneal neovascularization, hyperemia related to an actively inflamed pterygia, recurrent pterygia following excisional surgery, post-excision, progressive pterygia approaching the visual axis, prophylactic therapy to prevent recurrent pterygia, of post-excision, progressive pterygia approaching the visual axis, chronic low grade hyperemia associated with pterygia, neovascular glaucoma, iris neovascularization, idiopathic etiologies, presumed ocular histoplasmosis syndrome, retinopathy of prematurity, chronic allergic conjunctivitis, ocular rosacea, blepharoconjunctivitis, recurrent episcleritis, keratoconjunctivitis sicca, ocular graft vs host disease, etc.

In one aspect, the invention provides a compound represented by Formula I or a pharmaceutically acceptable salt thereof or stereoisomeric forms thereof, or the enantiomers, diastereoisomers, tautomers, zwitterions and pharmaceutically acceptable salts thereof:

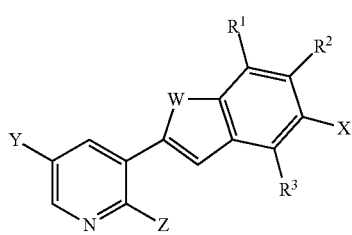

Formula I wherein:
W is O, S, N(CO)$R^{14}$, $CF_2$, $C(CH_3)_2$, N(CO)(NH)$R^{14}$ or N$R^{14}$;
$R^1$ is hydrogen, substituted or unsubstituted $C_{1-8}$ alkyl, halo or haloalkyl;
$R^2$ is —N($R^4$)C(O)N($R^4R^5$), —N($R^4$)C(O)$R^5$, —C(O)N($R^4R^5$), hydrogen, substituted or unsubstituted $C_{1-8}$ alkyl, halo or haloalkyl;
$R^3$ is hydrogen, substituted or unsubstituted $C_{1-8}$ alkyl, halo or haloalkyl;
X is —N($R^4$)C(O)N($R^4R^5$), —N($R^4$)C(O)$R^5$, —C(O)N($R^4R^5$), hydrogen, substituted or unsubstituted $C_{1-8}$ alkyl, halo or haloalkyl;
$R^4$ is hydrogen or substituted or unsubstituted alkyl;
$R^5$ is substituted or unsubstituted alkyl, substituted or unsubstituted heterocycle or substituted or unsubstituted aryl;
Y is hydrogen, —C(O)—N=S(O)$R^7R^6$, —N($R^4$)C(O)$R^8$, —OCO$R^9$, —C(O)NH$R^{10}$, —B(OH)$_2$, —B(O$R^{12}$)(O$R^{13}$) or

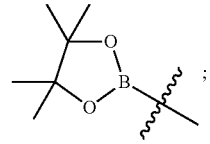 [SMILES: *B1OC(C)(C)C(C)(C)O1]

$R^7$ is substituted or unsubstituted $C_{1-8}$ alkyl, substituted or unsubstituted heterocycle or substituted or unsubstituted aryl;
$R^6$ is substituted or unsubstituted $C_{1-8}$ alkyl, substituted or unsubstituted heterocycle or substituted or unsubstituted aryl;
$R^8$ is substituted or unsubstituted $C_{1-8}$ alkyl, substituted or unsubstituted heterocycle or substituted or unsubstituted aryl;
$R^9$ is hydrogen, substituted or unsubstituted $C_{1-8}$ alkyl, substituted or unsubstituted heterocycle or substituted or unsubstituted aryl;
$R^{10}$ is hydrogen, substituted or unsubstituted $C_{1-8}$ alkyl, substituted or unsubstituted heterocycle or substituted or unsubstituted aryl;
Z is —NH$R^{11}$;
$R^{11}$ is hydrogen or substituted or unsubstituted $C_{1-8}$ alkyl;
$R^{12}$ is hydrogen or substituted or unsubstituted $C_{1-8}$ alkyl;
$R^{13}$ is hydrogen or substituted or unsubstituted $C_{1-8}$ alkyl;
$R^{14}$ is hydrogen or substituted or unsubstituted $C_{1-8}$ alkyl;
and
with the proviso that the compound of Formula I is not

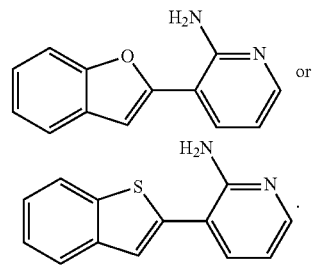

In another aspect, the invention provides a compound represented by Formula I wherein:
W is O, S, N(CO)$R^{14}$, $CF_2$, $C(CH_3)_2$, N(CO)(NH)$R^{14}$ or N$R^{14}$;
$R^1$ is hydrogen;
$R^2$ is hydrogen;
$R^3$ is hydrogen;
X is —N($R^4$)C(O)N($R^4R^5$), —N($R^4$)C(O)$R^5$, or —C(O)N($R^4R^5$);

$R^4$ is hydrogen or substituted or unsubstituted alkyl;
$R^5$ is substituted or unsubstituted alkyl, substituted or unsubstituted heterocycle or substituted or unsubstituted aryl;
Y is hydrogen, —C(O)—N=S(O)$R^7R^6$, —COOR$^9$, —C(O)NHR$^{10}$, —B(OH)$_2$, or

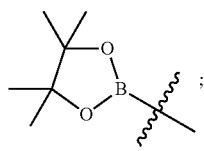 [SMILES: *B1OC(C)(C)C(C)(C)O1]

$R^7$ is substituted or unsubstituted C$_{1-8}$ alkyl;
$R^6$ is substituted or unsubstituted C$_{1-8}$ alkyl;
$R^9$ is hydrogen or substituted or unsubstituted C$_{1-8}$ alkyl;
$R^{10}$ is hydrogen or substituted or unsubstituted C$_{1-8}$ alkyl;
Z is —NHR$^{11}$; and
$R^{11}$ is hydrogen or substituted or unsubstituted C$_{1-8}$ alkyl;
$R^{14}$ is hydrogen or substituted or unsubstituted C$_{1-8}$ alkyl; and
with the proviso that the compound of Formula I is not

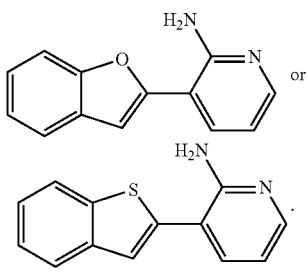

In another aspect, the invention provides a compound represented by Formula I wherein:
W is S;
$R^1$ is hydrogen;
$R^2$ is hydrogen;
$R^3$ is hydrogen;
X is —N(R$^4$)C(O)N(R$^4R^5$);
$R^4$ is hydrogen or substituted or unsubstituted alkyl;
$R^5$ is substituted or unsubstituted alkyl, substituted or unsubstituted heterocycle or substituted or unsubstituted aryl;
Y is hydrogen, —C(O)—N=S(O)$R^7R^6$, —COOR$^9$, —C(O)NHR$^{10}$, —B(OH)$_2$, or

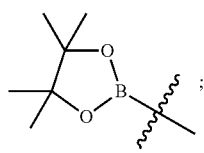 [SMILES: *B1OC(C)(C)C(C)(C)O1]

$R^7$ is substituted or unsubstituted C$_{1-8}$ alkyl;
$R^6$ is substituted or unsubstituted C$_{1-8}$ alkyl;
$R^9$ is hydrogen or substituted or unsubstituted C$_{1-8}$ alkyl;
$R^{10}$ is hydrogen or substituted or unsubstituted C$_{1-8}$ alkyl;
Z is —NHR$^{11}$; and
$R^{11}$ is hydrogen or substituted or unsubstituted C$_{1-8}$ alkyl.
In another aspect, the invention provides a compound represented by Formula I wherein:
W is S;
$R^1$ is hydrogen;
$R^2$ is hydrogen;
$R^3$ is hydrogen;
X is —N(R$^4$)C(O)N(R$^4R^5$);
$R^4$ is hydrogen or substituted or unsubstituted alkyl;
$R^5$ is substituted or unsubstituted alkyl, substituted or unsubstituted heterocycle or substituted or unsubstituted aryl;
Y is —C(O)—N=S(O)$R^7R^6$,
$R^7$ is substituted or unsubstituted C$_{1-8}$ alkyl;
$R^6$ is substituted or unsubstituted C$_{1-8}$ alkyl;
Z is —NHR$^{11}$; and
$R^{11}$ is hydrogen or substituted or unsubstituted C$_{1-8}$ alkyl.
In another aspect, the invention provides a compound represented by Formula I wherein:
W is S;
$R^1$ is hydrogen;
$R^2$ is hydrogen;
$R^3$ is hydrogen;
X is —N(R$^4$)C(O)N(R$^4R^5$);
$R^4$ is hydrogen or substituted or unsubstituted alkyl;
$R^5$ is substituted or unsubstituted alkyl, substituted or unsubstituted heterocycle or substituted or unsubstituted aryl;
Y is —C(O)—N=S(O)$R^7R^6$,
$R^7$ is substituted or unsubstituted C$_{1-8}$ alkyl;
$R^6$ is substituted or unsubstituted C$_{1-8}$ alkyl;
Z is —NHR$^{11}$; and
$R^{11}$ is hydrogen.
In another aspect, the invention provides a compound represented by Formula I wherein:
W is S;
$R^1$ is hydrogen;
$R^2$ is hydrogen;
$R^3$ is hydrogen;
X is —N(R$^4$)C(O)N(R$^4R^5$);
$R^4$ is hydrogen;
$R^5$ is substituted or unsubstituted alkyl, substituted or unsubstituted heterocycle or substituted or unsubstituted aryl;
Y is —C(O)—N=S(O)$R^7R^6$,
$R^7$ is substituted or unsubstituted C$_{1-8}$ alkyl;
$R^6$ is substituted or unsubstituted C$_{1-8}$ alkyl;
Z is —NHR$^{11}$; and
$R^{11}$ is hydrogen or substituted or unsubstituted C$_{1-8}$ alkyl.
In another aspect, the invention provides a compound represented by Formula I wherein:
W is S;
$R^1$ is hydrogen;
$R^2$ is hydrogen;
$R^3$ is hydrogen;
X is —N(R$^4$)C(O)N(R$^4R^5$);
$R^4$ is hydrogen;
$R^5$ is substituted or unsubstituted aryl;
Y is —C(O)—N=S(O)$R^7R^6$,
$R^7$ is substituted or unsubstituted C$_{1-8}$ alkyl;
$R^6$ is substituted or unsubstituted C$_{1-8}$ alkyl;
Z is —NHR$^{11}$; and
$R^{11}$ is hydrogen or substituted or unsubstituted C$_{1-8}$ alkyl.
In another aspect, the invention provides a compound represented by Formula I wherein:
W is S;
$R^1$ is hydrogen;
$R^2$ is hydrogen;
$R^3$ is hydrogen;
X is —N(R$^4$)C(O)N(R$^4R^5$);
$R^4$ is hydrogen;
$R^5$ is substituted or unsubstituted heterocycle;
Y is —C(O)—N=S(O)$R^7R^6$,
$R^7$ is substituted or unsubstituted C$_{1-8}$ alkyl;
$R^6$ is substituted or unsubstituted C$_{1-8}$ alkyl;

Z is —NHR$^{11}$; and
R$^{11}$ is hydrogen or substituted or unsubstituted C$_{1-8}$ alkyl.
In another aspect, the invention provides a compound represented by Formula I wherein:
W is S;
R$^1$ is hydrogen;
R$^2$ is hydrogen;
R$^3$ is hydrogen;
X is —N(R$^4$)C(O)R$^5$;
R$^4$ is hydrogen;
R$^5$ is substituted or unsubstituted heterocycle or substituted or unsubstituted aryl;
Y is hydrogen, —C(O)—N=S(O)R$^7$R$^6$, —COOR$^9$, —C(O)NHR$^{10}$, —B(OH)$_2$, or

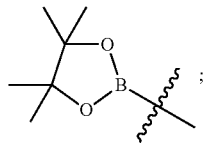 [SMILES: *B1OC(C)(C)C(C)(C)O1]

R$^7$ is substituted or unsubstituted C$_{1-8}$ alkyl;
R$^6$ is substituted or unsubstituted C$_{1-8}$ alkyl;
R$^9$ is hydrogen or substituted or unsubstituted C$_{1-8}$ alkyl;
R$^{10}$ is hydrogen or substituted or unsubstituted C$_{1-8}$ alkyl;
Z is —NHR$^{11}$; and
R$^{11}$ is hydrogen or substituted or unsubstituted C$_{1-8}$ alkyl.
In another aspect, the invention provides a compound represented by Formula I wherein:
W is S;
R$^1$ is hydrogen;
R$^2$ is hydrogen;
R$^3$ is hydrogen;
X is —N(R$^4$)C(O)R$^5$;
R$^4$ is hydrogen;
R$^5$ is substituted or unsubstituted aryl;
Y is hydrogen, —C(O)—N=S(O)R$^7$R$^6$, —COOR$^9$, —C(O)NHR$^{10}$, —B(OH)$_2$, or

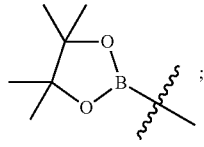 [SMILES: *B1OC(C)(C)C(C)(C)O1]

R$^7$ is substituted or unsubstituted C$_{1-8}$ alkyl;
R$^6$ is substituted or unsubstituted C$_{1-8}$ alkyl;
R$^9$ is hydrogen or substituted or unsubstituted C$_{1-8}$ alkyl;
R$^{10}$ is hydrogen or substituted or unsubstituted C$_{1-8}$ alkyl;
Z is —NHR$^{11}$; and
R$^{11}$ is hydrogen or substituted or unsubstituted C$_{1-8}$ alkyl.
In another aspect, the invention provides a compound represented by Formula I wherein:
W is S;
R$^1$ is hydrogen;
R$^2$ is hydrogen;
R$^3$ is hydrogen;
X is —C(O)N(R$^4$R$^5$);
R$^4$ is hydrogen;
R$^5$ is substituted or unsubstituted aryl;
Y is —COOR$^9$;
R$^7$ is substituted or unsubstituted C$_{1-8}$ alkyl, substituted or unsubstituted heterocycle or substituted or unsubstituted aryl;
R$^6$ is substituted or unsubstituted C$_{1-8}$ alkyl, substituted or unsubstituted heterocycle or substituted or unsubstituted aryl;
R$^9$ is hydrogen or substituted or unsubstituted C$_{1-8}$ alkyl;
Z is —NHR$^{11}$; and
R$^{11}$ is hydrogen or substituted or unsubstituted C$_{1-8}$ alkyl.
In another aspect, the invention provides a compound represented by Formula I wherein:
W is S;
R$^1$ is hydrogen;
R$^2$ is hydrogen;
R$^3$ is hydrogen;
X is —N(R$^4$)C(O)N(R$^4$R$^5$);
R$^4$ is hydrogen;
R$^5$ is substituted or unsubstituted aryl;
Y is —C(O)NHR$^{10}$;
R$^{10}$ is hydrogen or substituted or unsubstituted C$_{1-8}$ alkyl;
Z is —NHR$^{11}$; and
R$^{11}$ is hydrogen or substituted or unsubstituted C$_{1-8}$ alkyl.
In another aspect, the invention provides a compound represented by Formula I wherein:
W is S;
R$^1$ is hydrogen;
R$^2$ is hydrogen;
R$^3$ is hydrogen;
X is —N(R$^4$)C(O)N(R$^4$R$^5$);
R$^4$ is hydrogen;
R$^5$ is substituted or unsubstituted aryl;
Y is

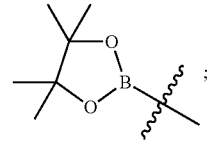 [SMILES: *B1OC(C)(C)C(C)(C)O1]

Z is —NHR$^{11}$; and
R$^{11}$ is hydrogen or substituted or unsubstituted C$_{1-8}$ alkyl.
In another aspect, the invention provides a compound represented by Formula I wherein:
W is S;
R$^1$ is hydrogen;
R$^2$ is hydrogen;
R$^3$ is hydrogen;
X is —N(R$^4$)C(O)N(R$^4$R$^5$);
R$^4$ is hydrogen;
R$^5$ is substituted or unsubstituted aryl;
Y is —B(OH)$_2$;
Z is —NHR$^{11}$; and
R$^{11}$ is hydrogen or substituted or unsubstituted C$_{1-8}$ alkyl.
In another aspect, the invention provides a compound represented by Formula I wherein:
W is S;
R$^1$ is hydrogen;
R$^2$ is hydrogen;
R$^3$ is hydrogen;
X is —N(R$^4$)C(O)R$^5$;
R$^4$ is hydrogen;
R$^5$ is substituted or unsubstituted aryl;
Y is hydrogen;
Z is —NHR$^{11}$; and
R$^{11}$ is hydrogen or substituted or unsubstituted C$_{1-8}$ alkyl.
In another aspect, the invention provides a compound represented by Formula I wherein:
W is S;
R$^1$ is hydrogen;

$R^2$ is hydrogen;
$R^3$ is hydrogen;
X is —C(O)N($R^4R^5$);
$R^4$ is hydrogen or substituted or unsubstituted alkyl;
$R^5$ is substituted or unsubstituted alkyl or substituted or unsubstituted heterocycle or substituted or unsubstituted aryl;
Y is hydrogen;
Z is —NH$R^{11}$; and
$R^{11}$ is hydrogen or substituted or unsubstituted $C_{1-8}$ alkyl.

In one aspect, the invention provides a compound represented by Formula II or a pharmaceutically acceptable salt thereof or stereoisomeric forms thereof, or the enantiomers, diastereoisomers, tautomers, zwitterions and pharmaceutically acceptable salts thereof:

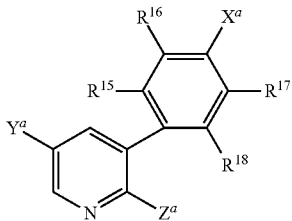

Formula II wherein:
$R^{15}$ is hydrogen, substituted or unsubstituted $C_{1-8}$ alkyl, halo or haloalkyl;
$R^{16}$ is hydrogen, substituted or unsubstituted $C_{1-8}$ alkyl, halo or haloalkyl;
$R^{17}$ is hydrogen, substituted or unsubstituted $C_{1-8}$ alkyl, halo or haloalkyl;
$X^a$ is —N($R^{19}$)C(O)N($R^{19}R^{20}$);
$R^{18}$ is hydrogen, substituted or unsubstituted $C_{1-8}$ alkyl, halo or haloalkyl;
$R^{19}$ is hydrogen, substituted or unsubstituted $C_{1-8}$ alkyl, substituted or unsubstituted heterocycle or substituted or unsubstituted aryl;
$R^{20}$ is substituted or unsubstituted alkyl, substituted or unsubstituted heterocycle or substituted or unsubstituted aryl;
$Y^a$ is hydrogen, —C(O)—N=S(O)$R^{21}R^{22}$, —N($R^{23}$)C(O)$R^{24}$, —COO$R^{25}$, —C(O)NH$R^{27}$, —B(OH)$_2$, —B(O$R^{28}$)(O$R^{29}$) or

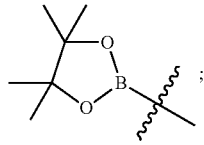 [SMILES: *B1OC(C)(C)C(C)(C)O1]

$R^{21}$ is substituted or unsubstituted $C_{1-8}$ alkyl, substituted or unsubstituted heterocycle or substituted or unsubstituted aryl;
$R^{22}$ is substituted or unsubstituted $C_{1-8}$ alkyl, substituted or unsubstituted heterocycle or substituted or unsubstituted aryl;
$R^{23}$ is substituted or unsubstituted $C_{1-8}$ alkyl, substituted or unsubstituted heterocycle or substituted or unsubstituted aryl;
$R^{24}$ is hydrogen, substituted or unsubstituted $C_{1-8}$ alkyl, substituted or unsubstituted heterocycle or substituted or unsubstituted aryl;
$Z^a$ is —NH$R^{26}$;
$R^{25}$ is hydrogen or substituted or unsubstituted $C_{1-8}$ alkyl;
$R^{26}$ is hydrogen or substituted or unsubstituted $C_{1-8}$ alkyl;
$R^{27}$ is hydrogen or substituted or unsubstituted $C_{1-8}$ alkyl;
$R^{28}$ is hydrogen or substituted or unsubstituted $C_{1-8}$ alkyl; and
$R^{29}$ is hydrogen or substituted or unsubstituted $C_{1-8}$ alkyl.

The term "alkyl", as used herein, refers to saturated, monovalent or divalent hydrocarbon moieties having linear or branched moieties or combinations thereof and containing 1 to 12 carbon atoms. One methylene (—CH$_2$—) group, of the alkyl group can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can have one or more chiral centers. Alkyl groups can be independently substituted by halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups, ester groups, ketone groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen atoms, sulfonyl $C_{1-8}$ alkyl groups, sulfoxide $C_{1-8}$ alkyl groups, sulfonamide groups, nitro groups, cyano groups, —O$C_{1-8}$ alkyl groups, —S$C_{1-8}$ alkyl groups, —$C_{1-8}$ alkyl groups, —$C_{2-6}$ alkenyl groups, —$C_{2-6}$ alkynyl groups, ketone groups, alkylamino groups, amino groups, aryl groups, Cm cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen atoms, sulfonyl groups, sulfoxide groups, nitro groups, cyano groups, —O$C_{1-6}$ alkyl groups, —S$C_{1-6}$ alkyl groups, —$C_{1-6}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. One methylene (—CH$_2$—) group, of the alkenyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. $C_{2-6}$ alkenyl can be in the E or Z configuration. Alkenyl groups can be substituted by alkyl groups, as defined above or by halogen atoms.

The term "alkynyl", as used herein, refers to a monovalent or divalent hydrocarbon radical having 2 to 6 carbon atoms, derived from a saturated alkyl, having at least one triple bond. One methylene (—CH$_2$—) group, of the alkynyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkynyl groups can be substituted by alkyl groups, as defined above, or by halogen atoms.

The term "heterocycle" as used herein, refers to a 3 to 10 membered ring, which can be aromatic or non-aromatic, saturated or unsaturated, containing at least one heteroatom selected form oxygen, nitrogen, sulfur, or combinations of at least two thereof, interrupting the carbocyclic ring structure. The heterocyclic ring can be interrupted by a C=O; the S and N heteroatoms can be oxidized. Heterocycles can be monocyclic or polycyclic. Heterocyclic ring moieties can be substituted by halogen atoms, sulfonyl groups, sulfoxide groups, nitro groups, cyano groups, —OC$_{1-6}$ alkyl groups, —SC$_{1-6}$ alkyl groups, —C$_{1-8}$ alkyl groups, —C$_{2-6}$ alkenyl groups, —C$_{2-6}$ alkynyl groups, ketone groups, alkylamino groups, amino groups, aryl groups, C$_{3-8}$ cycloalkyl groups or hydroxyl groups.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl C$_{1-6}$ alkyl groups, sulfoxide C$_{1-6}$ alkyl groups, sulfonamide groups, carboxcyclic acid groups, C$_{1-6}$ alkyl carboxylates (ester) groups, amide groups, nitro groups, cyano groups, —OC$_{1-6}$ alkyl groups, —SC$_{1-6}$ alkyl groups, —C$_{1-6}$ alkyl groups, —C$_{2-6}$ alkenyl groups, —C$_{2-6}$ alkynyl groups, ketone groups, aldehydes, alkylamino groups, amino groups, aryl groups, C$_{3-8}$ cycloalkyl groups or hydroxyl groups. Aryls can be monocyclic or polycyclic.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —C(O)R$^x$ wherein R$^x$ can be alkyl, aryl, cycloalkyl, cycloalkenyl, heterocycle as defined above.

The term "ester" as used herein, represents an organic compound having a carbonyl group linked to a carbon atom such as —C(O)OR$^x$ wherein R$^x$ can be alkyl, aryl, cycloalkyl, cycloalkenyl, heterocycle as defined above.

The term "amine" as used herein, represents a group of formula "—NR$^x$R$^y$", wherein R$^x$ and R$^y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—SO$_2$—".

The term "sulfate" as used herein, represents a group of formula "—O—S(O)$_2$—O—".

The term "sulfonate" as used herein, represents a group of the formula "—S(O)$_2$—O—".

The term "carboxylic acid" as used herein, represents a group of formula "—C(O)OH".

The term "nitro" as used herein, represents a group of formula "—NO$_2$".

The term "cyano" as used herein, represents a group of formula "—CN".

The term "amide" as used herein, represents a group of formula "—C(O)NR$^x$R$^y$," wherein R$^x$ and R$^y$ can be the same or independently H, alkyl, aryl, cycloalkyl, cycloalkenyl, heterocycle as defined above.

The term "sulfonamide" as used herein, represents a group of formula "—S(O)$_2$NR$^x$R$^y$" wherein R$^x$ and R$^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Other defined terms are used throughout this specification:
"Ac" refers to acetyl
"DCE" refers to dichloroethane
"DCM" refers to dichloromethane
"DMAP" refers to dimethylaminopyridine
"EDCI" refers to 1-ethyl-3-(3-dimethylaminopropyl)carbodiimide "Et" refers to ethyl
"iPr" refers to i-propyl
"Me" refers to methyl
"MeOH" refers to methanol
"PDGF" refers to platelet derived growth factor
"Ph" refers to phenyl
"PKs" refers to protein kinase
"RTKs" refers to receptor tyrosine kinase
"rt" refers to room temperature
"tBu" refers to t-butyl.
"THF" refers to tetrahydrofuran
"VEGF" refers to vascular endothelial growth factor
"VEGFR" refers to vascular endothelial growth factor receptor Compounds of the invention are tabulated in Table 1:

TABLE 1

List of compound names and structures

| Example | Structure | Compound Name |
|---------|-----------|---------------|
| 1 | 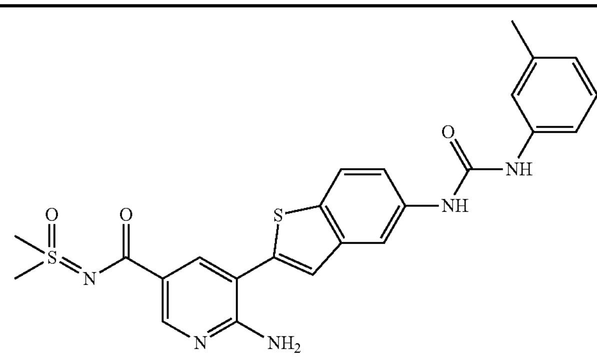 | 6-amino-N-[dimethyl(oxido)-λ$^4$-sulfanylidene]-5-[5-({[(3-methylphenyl)amino]carbonyl}-amino)-1-benzothien-2-yl]nicotinamide |

TABLE 1-continued

List of compound names and structures

| Example | Structure | Compound Name |
|---|---|---|
| 2 | 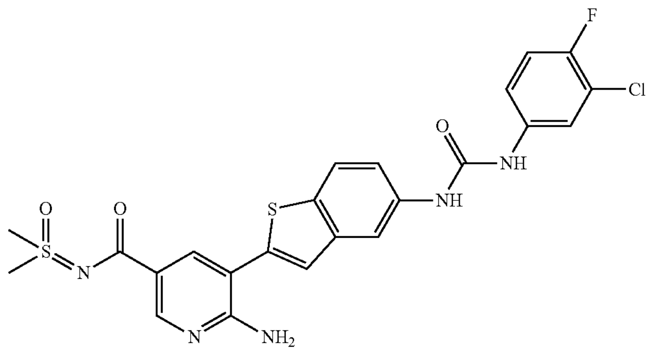 [SMILES: CS(C)(=O)=NC(=O)c1cnc(N)c(-c2cc3cc(NC(=O)Nc4ccc(F)c(Cl)c4)ccc3s2)c1] | 6-amino-5-[5-({[(3-chloro-4-fluorophenyl)amino]carbonyl}amino)-1-benzothien-2-yl]-N-[dimethyl(oxido)-$\lambda^4$-sulfanylidene]nicotinamide |
| 3 | 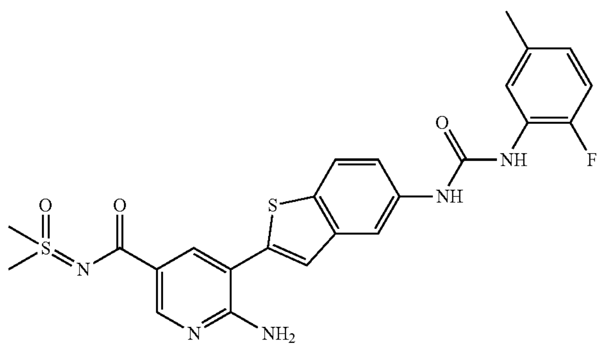 [SMILES: Cc1ccc(F)c(NC(=O)Nc2ccc3sc(-c4cc(C(=O)N=S(C)(C)=O)cnc4N)cc3c2)c1] | 6-amino-N-[dimethyl(oxido)-$\lambda^4$-sulfanylidene]-5-[5-({[(2-fluoro-5-methylphenyl)amino]carbonyl}-amino)-1-benzothien-2-yl]nicotinamide |
| 4 | 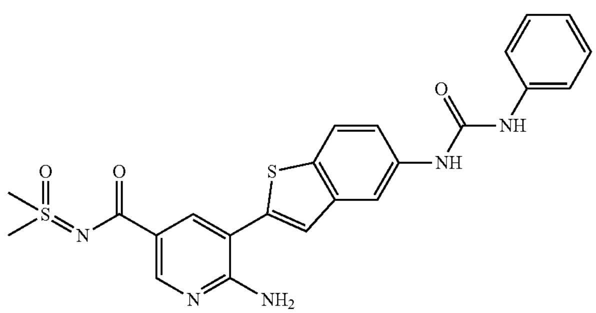 [SMILES: CS(C)(=O)=NC(=O)c1cnc(N)c(-c2cc3cc(NC(=O)Nc4ccccc4)ccc3s2)c1] | 6-amino-5-{5-[(anilinocarbonyl)amino]-1-benzothien-2-yl}-N-[dimethyl(oxido)-$\lambda^4$-sulfanylidene]nicotinamide |
| 5 | 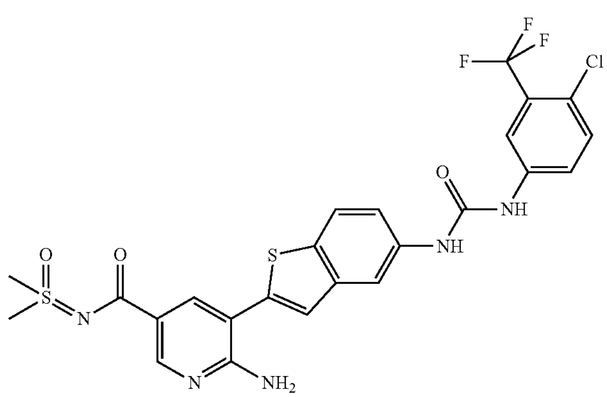 [SMILES: CS(C)(=O)=NC(=O)c1cnc(N)c(-c2cc3cc(NC(=O)Nc4ccc(Cl)c(C(F)(F)F)c4)ccc3s2)c1] | 6-amino-5-{5-[({[4-chloro-3-(trifluoromethyl)phenyl]amino}carbonyl)amino]-1-benzothien-2-yl}-N-[dimethyl(oxido)-$\lambda^4$-sulfanylidene]nicotinamide |

TABLE 1-continued

List of compound names and structures

| Example | Structure | Compound Name |
|---|---|---|
| 6 | 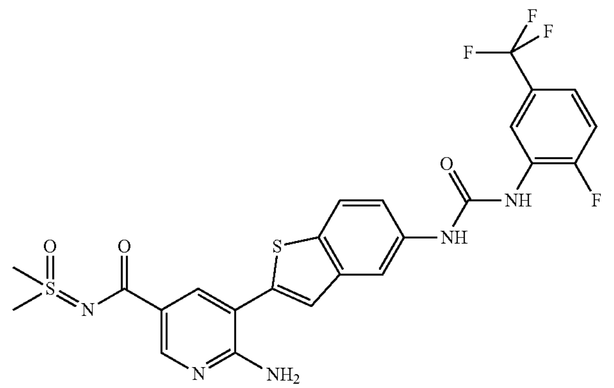 [SMILES: CS(C)(=O)=NC(=O)c1cnc(N)c(-c2cc3cc(NC(=O)Nc4cc(C(F)(F)F)ccc4F)ccc3s2)c1] | 6-amino-N-[dimethyl(oxido)-λ⁴-sulfanylidene]-5-{5-[({[2-fluoro-5-(trifluoromethyl)phenyl]amino}carbonyl)amino]-1-benzothien-2-yl}nicotinamide |
| 7 | 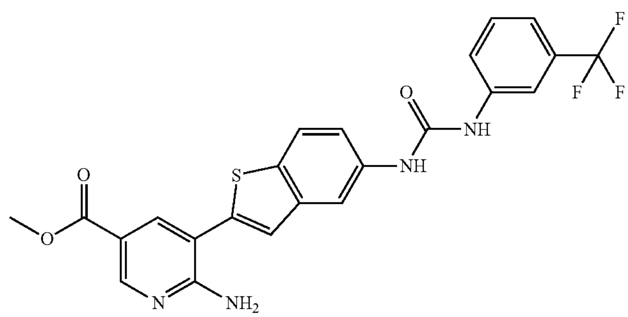 [SMILES: COC(=O)c1cnc(N)c(-c2cc3cc(NC(=O)Nc4cccc(C(F)(F)F)c4)ccc3s2)c1] | methyl 6-amino-5-{5-[({[3-(trifluoromethyl)phenyl]amino}carbonyl)amino]-1-benzothien-2-yl}nicotinate |
| 8 | 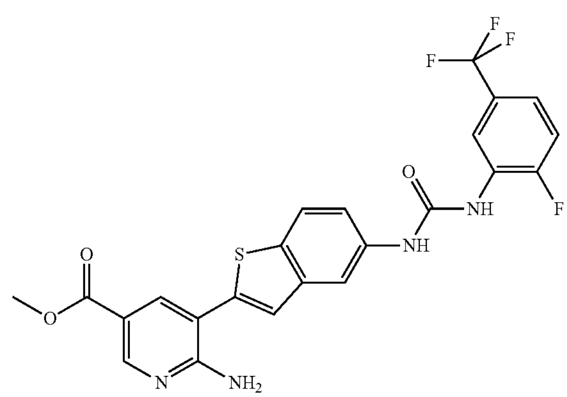 [SMILES: COC(=O)c1cnc(N)c(-c2cc3cc(NC(=O)Nc4cc(C(F)(F)F)ccc4F)ccc3s2)c1] | methyl 6-amino-5-{5-[({[2-fluoro-5-(trifluoromethyl)phenyl]amino}carbonyl)amino]-1-benzothien-2-yl}nicotinate |
| 9 | 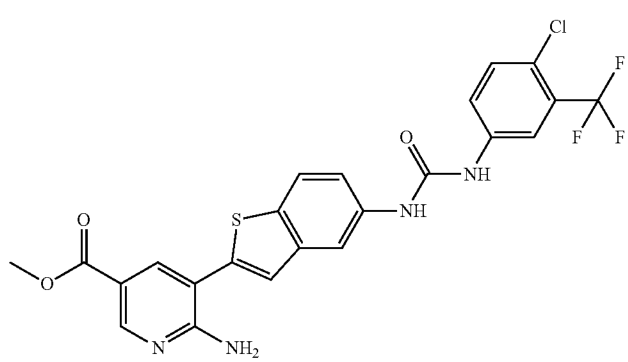 [SMILES: COC(=O)c1cnc(N)c(-c2cc3cc(NC(=O)Nc4ccc(Cl)c(C(F)(F)F)c4)ccc3s2)c1] | methyl 6-amino-5-{5-[({[4-chloro-3-(trifluoromethyl)phenyl]amino}carbonyl)amino]-1-benzothien-2-yl}nicotinate |

TABLE 1-continued

List of compound names and structures

| Example | Structure | Compound Name |
|---|---|---|
| 10 | 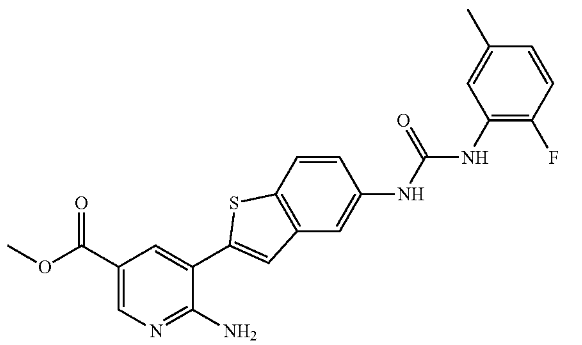 [SMILES: COC(=O)c1cnc(N)c(-c2cc3cc(NC(=O)Nc4cc(C)ccc4F)ccc3s2)c1] | methyl 6-amino-5-[5-({[(2-fluoro-5-methylphenyl)amino]carbonyl}-amino)-1-benzothien-2-yl]nicotinate |
| 11 | 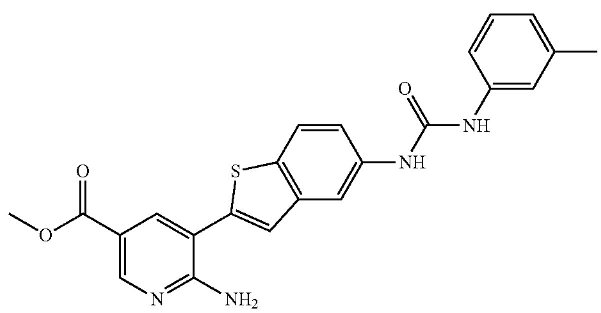 | methyl 6-amino-5-[5-({[(3-methylphenyl)amino]carbony}-amino)-1-benzothien-2-yl]nicotinate |
| 12 | 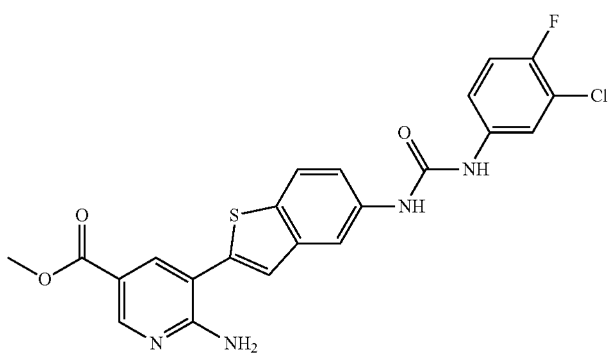 [SMILES: COC(=O)c1cnc(N)c(-c2cc3cc(NC(=O)Nc4ccc(F)c(Cl)c4)ccc3s2)c1] | methyl 6-amino-5-[5-({[(3-chloro-4-fluorophenyl)amino]carbonyl}amino)-1-benzothien-2-yl]nicotinate |
| 13 | 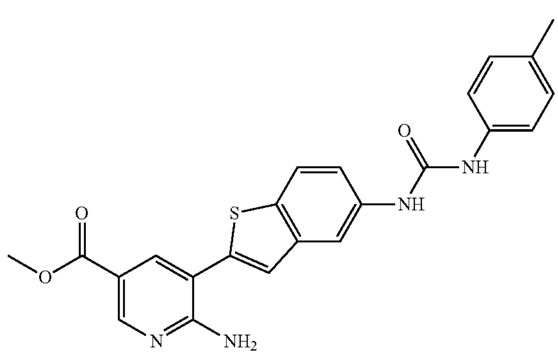 | methyl 6-amino-5-[5-({[(4-methylphenyl)amino]carbonyl}-amino)-1-benzothien-2-yl]nicotinate |

TABLE 1-continued

List of compound names and structures

| Example | Structure | Compound Name |
|---|---|---|
| 14 | 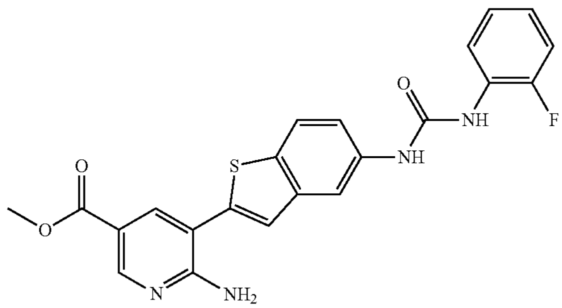 [SMILES: COC(=O)c1cnc(N)c(-c2cc3cc(NC(=O)Nc4ccccc4F)ccc3s2)c1] | methyl 6-amino-5-[5-({[(2-fluorophenyl)amino]carbonyl}amino)-1-benzothien-2-yl]nicotinate |
| 15 | 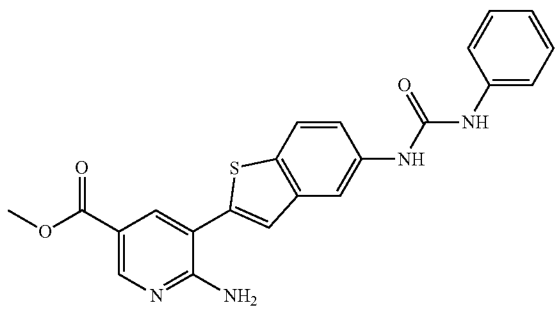 [SMILES: COC(=O)c1cnc(N)c(-c2cc3cc(NC(=O)Nc4ccccc4)ccc3s2)c1] | methyl 6-amino-5-{5-[(anilinocarbonyl)amino]-1-benzothien-2-yl}nicotinate |
| 16 | 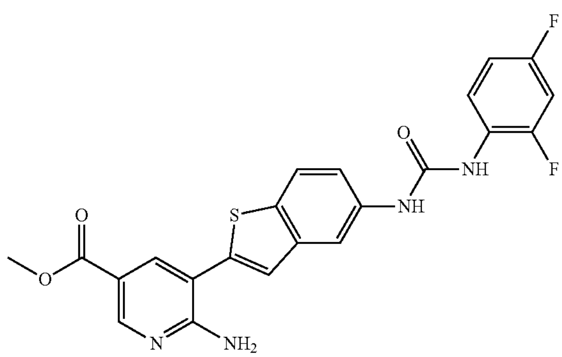 [SMILES: COC(=O)c1cnc(N)c(-c2cc3cc(NC(=O)Nc4ccc(F)cc4F)ccc3s2)c1] | methyl 6-amino-5-[5-({[(2,4-difluorophenyl)amino]carbonyl}amino)-1-benzothien-2-yl]nicotinate |
| 17 | 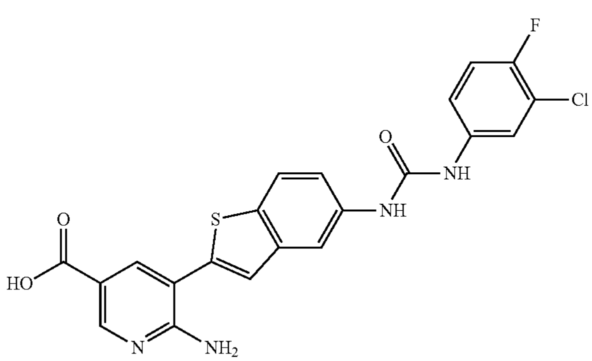 [SMILES: Nc1ncc(C(=O)O)cc1-c1cc2cc(NC(=O)Nc3ccc(F)c(Cl)c3)ccc2s1] | 6-amino-5-[5-({[(3-chloro-4-fluorophenyl)amino]carbonyl}amino)-1-benzothien-2-yl]nicotinic acid |

TABLE 1-continued

List of compound names and structures

| Example | Structure | Compound Name |
|---|---|---|
| 18 | 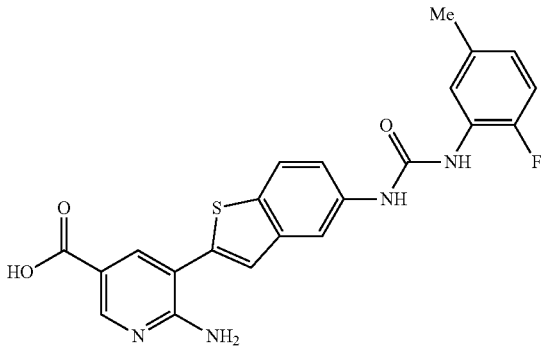 [SMILES: Cc1ccc(F)c(NC(=O)Nc2ccc3sc(-c4cc(C(=O)O)cnc4N)cc3c2)c1] | 6-amino-5-[5-({[(2-fluoro-5-methylphenyl)amino]carbonyl}-amino)-1-benzothien-2-yl]nicotinic acid |
| 19 | 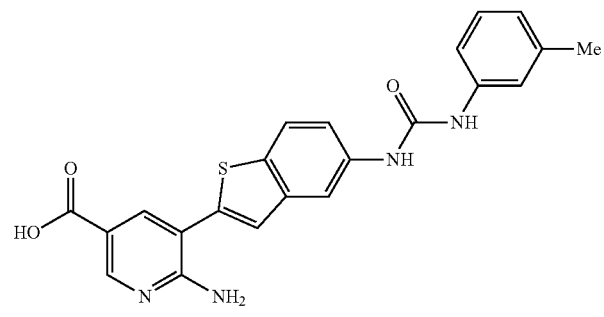 [SMILES: Cc1cccc(NC(=O)Nc2ccc3sc(-c4cc(C(=O)O)cnc4N)cc3c2)c1] | 6-amino-5-[5-({[(3-methylphenyl)amino]carbonyl}-amino)-1-benzothien-2-yl]nicotinic acid |
| 20 | 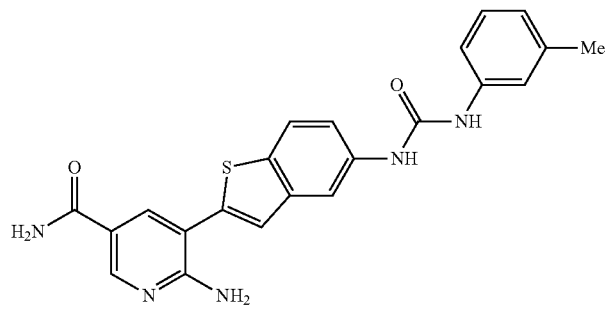 [SMILES: Cc1cccc(NC(=O)Nc2ccc3sc(-c4cc(C(N)=O)cnc4N)cc3c2)c1] | 6-amino-5-[5-({[(3-methylphenyl)amino]carbonyl}-amino)-1-benzothien-2-yl]nicotinamide |
| 21 | 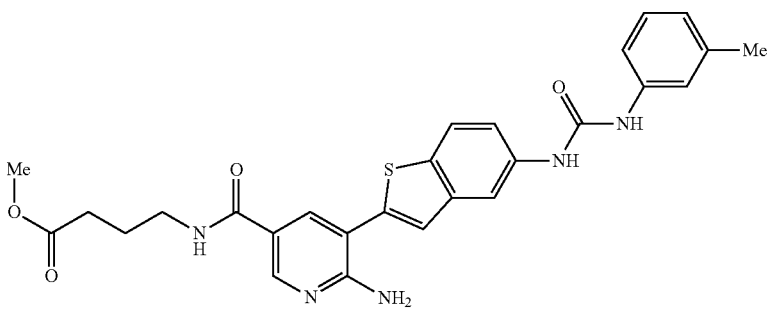 | methyl 4-[({6-amino-5-[5-({[(3-methylphenyl)amino]carbonyl}-amino)-1-benzothien-2-yl]pyridin-3-yl}carbonyl)amino]butanoate |

TABLE 1-continued

List of compound names and structures

| Example | Structure | Compound Name |
|---|---|---|
| 22 | 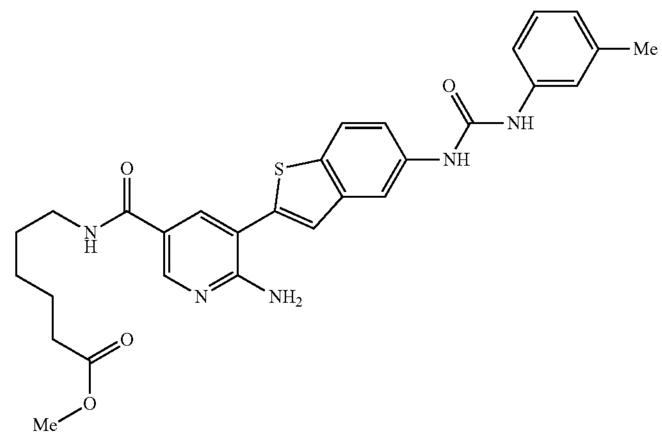 [SMILES: COC(=O)CCCCCNC(=O)c1cnc(N)c(-c2cc3cc(NC(=O)Nc4cccc(C)c4)ccc3s2)c1] | methyl 6-[({6-amino-5-[5-({[(3-methylphenyl)amino]carbony}-amino)-1-benzothien-2-yl]pyridin-3-yl}carbonyl)amino]hexanoate |
| 23 | 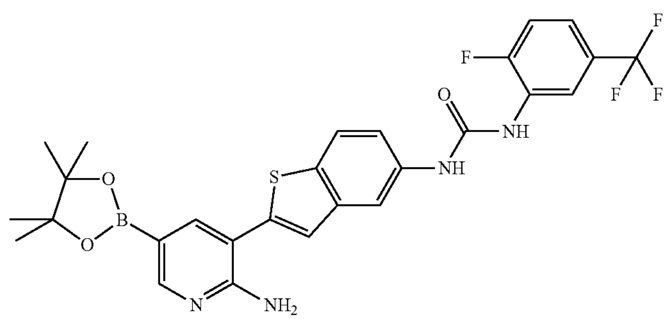 [SMILES: CC1(C)OB(c2cnc(N)c(-c3cc4cc(NC(=O)Nc5cc(C(F)(F)F)ccc5F)ccc4s3)c2)OC1(C)C] | 1-{2-[2-amino-5-(4,4,5,5-tetramethyl-1,3,2-dioxaborolan-2-yl)pyridin-3-yl]-1-benzothien-5-yl}-3-[2-fluoro-5-(trifluoromethyl)phenyl]urea |
| 24 | 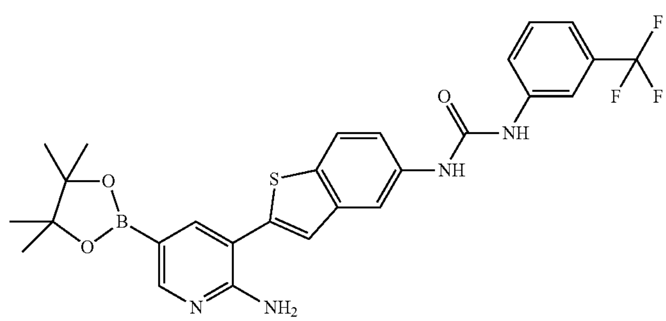 [SMILES: CC1(C)OB(c2cnc(N)c(-c3cc4cc(NC(=O)Nc5cccc(C(F)(F)F)c5)ccc4s3)c2)OC1(C)C] | 1-{2-[2-amino-5-(4,4,5,5-tetramethyl-1,3,2-dioxaborolan-2-yl)pyridin-3-yl]-1-benzothien-5-yl}-3-[3-(trifluoromethyl)phenyl]urea |
| 25 | 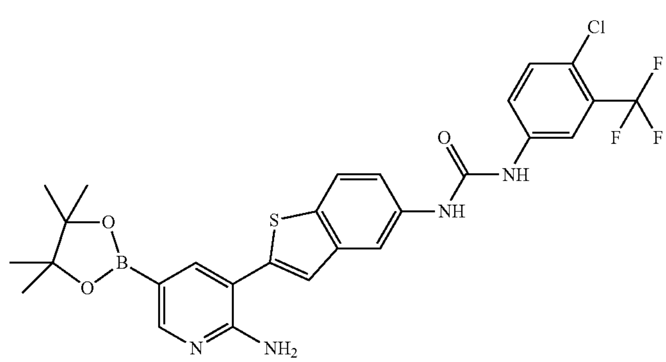 [SMILES: CC1(C)OB(c2cnc(N)c(-c3cc4cc(NC(=O)Nc5ccc(Cl)c(C(F)(F)F)c5)ccc4s3)c2)OC1(C)C] | 1-{2-[2-amino-5-(4,4,5,5-tetramethyl-1,3,2-dioxaborolan-2-yl)pyridin-3-yl]-1-benzothien-5-yl}-3-[4-chloro-3-(trifluoromethyl)phenyl]urea |

TABLE 1-continued

List of compound names and structures

| Example | Structure | Compound Name |
|---|---|---|
| 26 | 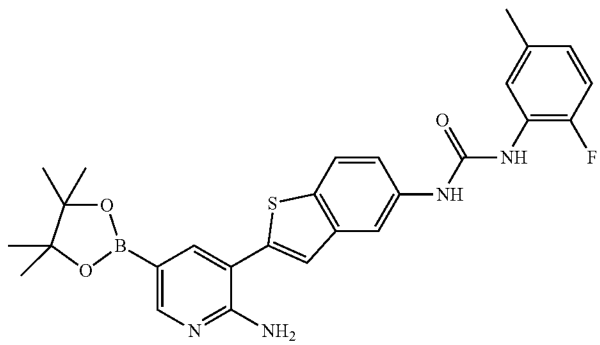 [SMILES: Cc1ccc(F)c(NC(=O)Nc2ccc3sc(-c4cc(B5OC(C)(C)C(C)(C)O5)cnc4N)cc3c2)c1] | 1-{2-[2-amino-5-(4,4,5,5-tetramethyl-1,3,2-dioxaborolan-2-yl)pyridin-3-yl]-1-benzothien-5-yl}-3-(2-fluoro-5-methylphenyl)urea |
| 27 | 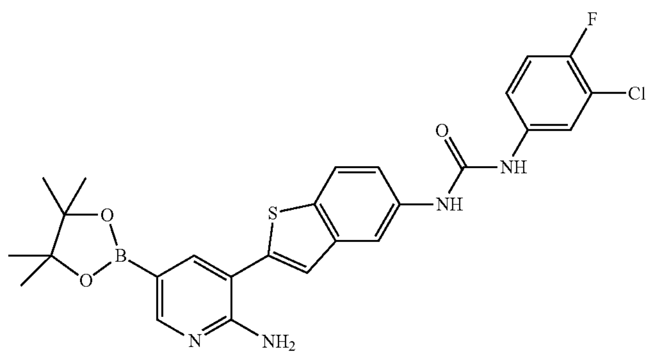 [SMILES: CC1(C)OB(c2cnc(N)c(-c3cc4cc(NC(=O)Nc5ccc(F)c(Cl)c5)ccc4s3)c2)OC1(C)C] | 1-{2-[2-amino-5-(4,4,5,5-tetramethyl-1,3,2-dioxaborolan-2-yl)pyridin-3-yl]-1-benzothien-5-yl}-3-(3-chloro-4-fluorophenyl)urea |
| 28 | 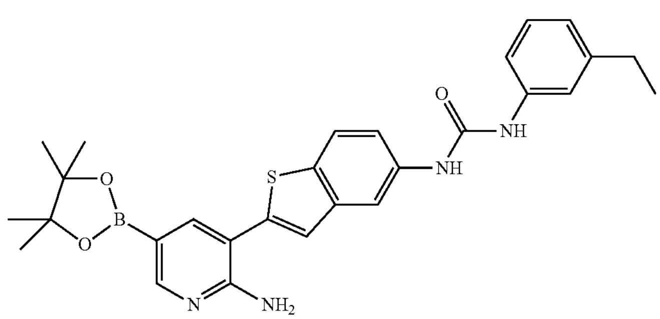 [SMILES: CCc1cccc(NC(=O)Nc2ccc3sc(-c4cc(B5OC(C)(C)C(C)(C)O5)cnc4N)cc3c2)c1] | 1-{2-[2-amino-5-(4,4,5,5-tetramethyl-1,3,2-dioxaborolan-2-yl)pyridin-3-yl]-1-benzothien-5-yl}-3-(3-ethylphenyl)urea |
| 29 | 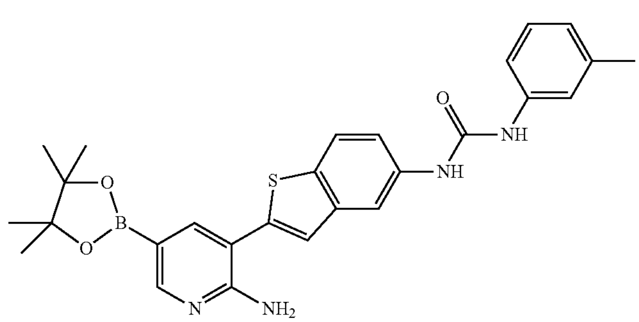 | 1-{2-[2-amino-5-(4,4,5,5-tetramethyl-1,3,2-dioxaborolan-2-yl)pyridin-3-yl]-1-benzothien-5-yl}-3-(3-methylphenyl)urea |

TABLE 1-continued

List of compound names and structures

| Example | Structure | Compound Name |
|---|---|---|
| 30 | 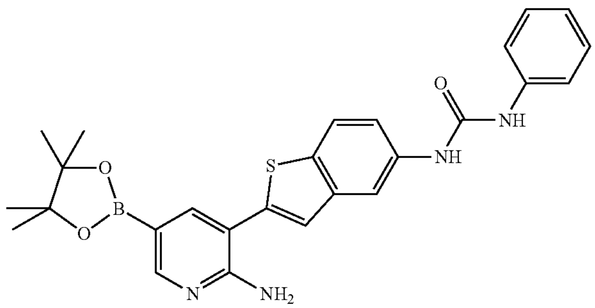 [SMILES: CC1(C)OB(c2cnc(N)c(-c3cc4cc(NC(=O)Nc5ccccc5)ccc4s3)c2)OC1(C)C] | 1-{2-[2-amino-5-(4,4,5,5-tetramethyl-1,3,2-dioxaborolan-2-yl)pyridin-3-yl]-1-benzothien-5-yl}-3-phenylurea |
| 31 | 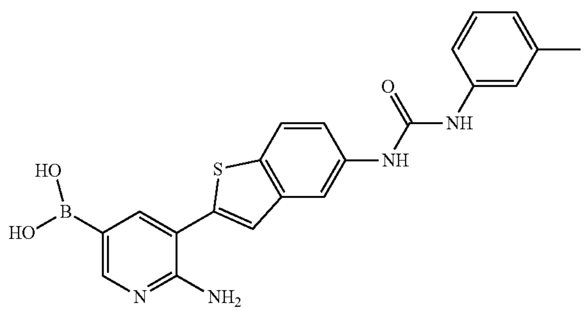 [SMILES: Cc1cccc(NC(=O)Nc2ccc3sc(-c4cc(B(O)O)cnc4N)cc3c2)c1] | {6-amino-5-[5-({[(3-methylphenyl)amino]carbonyl}-amino)-1-benzothien-2-yl]pyridin-3-yl}boronic acid |
| 32 | 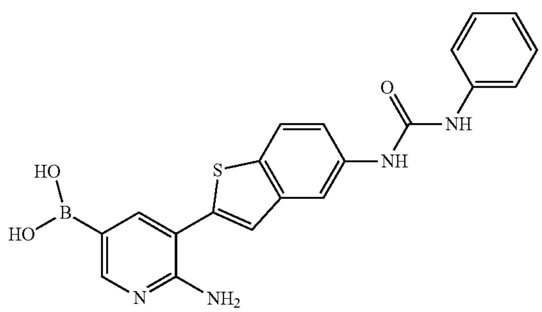 [SMILES: Nc1ncc(B(O)O)cc1-c1cc2cc(NC(=O)Nc3ccccc3)ccc2s1] | (6-amino-5-{5-[(anilinocarbonyl)amino]-1-benzothien-2-yl}pyridin-3-yl)boronic acid |
| 33 | 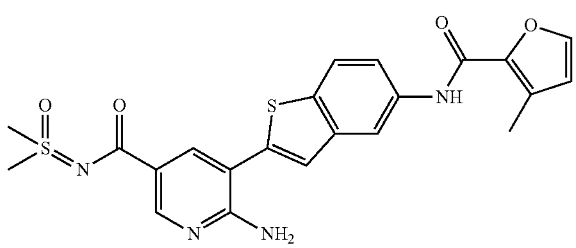 [SMILES: Cc1ccoc1C(=O)Nc1ccc2sc(-c3cc(C(=O)N=S(C)(C)=O)cnc3N)cc2c1] | 6-amino-N-[dimethyl(oxido)-λ$^4$-sulfanylidene]-5-{5-[(3-methyl-2-furoyl)amino]-1-benzothien-2-yl}nicotinamide |
| 34 | 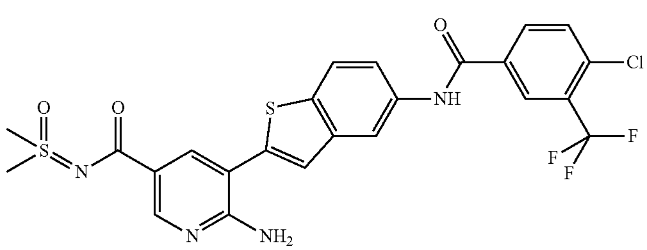 [SMILES: CS(C)(=O)=NC(=O)c1cnc(N)c(-c2cc3cc(NC(=O)c4ccc(Cl)c(C(F)(F)F)c4)ccc3s2)c1] | 6-amino-5-(5-{[4-chloro-3-(trifluoromethyl)benzoyl]-amino}-1-benzothien-2-yl)-N-[dimethyl(oxido)-λ$^4$-sulfanylidene]nicotinamide |

TABLE 1-continued

List of compound names and structures

| Example | Structure | Compound Name |
|---|---|---|
| 35 | 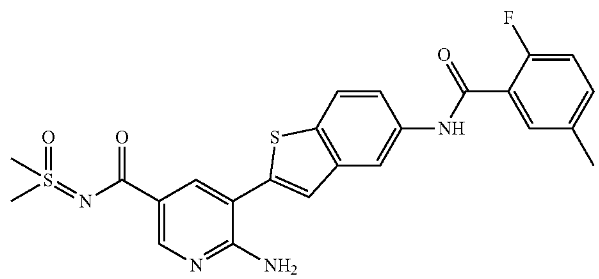 | 6-amino-N-[dimethyl(oxido)-λ⁴-sulfanylidene]-5-{5-[(2-fluoro-5-methylbenzoyl)amino]-1-benzothien-2-yl}nicotinamide |
| 36 | 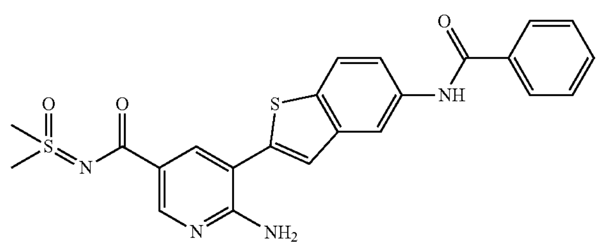 [SMILES: CS(C)(=O)=NC(=O)c1cnc(N)c(-c2cc3cc(NC(=O)c4ccccc4)ccc3s2)c1] | 6-amino-5-[5-(benzoylamino)-1-benzothien-2-yl]-N-[dimethyl(oxido)-λ⁴-sulfanylidene]nicotinamide |
| 37 | 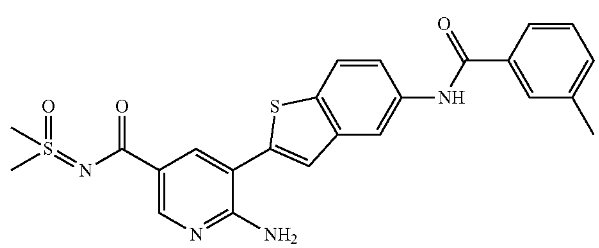 | 6-amino-N-[dimethyl(oxido)-λ⁴-sulfanylidene]-5-{5-[(3-methylbenzoyl)amino]-1-benzothien-2-yl}nicotinamide |
| 38 | 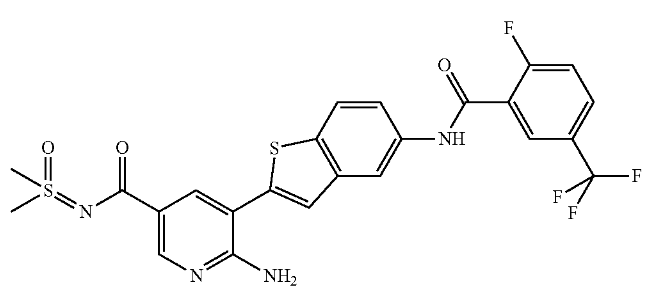 [SMILES: CS(C)(=O)=NC(=O)c1cnc(N)c(-c2cc3cc(NC(=O)c4cc(C(F)(F)F)ccc4F)ccc3s2)c1] | 6-amino-N-[dimethyl(oxido)-λ⁴-sulfanylidene]-5-(5-{[2-fluoro-5-(trifluoromethyl)benzoyl]amino}-1-benzothien-2-yl)nicotinamide |
| 39 | 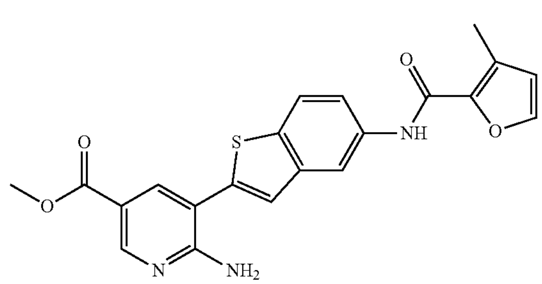 [SMILES: COC(=O)c1cnc(N)c(-c2cc3cc(NC(=O)c4occc4C)ccc3s2)c1] | methyl 6-amino-5-{5-[(3-methyl-2-furoyl)amino]-1-benzothien-2-yl}nicotinate |

TABLE 1-continued

List of compound names and structures

| Example | Structure | Compound Name |
|---|---|---|
| 40 | 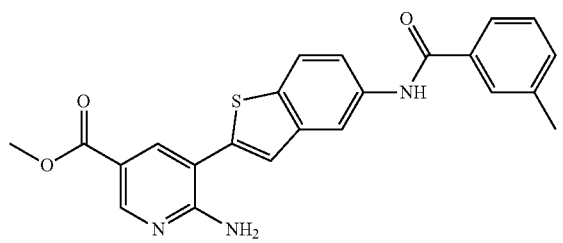 | 6-amino-5-{5-[(3-methylbenzoyl)amino]-1-benzothien-2-yl}nicotinate |
| 41 | 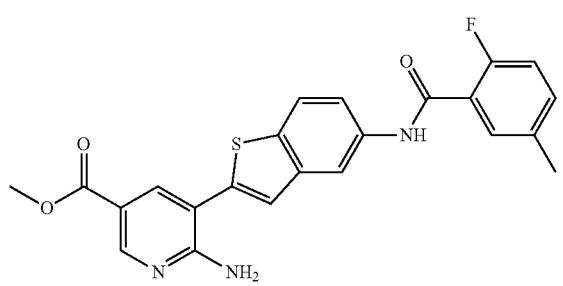 | methyl 6-amino-5-{5-[(2-fluoro-5-methylbenzoyl)amino]-1-benzothien-2-yl}nicotinate |
| 42 | 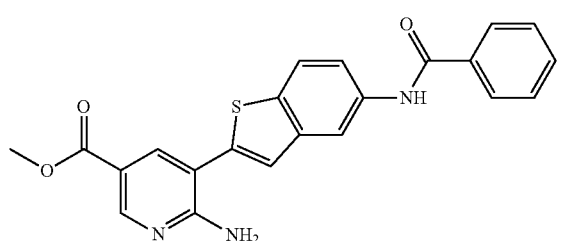 | methyl 6-amino-5-[5-(benzoylamino)-1-benzothien-2-yl]nicotinate |
| 43 | 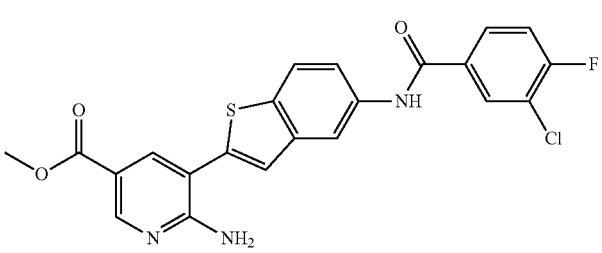 [SMILES: COC(=O)c1cnc(N)c(-c2cc3cc(NC(=O)c4ccc(F)c(Cl)c4)ccc3s2)c1] | methyl 6-amino-5-{5-[(3-chloro-4-fluorobenzoyl)amino]-1-benzothien-2-yl}nicotinate |
| 44 | 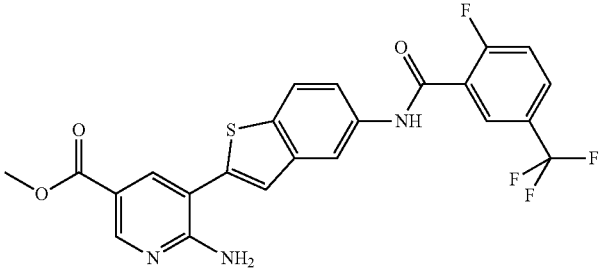 [SMILES: COC(=O)c1cnc(N)c(-c2cc3cc(NC(=O)c4cc(C(F)(F)F)ccc4F)ccc3s2)c1] | methyl 6-amino-5-(5-{[2-fluoro-5-(trifluoromethyl)benzoyl]amino}-1-benzothien-2-yl)nicotinate |

TABLE 1-continued

List of compound names and structures

| Example | Structure | Compound Name |
|---|---|---|
| 45 | 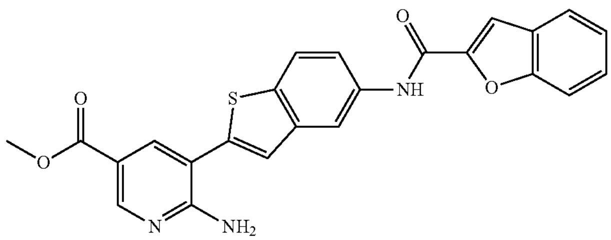 [SMILES: COC(=O)c1cnc(N)c(-c2cc3cc(NC(=O)c4cc5ccccc5o4)ccc3s2)c1] | methyl 6-amino-5-{5-[(1-benzofuran-2-ylcarbonyl)amino]-1-benzothien-2-yl}nicotinate |
| 46 | 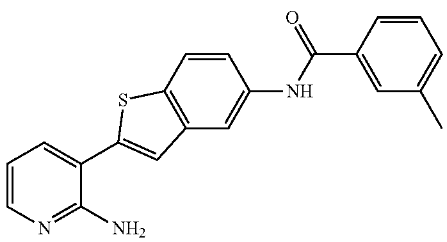 [SMILES: Cc1cccc(C(=O)Nc2ccc3sc(-c4cccnc4N)cc3c2)c1] | N-[2-(2-aminopyridin-3-yl)-1-benzothien-5-yl]-3-methylbenzamide |
| 47 | 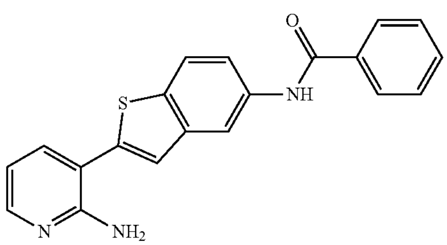 | N-[2-(2-aminopyridin-3-yl)-1-benzothien-5-yl]benzamide |
| 48 | 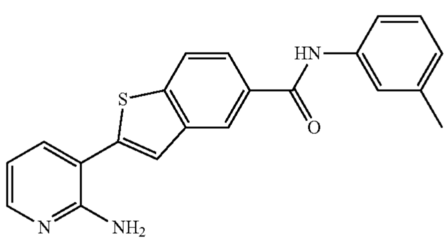 [SMILES: Cc1cccc(NC(=O)c2ccc3sc(-c4cccnc4N)cc3c2)c1] | 2-(2-aminopyridin-3-yl)-N-(3-methylphenyl)-1-benzothiophene-5-carboxamide |
| 49 | 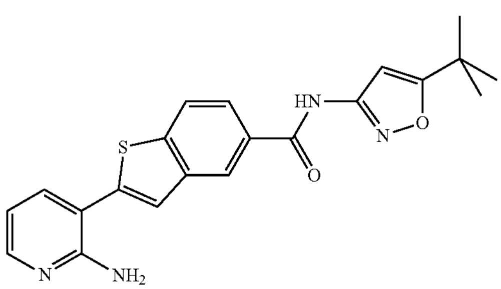 [SMILES: CC(C)(C)c1cc(NC(=O)c2ccc3sc(-c4cccnc4N)cc3c2)no1] | 2-(2-aminopyridin-3-yl)-N-(5-tert-butylisoxazol-3-yl)-1-benzothiophene-5-carboxamide |

TABLE 1-continued

List of compound names and structures

| Example | Structure | Compound Name |
|---|---|---|
| 50 | 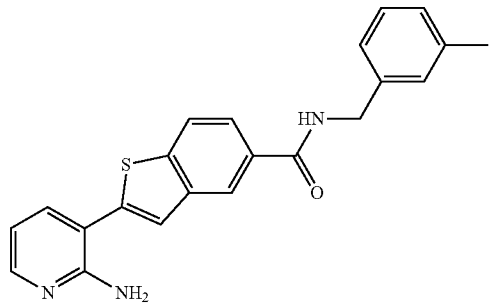 [SMILES: Cc1cccc(CNC(=O)c2ccc3sc(-c4cccnc4N)cc3c2)c1] | 2-(2-aminopyridin-3-yl)-N-(3-methylbenzyl)-1-benzothiophene-5-carboxamide |
| 51 | 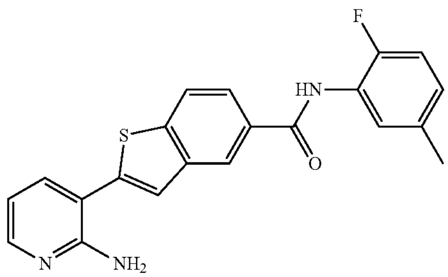 [SMILES: Cc1ccc(F)c(NC(=O)c2ccc3sc(-c4cccnc4N)cc3c2)c1] | 2-(2-aminopyridin-3-yl)-N-(2-fluoro-5-methylphenyl)-1-benzothiophene-5-carboxamide |
| 52 | 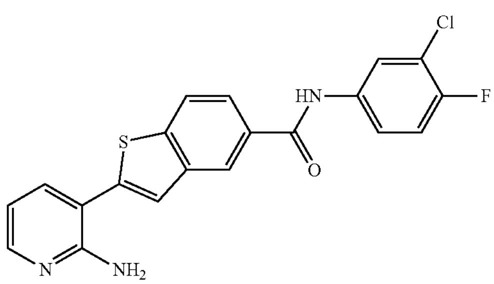 [SMILES: Nc1ncccc1-c1cc2cc(C(=O)Nc3ccc(F)c(Cl)c3)ccc2s1] | 2-(2-aminopyridin-3-yl)-N-(3-chloro-4-fluorophenyl)-1-benzothiophene-5-carboxamide |
| 53 | 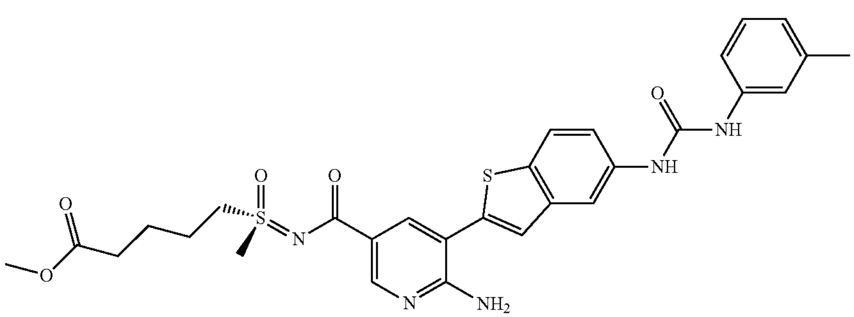 | methyl 5-[N-({6-amino-5-[5-({[(3-methylphenyl)amino]carbonyl}-amino)-1-benzothien-2-yl]pyridin-3-yl}carbonyl)-S-methylsulfonimidoyl]pentanoate |
| 54 | 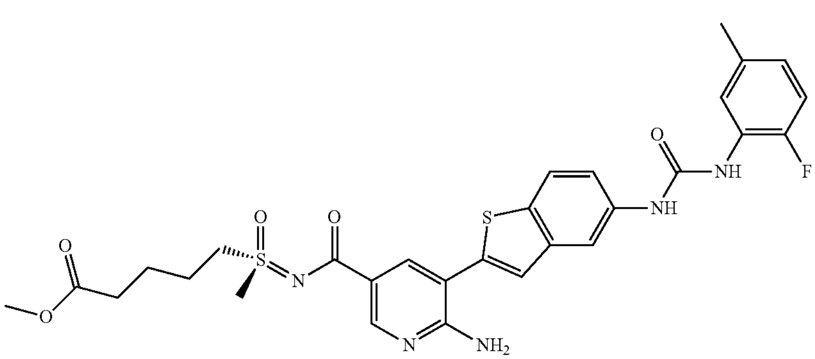 [SMILES: COC(=O)CCCC[S@](C)(=O)=NC(=O)c1cnc(N)c(-c2cc3cc(NC(=O)Nc4cc(C)ccc4F)ccc3s2)c1] | methyl 5-[N-({6-amino-5-[5-({[(2-fluoro-5-methylphenyl)amino]carbonyl}-amino)-1-benzothien-2-yl]pyridin-3-yl}carbonyl)-S-methylsulfonimidoyl]pentanoate |

TABLE 1-continued

List of compound names and structures

| Example | Structure | Compound Name |
|---|---|---|
| 55 | 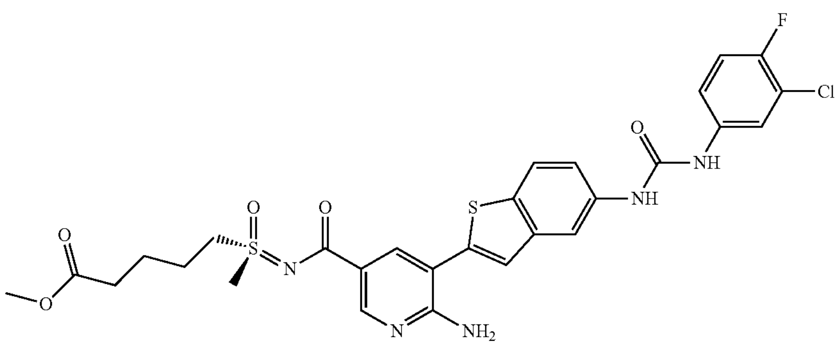 [SMILES: COC(=O)CCCC[S@](C)(=O)=NC(=O)c1cnc(N)c(-c2cc3cc(NC(=O)Nc4ccc(F)c(Cl)c4)ccc3s2)c1] | methyl 5-[N-({6-amino-5-[5-({[(3-chloro-4-fluorophenyl)amino]carbonyl}amino)-1-benzothien-2-yl]pyridin-3-yl}carbonyl)-S-methylsulfonimidoyl]pentanoate |
| 56 | 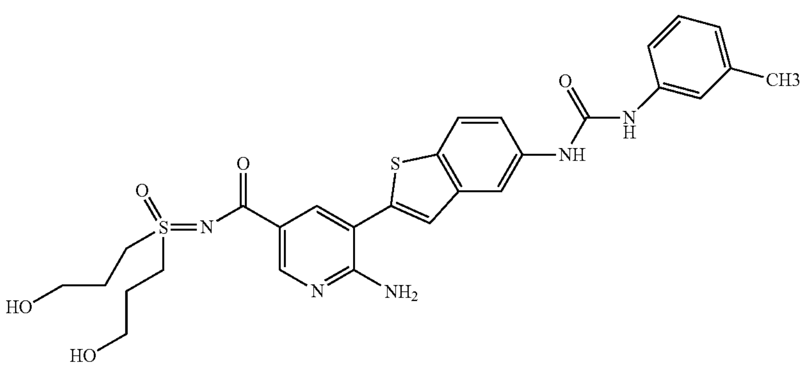 [SMILES: Cc1cccc(NC(=O)Nc2ccc3sc(-c4cc(C(=O)N=S(=O)(CCCO)CCCO)cnc4N)cc3c2)c1] | 6-amino-N-[bis(3-hydroxypropyl)(oxido)-λ⁴-sulfanylidene]-5-[5-({[(3-methylphenyl)amino]carbonyl}amino)-1-benzothien-2-yl]nicotinamide |
| 57 | 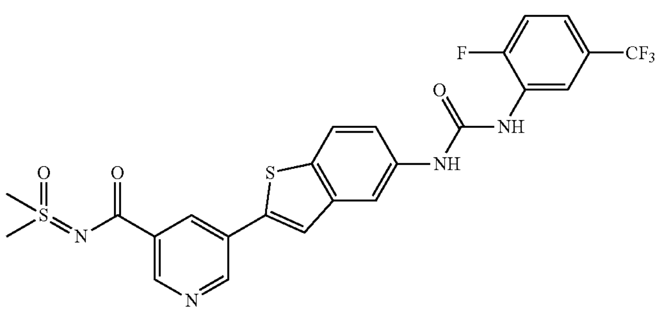 [SMILES: CS(C)(=O)=NC(=O)c1cncc(-c2cc3cc(NC(=O)Nc4cc(C(F)(F)F)ccc4F)ccc3s2)c1] | N-[dimethyl(oxido)-λ⁴-sulfanylidene]-5-{5-[({[2-fluoro-5-(trifluoromethyl)phenyl]amino}carbonyl)amino]-1-benzothien-2-yl}nicotinamide |
| 58 | 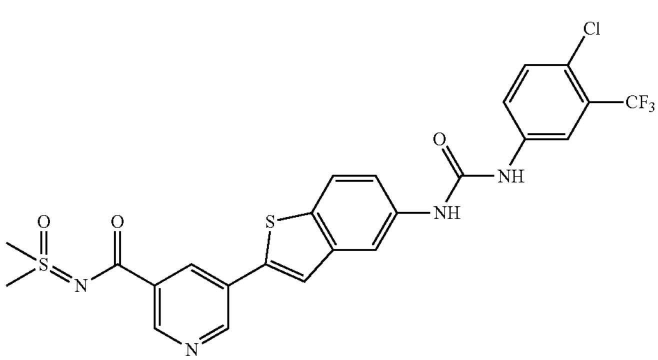 [SMILES: CS(C)(=O)=NC(=O)c1cncc(-c2cc3cc(NC(=O)Nc4ccc(Cl)c(C(F)(F)F)c4)ccc3s2)c1] | 5-{5-[({[4-chloro-3-(trifluoromethyl)phenyl]amino}carbonyl)amino]-1-benzothien-2-yl}-N-[dimethyl(oxido)-λ⁴-sulfanylidene]nicotinamide |

TABLE 1-continued

List of compound names and structures

| Example | Structure | Compound Name |
|---|---|---|
| 59 | 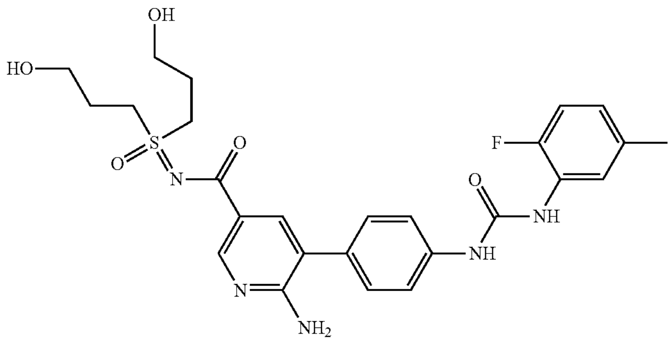 [SMILES: Cc1ccc(F)c(NC(=O)Nc2ccc(-c3cc(C(=O)N=S(=O)(CCCO)CCCO)cnc3N)cc2)c1] | 6-amino-N-[dimethyl(oxido)-λ⁴-sulfanylidene]-5-[4-({[(2-fluoro-5-methylphenyl)amino]carbonyl}amino)phenyl]-nicotinamide |
| 60 | 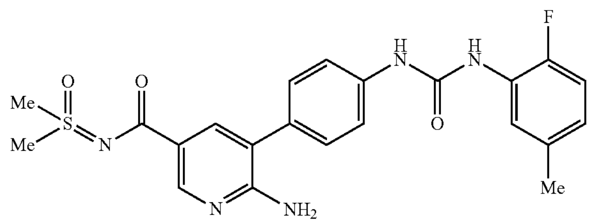 [SMILES: Cc1ccc(F)c(NC(=O)Nc2ccc(-c3cc(C(=O)N=S(C)(C)=O)cnc3N)cc2)c1] | 6-amino-N-[dimethyl(oxido)-λ⁴-sulfanylidene]-5-[4-({[(2-fluoro-5-methylphenyl)amino]carbonyl}-amino)phenyl]nicotinamide |
| 61 | 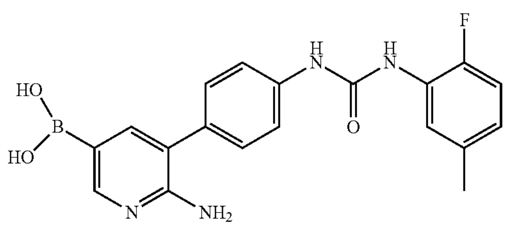 [SMILES: Cc1ccc(F)c(NC(=O)Nc2ccc(-c3cc(B(O)O)cnc3N)cc2)c1] | [6-amino-5-(4-{[(2-fluoro-5-methylphenyl)carbamoyl]-amino}-phenyl)pyridin-3-yl]boronic acid |
| 62 | 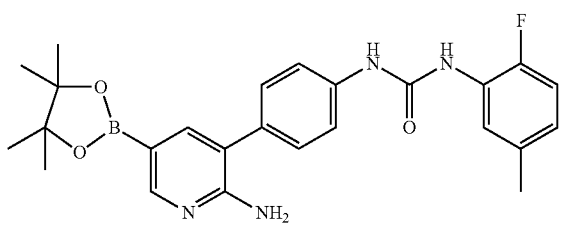 [SMILES: Cc1ccc(F)c(NC(=O)Nc2ccc(-c3cc(B4OC(C)(C)C(C)(C)O4)cnc3N)cc2)c1] | 1-{4-[2-amino-5-(4,4,5,5-tetramethyl-1,3,2-dioxaborolan-2-yl)pyridin-3-yl]phenyl}-3-(2-fluoro-5-methylphenyl)urea |
| 63 | 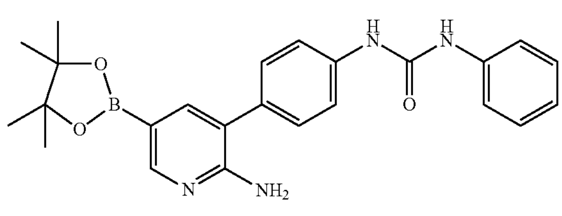 [SMILES: CC1(C)OB(c2cnc(N)c(-c3ccc(NC(=O)Nc4ccccc4)cc3)c2)OC1(C)C] | 1-{4-[2-amino-5-(4,4,5,5-tetramethyl-1,3,2-dioxaborolan-2-yl)pyridin-3-yl]phenyl}-3-phenylurea |
| 64 | 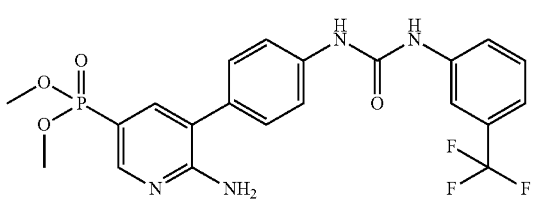 [SMILES: COP(=O)(OC)c1cnc(N)c(-c2ccc(NC(=O)Nc3cccc(C(F)(F)F)c3)cc2)c1] | dimethyl {6-amino-5-[4-({[3-(trifluoromethyl)phenyl]-carbamoyl}-amino)phenyl]pyridin-3-yl}phosphonate |

TABLE 1-continued

List of compound names and structures

| Example | Structure | Compound Name |
|---|---|---|
| 65 | 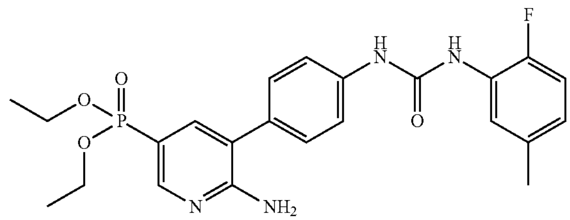 [SMILES: CCOP(=O)(OCC)c1cnc(N)c(-c2ccc(NC(=O)Nc3cc(C)ccc3F)cc2)c1] | diethyl [6-amino-5-(4-{[(2-fluoro-5-methylphenyl)carbamoyl]-amino}-phenyl)pyridin-3-yl]phosphonate |
| 66 | 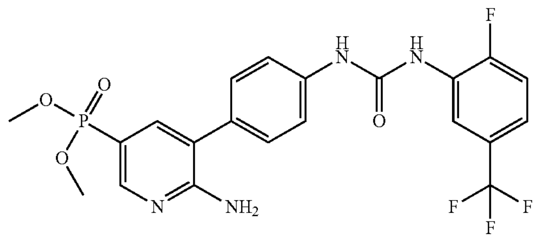 [SMILES: COP(=O)(OC)c1cnc(N)c(-c2ccc(NC(=O)Nc3cc(C(F)(F)F)ccc3F)cc2)c1] | dimethyl {6-amino-5-[4-({[2-fluoro-5-(trifluoromethyl)phenyl]-carbamoyl}-amino)phenyl]pyridin-3-yl}phosphonate |
| 67 | 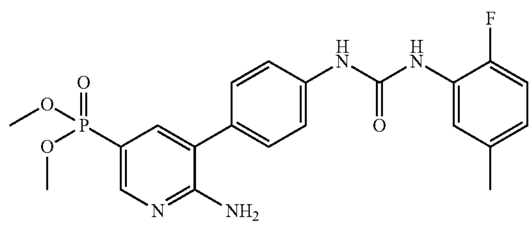 [SMILES: COP(=O)(OC)c1cnc(N)c(-c2ccc(NC(=O)Nc3cc(C)ccc3F)cc2)c1] | dimethyl [6-amino-5-(4-{[(2-fluoro-5-methyl-phenyl)carbamoyl]amino}-phenyl)pyridin-3-yl]phosphonate |
| 68 | 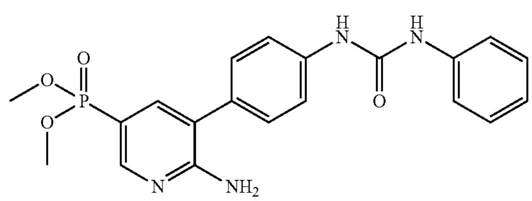 [SMILES: COP(=O)(OC)c1cnc(N)c(-c2ccc(NC(=O)Nc3ccccc3)cc2)c1] | dimethyl (6-amino-5-{4-[(phenylcarbamoyl)-amino]phenyl}-pyridin-3-yl)phosphonate |
| 69 | 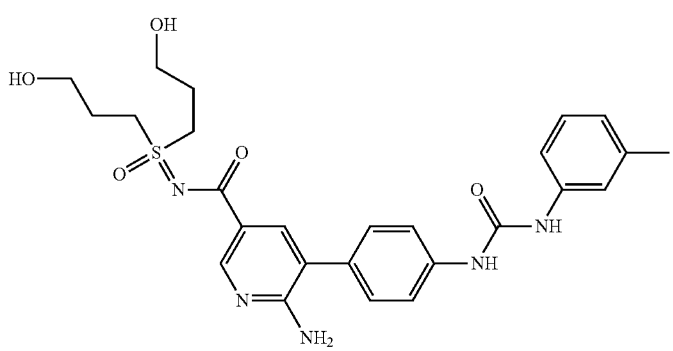 [SMILES: Cc1cccc(NC(=O)Nc2ccc(-c3cc(C(=O)N=S(=O)(CCCO)CCCO)cnc3N)cc2)c1] | 6-amino-N-[bis(3-hydroxypropyl)(oxido)-$\lambda^6$-sulfanylidene]-5-(4-{[(3-methylphenyl)carbamoyl]-amino}-phenyl)pyridine-3-carboxamide |

TABLE 1-continued

List of compound names and structures

| Example | Structure | Compound Name |
|---|---|---|
| 70 | 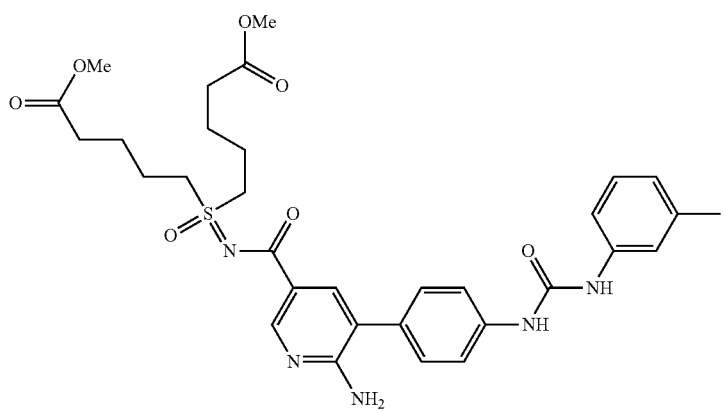 [SMILES: COC(=O)CCCCS(=O)(CCCCC(=O)OC)=NC(=O)c1cnc(N)c(-c2ccc(NC(=O)Nc3cccc(C)c3)cc2)c1] | dimethyl 5,5'-(N-{[6-amino-5-(4-{[(3-methylphenyl)-carbamoyl]amino}-phenyl)pyridin-3-yl]carbonyl}sulfonimidoyl)-dipentanoate |
| 71 | 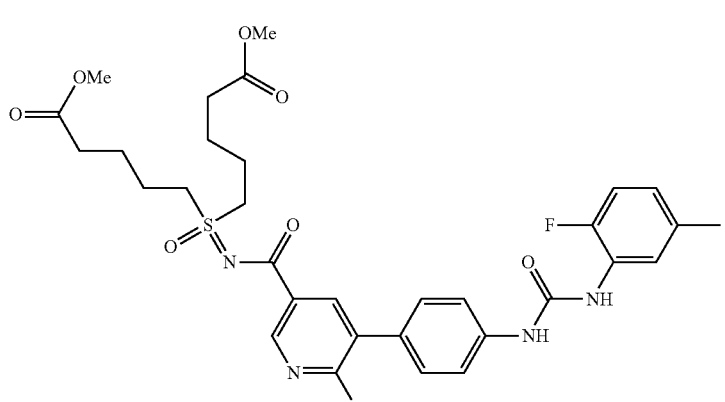 | dimethyl 5,5'-(N-{[6-amino-5-(4-{[(2-fluoro-5-methylphenyl)carbamoyl]-amino}-phenyl)pyridin-3-yl]carbonyl}sulfonimidoyl)-dipentanoate |
| 72 | 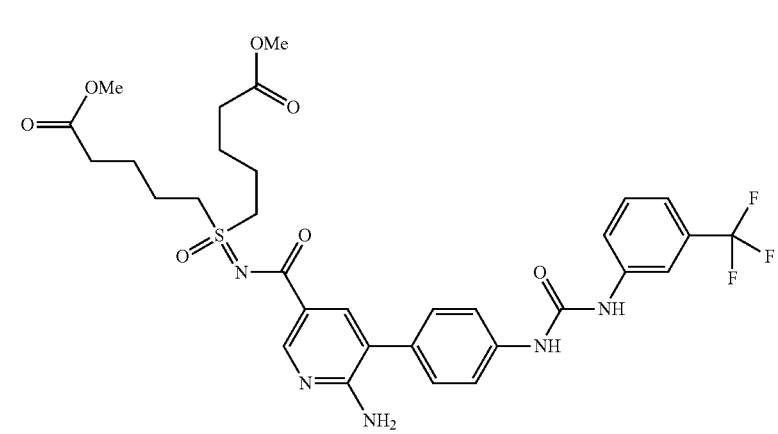 [SMILES: COC(=O)CCCCS(=O)(CCCCC(=O)OC)=NC(=O)c1cnc(N)c(-c2ccc(NC(=O)Nc3cccc(C(F)(F)F)c3)cc2)c1] | dimethyl 5,5'-[N-({6-amino-5-[4-({[3-(trifluoromethyl)phenyl]-carbamoyl}amino)phenyl]-pyridin-3-yl}carbonyl)sulfonimidoyl]-dipentanoate |
| 73 | 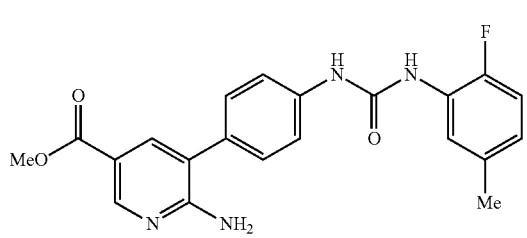 [SMILES: COC(=O)c1cnc(N)c(-c2ccc(NC(=O)Nc3cc(C)ccc3F)cc2)c1] | methyl 6-amino-5-(4-{[(2-fluoro-5-methyl)phenyl)-carbamoyl]amino}-phenyl]pyridin-3-carboxylate |

TABLE 1-continued

List of compound names and structures

| Example | Structure | Compound Name |
|---|---|---|
| 74 | (structure) | methyl 6-amino-5-(4-{[(2-fluoro-5-(trifluoromethyl)phenyl]-carbamoyl}amino)phenyl]-pyridine-3-3-carboxylate |
| 75 | (structure) | methyl 6-amino-5-[4-({[4-chloro-3-(trifluoromethyl)phenyl]-carbamoyl}-amino)phenyl]pyridine-3-carboxylate |
| 76 | (structure) | methyl 6-amino-5-{4-[(phenylcarbamoyl)-amino]phenyl}-pyridine-3-carboxylate |

Compounds of formula I and of formula II are useful as protein kinase inhibitors. As such, compounds of formula I and of formula II will be useful for treating diseases related to unregulated protein kinase signal transduction, for example, cancer, blood vessel proliferative disorders, fibrotic disorders, inflammatory disorders and neurodegenerative diseases. In particular, the compounds of the present invention are useful for treatment of mesangial cell proliferative disorders and metabolic diseases, lung carcinomas, breast carcinomas, Non Hodgkin's lymphomas, ovarian carcinoma, pancreatic cancer, malignant pleural mesothelioma, melanoma, arthritis, restenosis, hepatic cirrhosis, atherosclerosis, psoriasis, rosacea, diabetic mellitus, wound healing, inflammation and neurodegenerative diseases and preferably ophthalmic diseases, i.e. diabetic retinopathy, retinopathy of prematurity, macular edema, retinal vein occlusion, exudative or neovascular age-related macular degeneration, high-risk eyes (i.e. fellow eyes have neovascular age-related macular degeneration) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, atrophic macular degeneration, geographic atrophy, central serous retinopathy, cystoid macular edema, diabetic retinopathy, proliferative diabetic retinopathy, diabetic macular edema, rubeosis iridis, retinopathy of prematurity, Central and branch retinal vein occlusions, inflammatory/infectious retinal, neovascularization/edema, corneal neovascularization, hyperemia related to an actively inflamed pterygia, recurrent pterygia following excisional surgery, post-excision, progressive pterygia approaching the visual axis, prophylactic therapy to prevent recurrent pterygia, of post-excision, progressive pterygia approaching the visual axis, chronic low grade hyperemia associated with pterygia, neovascular glaucoma, iris neovascularization, idiopathic etiologies, presumed ocular histoplasmosis syndrome, retinopathy of prematurity, chronic allergic conjunctivitis, ocular rosacea, blepharoconjunctivitis, recurrent episcleritis, keratoconjunctivitis sicca, ocular graft vs host disease, etc.

Some compounds of Formula I and of Formula II and some of their intermediates may have at least one asymmetric center in their structure. This asymmetric center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I and of Formula II are able to form.

The acid addition salt form of a compound of Formula I and of Formula II that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahl & Camille G. Wermuth (Eds), Verlag Helvetica Chimica Acta-Zürich, 2002, 329-345).

The base addition salt form of a compound of Formula I and of Formula II that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345).

Compounds of Formula I and of Formula II and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.0001 and about 5% (w/v), preferably about 0.001 to about 2.0% (w/v) in liquid formulations.

For ophthalmic application, preferably solutions are prepared using a physiological saline solution as a major vehicle.

The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 µl.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner. The present invention is further directed to pharmaceutical compositions comprising a pharmaceutically effective amount of one or more of the above-described compounds and a pharmaceutically acceptable carrier or excipient, wherein said compositions are effective for treating the above diseases and conditions; especially ophthalmic diseases and conditions. Such a composition is believed to modulate signal transduction by a protein kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, rosacea, atherosclerosis, arthritis, and other disorders related to abnormal vasculogenesis and/or angiogenesis, such as exudative age related macular degeneration and diabetic retinopathy.

The present invention is further directed to pharmaceutical compositions comprising a pharmaceutically effective amount of the above-described compounds and a pharmaceutically acceptable carrier or excipient. Such a composition is believed to modulate signal transduction by a protein kinase, tyrosine kinase, or serine threonine kinase either by inhibition of catalytic activity, affinity to ATP or ability to interact with a substrate.

The present invention relates to compounds capable of regulating and/or modulating protein kinase signal transduction and more particularly receptor and non-receptor protein kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Protein kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit protein kinase signal transduction by affecting the enzymatic activity of the PKs and interfering with the signal transduced by such proteins. More particularly, the present invention is directed to compounds which regulate, modulate and/or inhibit the proteinkinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

The present invention concerns also processes for preparing the compounds of Formula I and of Formula II. The compounds of formula I and of formula II according to the invention can be prepared analogously to conventional methods as understood by the person skilled in the art of synthetic organic chemistry. The following Synthetic Schemes set forth below, illustrate how the compounds according to the invention can be made.

Scheme 1

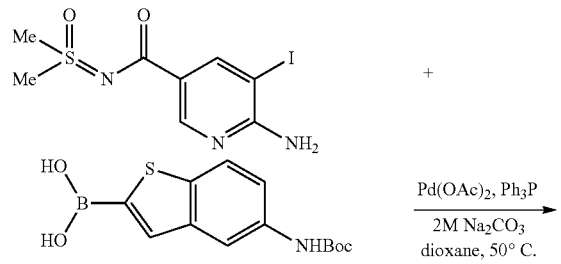

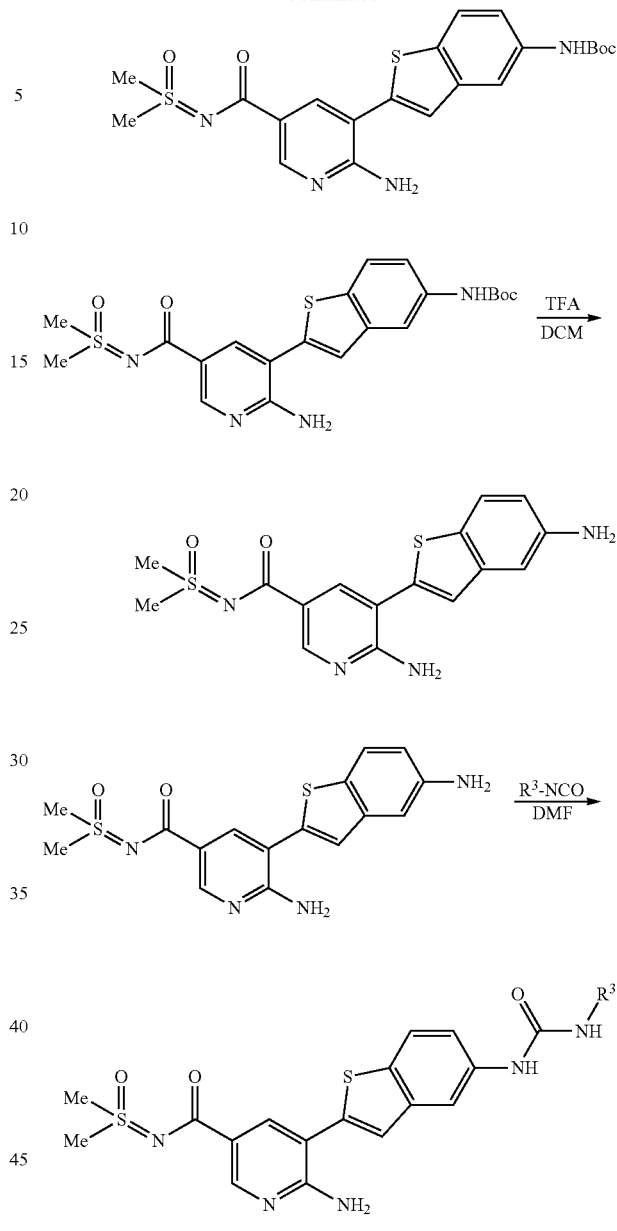

Scheme 2

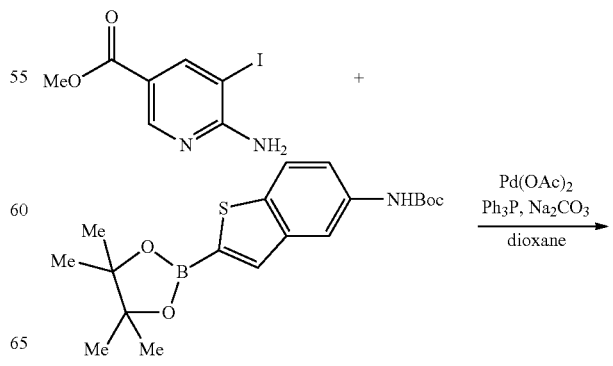

53
54
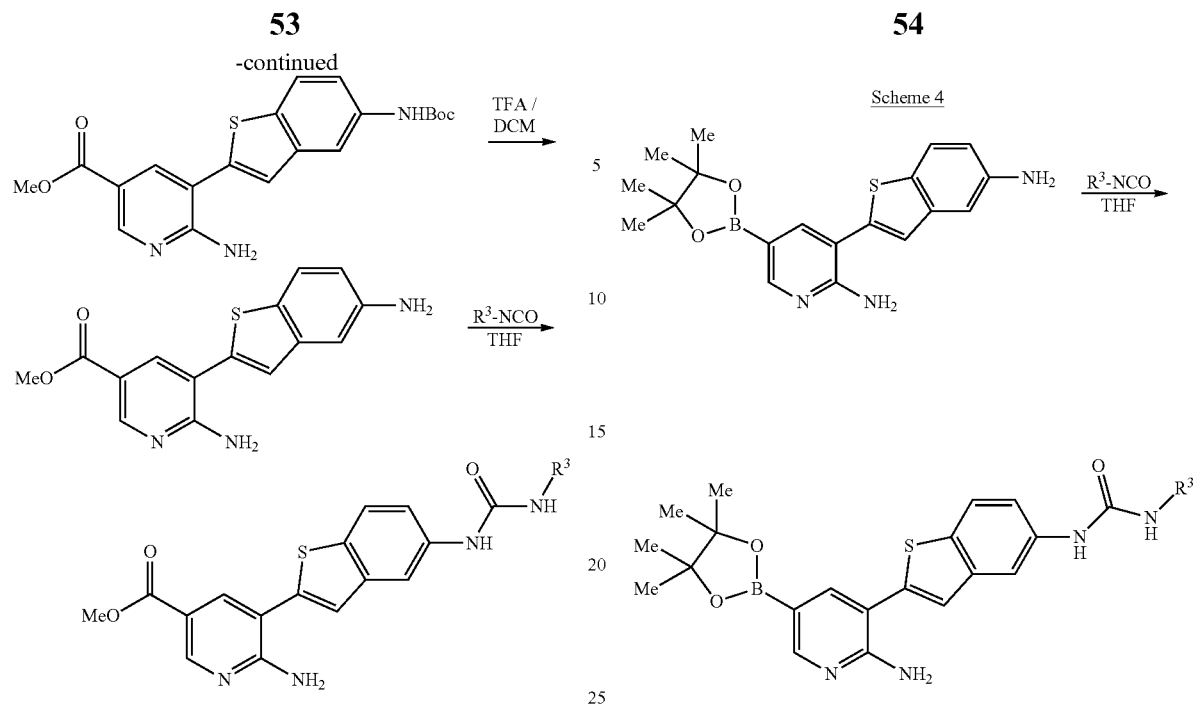
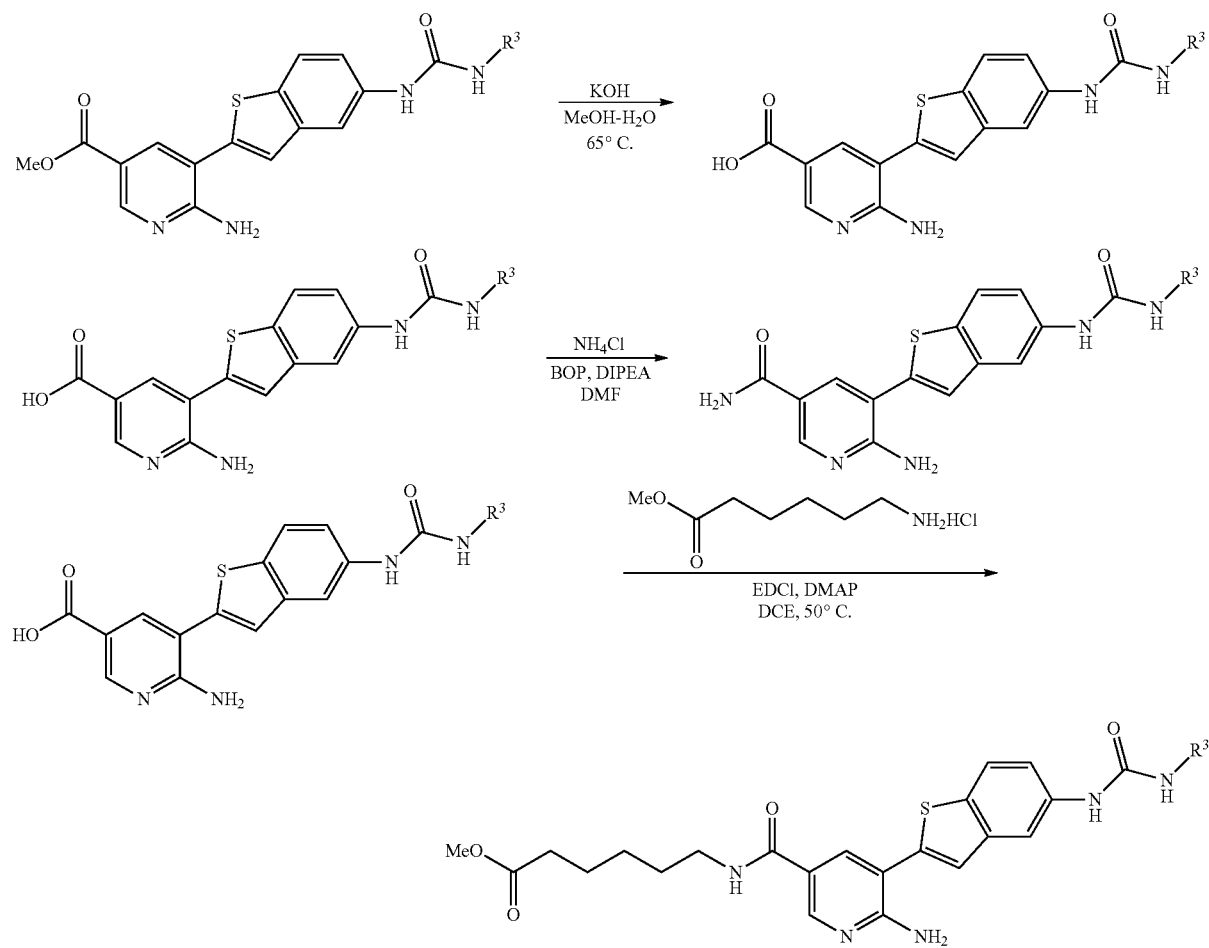

Scheme 5
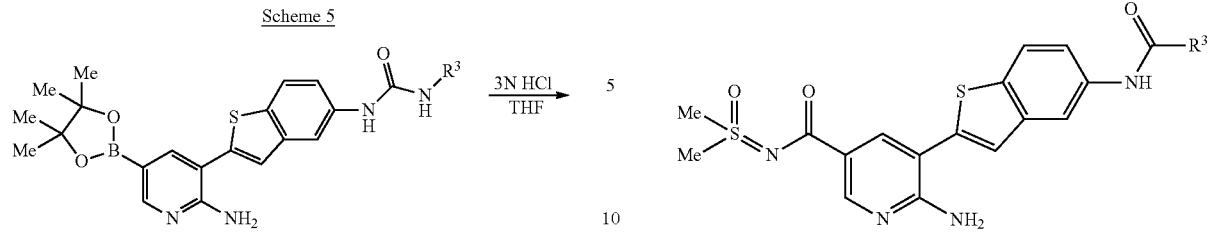
Scheme 6
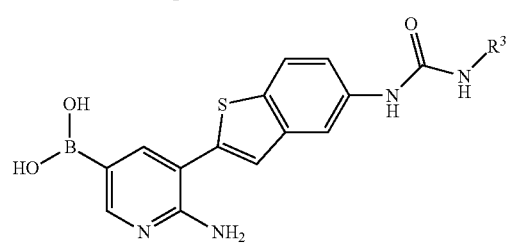
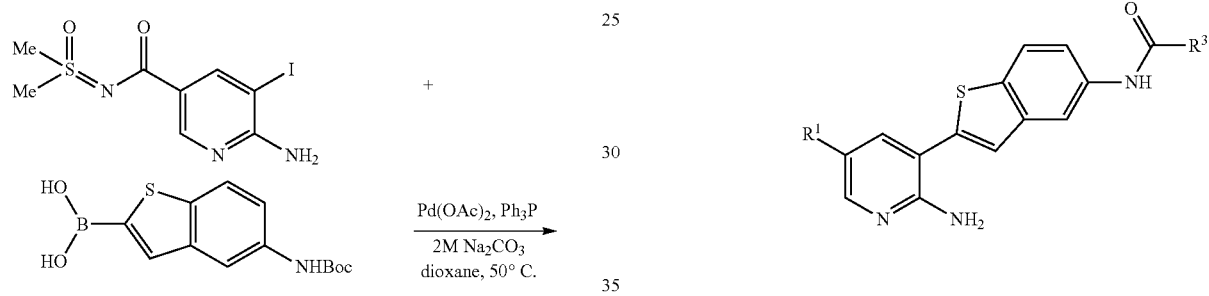
Scheme 7
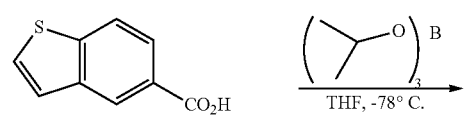
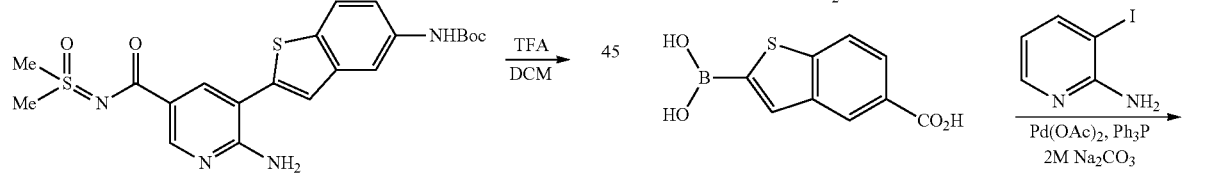
Scheme 8
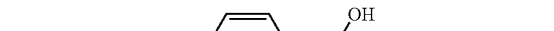
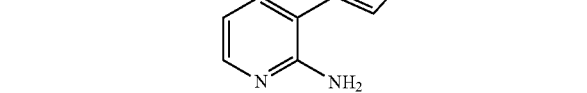

Scheme 9
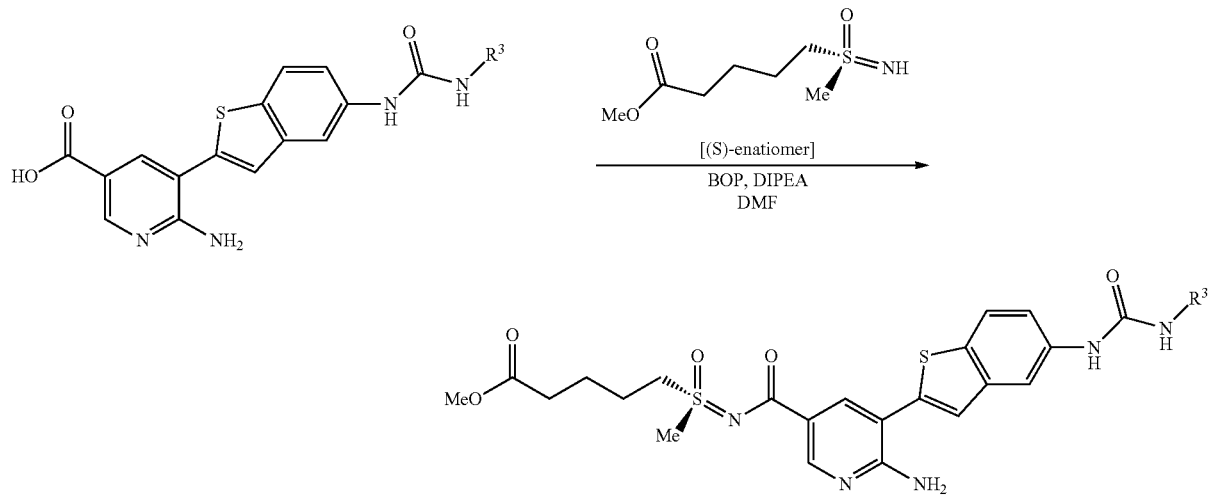
Scheme 10
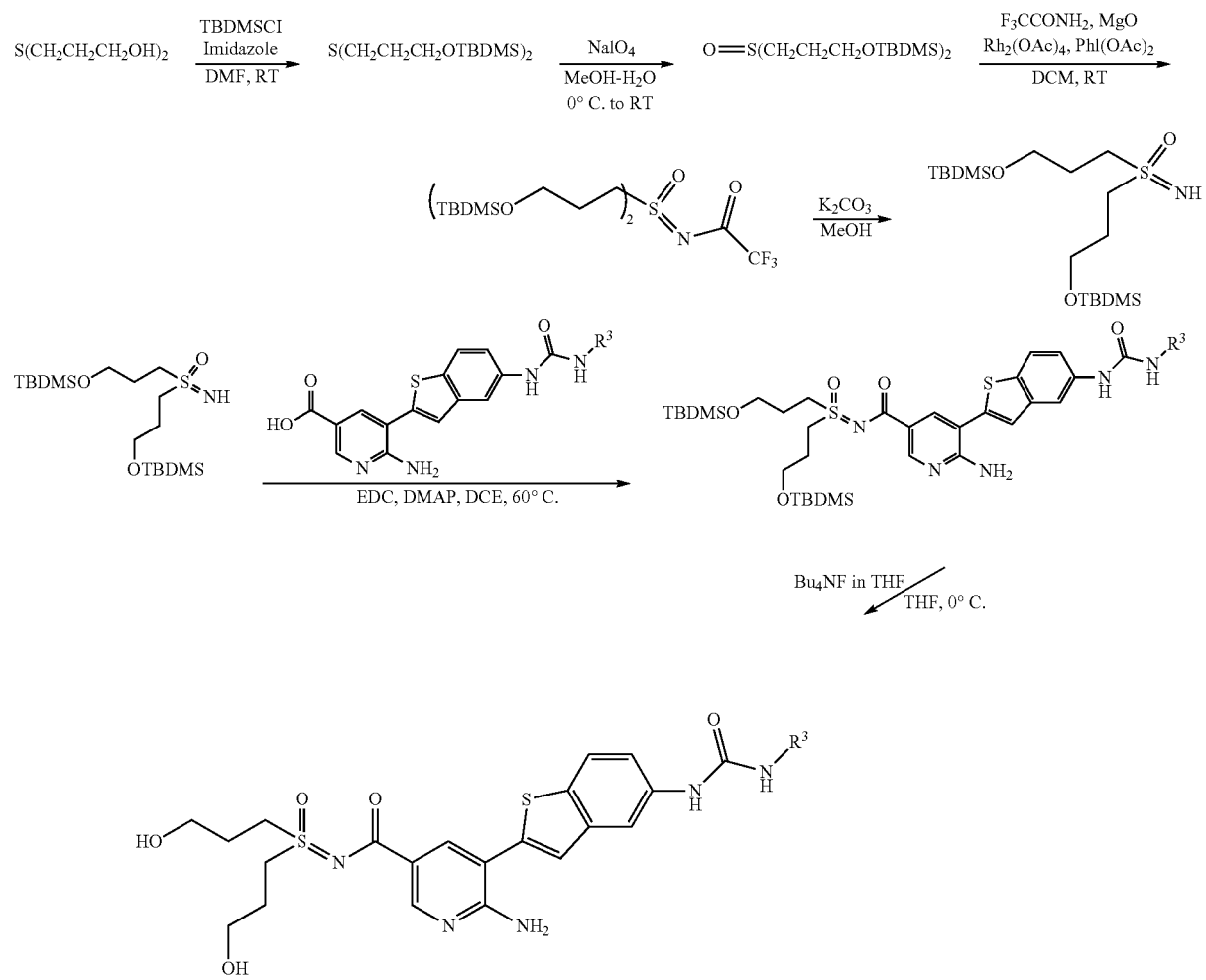

At this stage, those skilled in the art will appreciate that many additional compounds that fall under the scope of the invention may be prepared by performing various common chemical reactions. Details of certain specific chemical transformations are provided in the examples.

Those skilled in the art will be able to routinely modify and/or adapt the following scheme to synthesize any compounds of the invention covered by Formula I and of Formula II.

The present invention is not to be limited in scope by the exemplified embodiments which are intended as illustrations of single aspects of the invention only. Indeed, various modifications of the invention in addition to those described herein will become apparent to those skilled in the art from the foregoing description.

DETAILED DESCRIPTION OF THE INVENTION

The present invention relates to a method of regulating, modulating or inhibiting proteinkinases, whether of the receptor or non-receptor class, for the prevention and/or treatment of disorders related to unregulated protein kinase signal transduction, including cell growth, metabolic, and blood vessel proliferative disorders, which comprises administering a pharmaceutical composition comprising a therapeutically effective amount of at least one kinase inhibitor as described herein.

In another aspect, the invention provides the use of at least one kinase inhibitor for the manufacture of a medicament for the treatment of a disease or a condition mediated by tyrosine kinases in a mammal.

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hydrogen $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACDLabs version 12.5. Some of the intermediate and reagent names used in the examples were generated with software such as Chem Bio Draw Ultra version 12.0 or Auto Nom 2000 from MDL ISIS Draw 2.5 SP1.

In general, characterization of the compounds is performed according to the following methods; NMR spectra are recorded on 300 or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by medium pressure liquid chromatography, unless noted otherwise.

Preparation 1

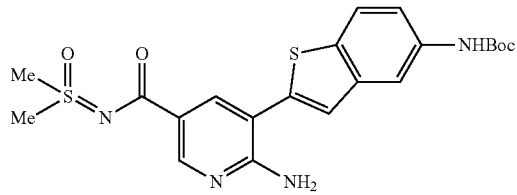

tert-butyl {2-[2-amino-5-({[dimethyl(oxido)-λ$^4$-sulfanylidene]amino}carbonyl)pyridin-3-yl]-1-benzothien-5-yl}carbamate To the degassed mixture of 6-amino-N-[dimethyl(oxido)-λ$^4$-sulfanylidene]-5-iodonicotinamide (1.19 g, 3.51 mmol, 1 eq), 5-tert-butoxycarbonylaminobenzothiophene-2-boronic acid (1.52 g, 1.15 eq), and aq sodium carbonate (2M, 5.27 mL, 3 eq) in dioxane (7.5 mL) was added Ph$_3$P (184 mg, 0.2 eq) and Pd(OAc)$_2$ (79 mg, 0.1 eq). The mixture was heated to 50° C. with vigorous stirring for 30 minutes. The reaction mixture was then partitioned between aq NH$_4$Cl and EtOAc. The organic layer was isolated, washed with sat aq NaHCO$_3$, brine, and finally dried with anhydrous sodium sulfate. The upper solution was decanted, concentrated, and the foamy oily residue was subject to a gradient column chromatography (EtOAc-Hex 3:1 to 6:1) yielding tert-butyl {2-[2-amino-5-({[dimethyl(oxido)-λ$^4$-sulfanylidene]amino}carbonyl)pyridin-3-yl]-1-benzothien-5-yl}carbamate as a white solid in amount of 1.274 g (79%).

Preparation 2

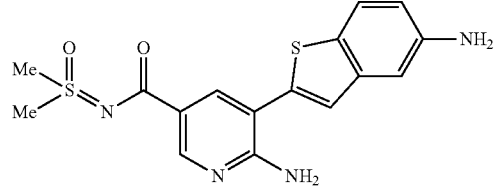

6-amino-5-(5-amino-1-benzothien-2-yl)-N-[dimethyl(oxido)-λ$^4$-sulfanylidene]nicotinamide To the mixture of tert-butyl {2-[2-amino-5-({[dimethyl(oxido)-λ⁴-sulfanylidene]amino}carbonyl)pyridin-3-yl]-1-benzothien-5-yl}carbamate (1.23 g, 2.67 mmol, 1 eq) in dichloromethane (6 mL) at 0° C. was added dropwise trifluoroacetic acid (5.16 mL, 20 eq). During this process the reaction mixture became a brown solution. The reaction was stirred at 0° C. for 15 minutes and then at room temperature for 3 hours. The reaction was partitioned between DCM and cold saturated aq NaHCO₃. The organic layer was isolated, washed with brine and dried with anhydrous sodium sulfate. The clear layer was decanted, concentrated, and the brown solid residue was treated with EtOAc. An orange colored solid was obtained upon filtration giving 6-amino-5-(5-amino-1-benzothien-2-yl)-N-[dimethyl(oxido)-λ⁴-sulfanylidene]nicotinamide in amount of 0.837 g (87%).

Example 1

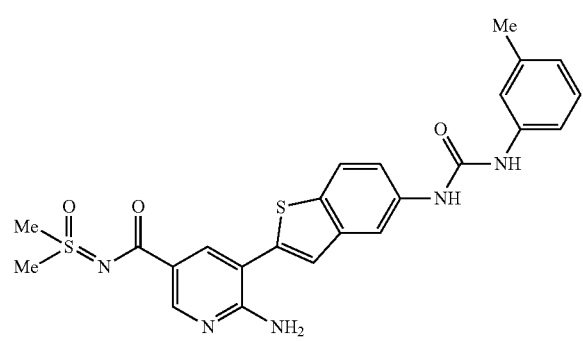

6-amino-N-[dimethyl(oxido)-λ⁴-sulfanylidene]-5-[5-({[(3-methylphenyl)amino]carbonyl}amino)-1-benzothien-2-yl]nicotinamide To the solution of 6-amino-5-(5-amino-1-benzothien-2-yl)-N-[dimethyl(oxido)-λ⁴-sulfanylidene]nicotinamide (72 mg, 0.2 mmol. 1 eq) in anhydrous DMF (2 mL) at room temperature was added dropwise m-tolylisocyanate (0.03 mL, 1.2 eq). After the reaction solution was stirred at rt for 2 hours, it was diluted with EtOAc, washed sequentially with saturated aq NaHCO₃, aq NH₄Cl, brine, and finally dried with anhydrous sodium sulfate. The organic layer was decanted, concentrated, and the solid residue was triturated with DCM with stirring. A lightly pink solid was obtained upon filtration to yield 6-amino-N-[dimethyl(oxido)-λ⁴-sulfanylidene]-5-[5-({[(3-methylphenyl)amino]carbonyl}amino)-1-benzothien-2-yl]nicotinamide in amount of 91 mg (92%).

¹H NMR (DMSO-d₆) δ: 8.78 (s, 1H), 8.61 (s, 1H), 8.61 (d, J=2.1 Hz, 1H), 8.10 (dd, J=2.1, 0.3 Hz, 1H), 8.02 (d, J=2.1 Hz, 1H), 7.87 (d, J=8.5 Hz, 1H), 7.59 (s, 1H), 7.37 (dd, J=8.8, 2.1 Hz, 1H), 7.32 (s, 1H), 7.25 (d, J=8.2 Hz, 1H), 7.16 (t, J=7.8 Hz, 1H), 6.80 (d, J=7.3 Hz, 1H), 6.76 (s, 2H), 3.44 (s, 6H), 2.29 (s, 3H).

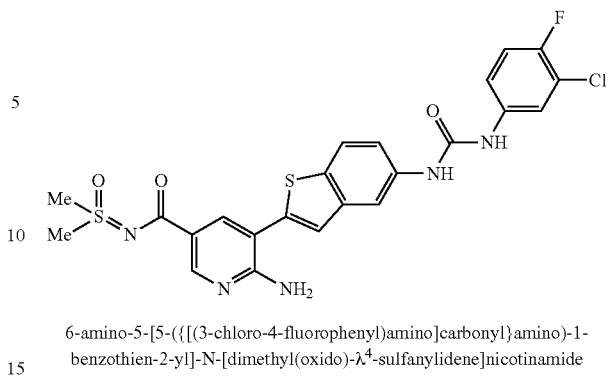

6-amino-5-[5-({[(3-chloro-4-fluorophenyl)amino]carbonyl}amino)-1-benzothien-2-yl]-N-[dimethyl(oxido)-λ⁴-sulfanylidene]nicotinamide Example 2

In a manner similar to that described in Example 1, 6-amino-5-(5-amino-1-benzothien-2-yl)-N-[dimethyl(oxido)-λ⁴-sulfanylidene]nicotinamide and 2-chloro-1-fluoro-4-isocyanatobenzene were converted to the title compound.

¹H NMR (DMSO-d₆) δ: 8.91 (d, J=4.7 Hz, 2H), 8.61 (d, J=2.3 Hz, 1H), 8.08 (d, J=2.1 Hz, 1H), 8.02 (d, J=2.3 Hz, 1H), 7.88 (d, J=8.5 Hz, 1H), 7.83 (dd, J=6.7, 2.1 Hz, 1H), 7.59 (s, 1H), 7.38 (dd, J=8.8, 2.1 Hz, 1H), 7.32-7.35 (m, 2H), 6.75 (s, 2H), 3.44 (s, 6H).

Example 3

6-amino-N-[dimethyl(oxido)-λ⁴-sulfanylidene]-5-[5-({[(2-fluoro-5-methylphenyl)amino]carbonyl}amino)-1-benzothien-2-yl]nicotinamide In a manner similar to that described in Example 1, 6-amino-5-(5-amino-1-benzothien-2-yl)-N-[dimethyl(oxido)-λ⁴-sulfanylidene]nicotinamide and 1-fluoro-2-isocyanato-4-methylbenzene were converted to the title compound.

¹H NMR (DMSO-d₆) δ: 9.18 (s, 1H), 8.61 (d, J=2.1 Hz, 1H), 8.50 (d, J=2.6 Hz, 1H), 8.12 (d, J=2.1 Hz, 1H), 8.01-8.04 (m, 2H), 7.89 (d, J=8.8 Hz, 1H), 7.60 (s, 1H), 7.35 (dd, J=8.5, 2.1 Hz, 1H), 7.11 (dd, J=11.3, 8.4 Hz, 1H), 6.79-6.82 (m, 1H), 6.75 (s, 2H), 3.44 (s, 6H), 2.28 (s, 3H).

Hz, 1H), 8.02 (d, J=2.1 Hz, 1H), 7.89 (d, J=8.8 Hz, 1H), 7.60-7.67 (m, 3H), 7.39 (dd, J=8.8, 2.1 Hz, 1H), 6.76 (s, 2H), 3.44 (s, 6H).

Example 4

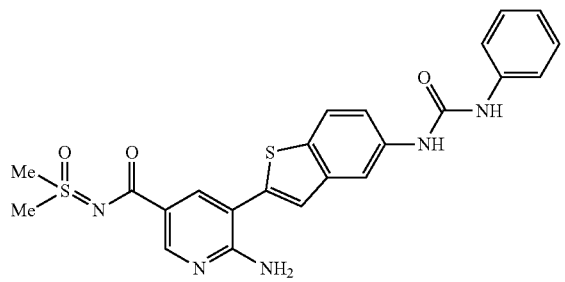

6-amino-5-{5-[(anilinocarbonyl)amino]-1-benzothien-2-yl}-N-[dimethyl(oxido)-λ⁴-sulfanlidene]nicotinamide

Example 6

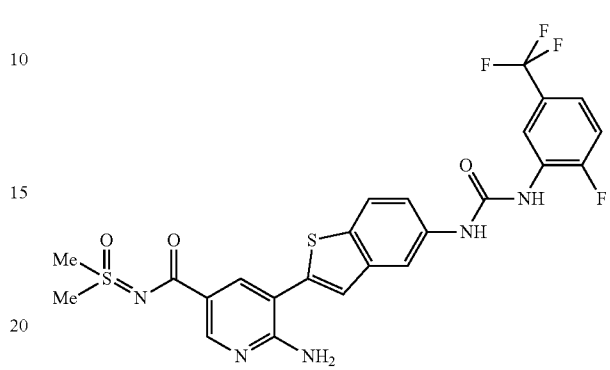

6-amino-N-[dimethyl(oxido)-λ⁴-sulfanylidene]-5-{5-[({[2-fluoro-5-(trifluoromethyl)phenyl]amino}carbonyl)amino]-1-benzothien-2-yl}nicotinamide In a manner similar to that described in Example 1, 6-amino-5-(5-amino-1-benzothien-2-yl)-N-[dimethyl(oxido)-λ⁴-sulfanylidene]nicotinamide and isocyanatobenzene were converted to the title compound.

$^1$H NMR (DMSO-d$_6$) δ: 8.80 (s, 1H), 8.69 (s, 1H), 8.60 (d, J=2.3 Hz, 1H), 8.10 (d, J=2.1 Hz, 1H), 8.02 (d, J=2.3 Hz, 1H), 7.87 (d, J=8.8 Hz, 1H), 7.60 (s, 1H), 7.48 (dd, J=8.5, 0.9 Hz, 2H), 7.37 (dd, J=8.5, 2.1 Hz, 1H), 7.29 (dd, J=8.2, 7.6 Hz, 2H), 6.96-6.99 (m, 1H), 6.75 (s, 2H), 3.44 (s, 6H)

In a manner similar to that described in Example 1, 6-amino-5-(5-amino-1-benzothien-2-yl)-N-[dimethyl(oxido)-λ⁴-sulfanylidene]nicotinamide and 1-fluoro-2-isocyanato-4-(trifluoromethyl)benzene were converted to the title compound.

$^1$H NMR (DMSO-d$_6$) δ: 9.31 (s, 1H), 8.93 (d, J=2.6 Hz, 1H), 8.67 (dd, J=7.3, 2.1 Hz, 1H), 8.61 (d, J=2.1 Hz, 1H), 8.15 (d, J=2.1 Hz, 1H), 8.03 (d, J=2.1 Hz, 1H), 7.91 (d, J=8.5 Hz, 1H), 7.62 (s, 1H), 7.51 (dd, J=10.6, 8.8 Hz, 1H), 7.38-7.41 (m, 1H), 7.36 (dd, J=8.5, 2.1 Hz, 1H), 6.77 (s, 2H), 3.44 (s, 6H).

Example 5

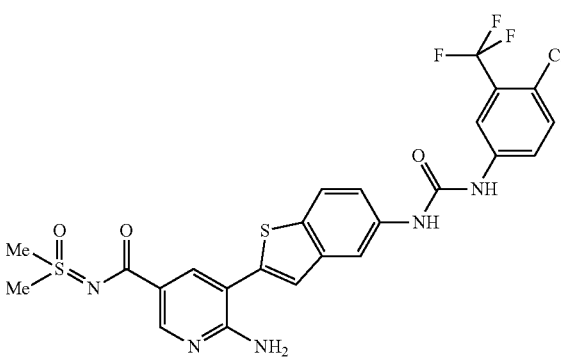

6-amino-5-{5-[({[4-chloro-3-(trifluoromethyl)phenyl]amino}carbonyl)amino]-1-benzothien-2-yl}-N-[dimethyl(oxido)-λ⁴-sulfanylidene]nicotinamide

Example 7

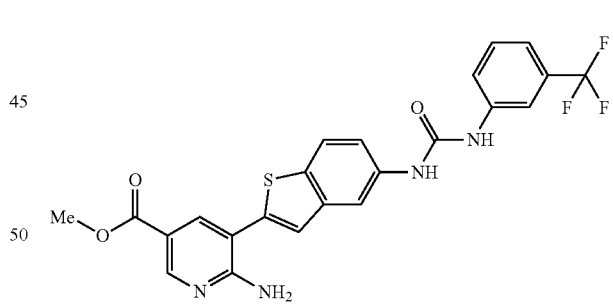

methyl 6-amino-5-{5-[({[3-(trifluoromethyl)phenyl]amino}carbonyl)amino]-1-benzothien-2-yl}nicotinate In a manner similar to that described in Example 1, 6-amino-5-(5-amino-1-benzothien-2-yl)-N-[dimethyl(oxido)-λ⁴-sulfanylidene]nicotinamide and 1-chloro-4-isocyanato-2-(trifluoromethyl)benzene were converted to the title compound.

$^1$H NMR (DMSO-d$_6$) δ: 9.30 (br. s., 1H), 9.08 (br. s., 1H), 8.61 (d, J=2.1 Hz, 1H), 8.16 (d, J=2.3 Hz, 1H), 8.11 (d, J=1.8

In a manner similar to that described in Example 11, methyl 6-amino-5-(5-amino-1-benzothien-2-yl)nicotinate and 1-isocyanato-3-(trifluoromethyl)benzene were converted to the title compound.

$^1$H NMR (DMSO-d$_6$) δ: 9.08 (s, 1H), 8.94 (s, 1H), 8.57 (d, J=2.3 Hz, 1H), 8.13 (d, J=2.1 Hz, 1H), 8.06 (t, J=1.5 Hz, 1H), 7.94 (d, J=2.3 Hz, 1H), 7.90 (d, J=8.5 Hz, 1H), 7.63 (s, 1H), 7.59 (d, J=8.8 Hz, 1H), 7.52 (t, J=7.9 Hz, 1H), 7.40 (dd, J=8.5, 2.1 Hz, 1H), 7.32 (d, J=7.6 Hz, 1H), 7.01 (br. s., 2H), 3.81 (s, 3H).

Example 8

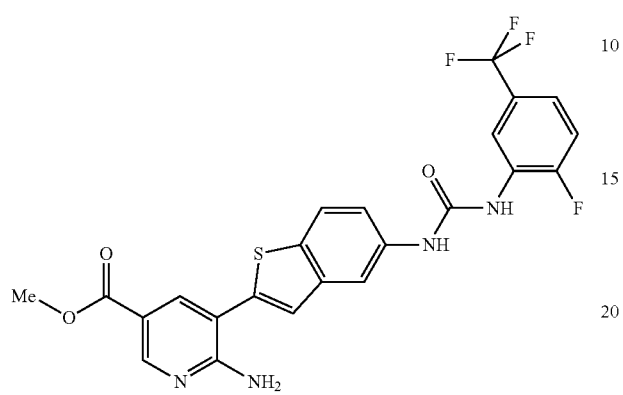

methyl 6-amino-5-{5-[({[2-fluoro-5-(trifluoromethyl)phenyl]amino}carbonyl)amino]-1-benzothien-2-yl}nicotinate In a manner similar to that described in Example 11, methyl 6-amino-5-(5-amino-1-benzothien-2-yl)nicotinate and 1-fluoro-2-isocyanato-4-(trifluoromethyl)benzene were converted to the title compound.

$^1$H NMR (DMSO-d$_6$) δ: 9.31 (s, 1H), 8.93 (d, J=2.6 Hz, 1H), 8.67 (dd, J=7.3, 2.1 Hz, 1H), 8.58 (d, J=2.1 Hz, 1H), 8.16 (d, J=2.1 Hz, 1H), 7.94 (d, J=2.3 Hz, 1H), 7.91 (d, J=8.8 Hz, 1H), 7.65 (s, 1H), 7.51 (dd, J=10.7, 8.9 Hz, 1H), 7.38-7.42 (m, 1H), 7.37 (dd, J=8.7, 2.2 Hz, 1H), 7.02 (br. s., 2H), 3.81 (s, 3H).

Example 9

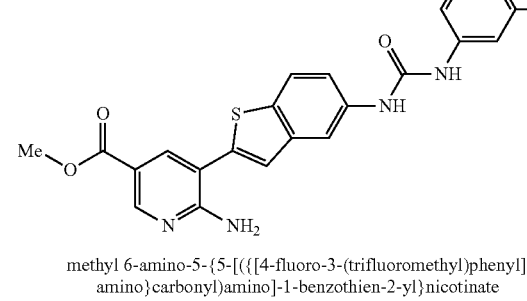

methyl 6-amino-5-{5-[({[4-fluoro-3-(trifluoromethyl)phenyl]amino}carbonyl)amino]-1-benzothien-2-yl}nicotinate In a manner similar to that described in Example 11, methyl 6-amino-5-(5-amino-1-benzothien-2-yl)nicotinate and 1-chloro-4-isocyanato-2-(trifluoromethyl)benzene were converted to the title compound.

$^1$H NMR (DMSO-d$_6$) δ: 9.20 (s, 1H), 9.00 (s, 1H), 8.57 (d, J=2.3 Hz, 1H), 8.16 (d, J=2.3 Hz, 1H), 8.12 (d, J=2.1 Hz, 1H), 7.94 (d, J=2.3 Hz, 1H), 7.90 (d, J=8.8 Hz, 1H), 7.61-7.67 (m, 3H), 7.40 (dd, J=8.5, 2.1 Hz, 1H), 7.01 (br. s., 2H), 3.81 (s, 3H).

Example 10

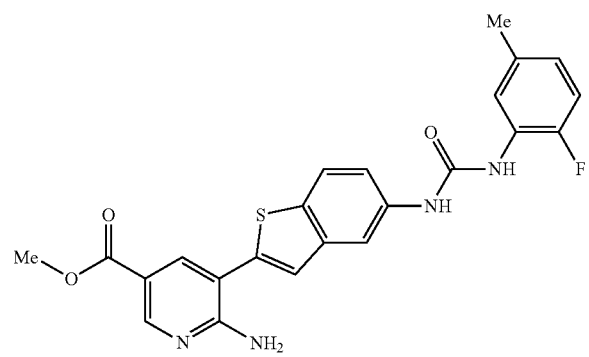

methyl 6-amino-5-[5-({[(2-fluoro-5-methylphenyl)amino]carbonyl}amino)-1-benzothien-2-yl]nicotinate In a manner similar to that described in Example 11, methyl 6-amino-5-(5-amino-1-benzothien-2-yl)nicotinate and 1-fluoro-2-isocyanato-4-methylbenzene were converted to the title compound.

$^1$H NMR (DMSO-d$_6$) δ: 9.19 (s, 1H), 8.57 (d, J=2.1 Hz, 1H), 8.50 (d, J=2.6 Hz, 1H), 8.13 (d, J=2.1 Hz, 1H), 8.03 (dd, J=7.9, 1.8 Hz, 1H), 7.94 (d, J=2.1 Hz, 1H), 7.89 (d, J=8.8 Hz, 1H), 7.62 (s, 1H), 7.36 (dd, J=8.5, 2.1 Hz, 1H), 7.11 (dd, J=11.3, 8.4 Hz, 1H), 7.01 (br. s., 2H), 6.79-6.82 (m, 1H), 3.81 (s, 3H), 2.28 (s, 3H)

Preparation 3

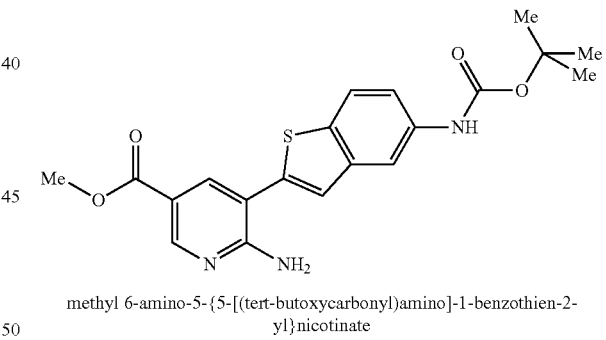

methyl 6-amino-5-{5-[(tert-butoxycarbonyl)amino]-1-benzothien-2-yl}nicotinate

To the degassed mixture of methyl 6-amino-5-iodonicotinate (4.17 g, 15 mmol, 1 eq), {[2-(4,4,5,5-tetramethyl-[1,3,2]dioxaborolan-2-yl)-benzo[b]thiophen-5-yl]-carbamic acid tert-butyl ester} (6.47 g, 1.15 eq), and aq sodium carbonate (2M, 22.5 mL, 3 eq) in dioxane (30 mL) was added Ph$_3$P (393 mg, 0.1 eq) and Pd(OAc)$_2$ (340 mg, 0.1 eq). The mixture was heated to 50° C. with vigorous stirring for 45 minutes. The reaction mixture was then partitioned between aq NH$_4$Cl and EtOAc. The organic layer was isolated, washed with sat aq NaHCO$_3$, brine, and finally dried with anhydrous sodium sulfate. The upper solution-layer was decanted, concentrated, and the solid residue was treated with EtOAc-Hex (1:4) with stirring at room temperature for 3 hours. methyl 6-amino-5-{5-[(tert-butoxycarbonyl)amino]-1-benzothien-2-yl}nicotinate was obtained upon filtration as a slightly green-yellowish solid.

¹H NMR (DMSO-d₆) δ: 9.48 (br. s., 1H), 8.56 (d, J=2.1 Hz, 1H), 8.08 (br. s., 1H), 7.93 (d, J=2.3 Hz, 1H), 7.84 (d, J=8.5 Hz, 1H), 7.59 (s, 1H), 7.41 (dd, J=8.8, 2.1 Hz, 1H), 7.00 (br. s., 2H), 3.81 (s, 3H), 1.50 (s, 9H)

Preparation 4

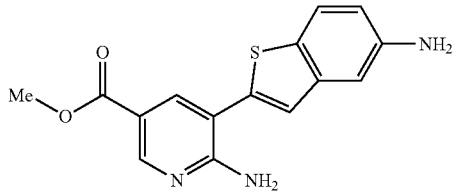

methyl 6-amino-5-(5-amino-1-benzothien-2-yl)nicotinate

To the above obtained crude solid of methyl 6-amino-5-{5-[(tert-butoxycarbonyl)amino]-1-benzothien-2-yl}nicotinate (15 mmol, 1 eq) in dichloromethane (25 mL) at 0° C. was added dropwise trifluoroacetic acid (11.7 mL, 10 eq). During this process the reaction mixture became a brown solution. After the reaction was stirred at 0° C. for 10 minutes and at room temperature for 5 hours, it was slowly poured into an ice-cooled saturated aqueous sodium bicarbonate solution with stirring. When all the bubbling ceased, the mixture was extracted with dichloromethane, which was washed with brine and dried with anhydrous sodium sulfate. The upper brown solution was decanted, concentrated to a lesser amount, and the occurring solid mixture was treated with EtOAc-Hex (1:1). A green-yellowish solid was obtained upon filtration which was further subject to chromatography (MeOH-DCM 1:100 to 1:20). The corresponding product fractions were collected, concentrated, and triturated with EtOAc-Hex (1:4) giving methyl 6-amino-5-(5-amino-1-benzothien-2-yl)nicotinate as a slightly yellow solid in amount of 3.48 g upon filtration with a yield of 78% for two steps.

¹H NMR (DMSO-d₆) δ: 8.54 (d, J=2.1 Hz, 1H), 7.91 (d, J=2.1 Hz, 1H), 7.58 (d, J=8.5 Hz, 1H), 7.40 (s, 1H), 6.97 (d, J=2.1 Hz, 1H), 6.94 (br. s., 2H), 6.74 (dd, J=8.5, 2.1 Hz, 1H), 5.13 (s, 2H), 3.80 (s, 3H)

Example 11

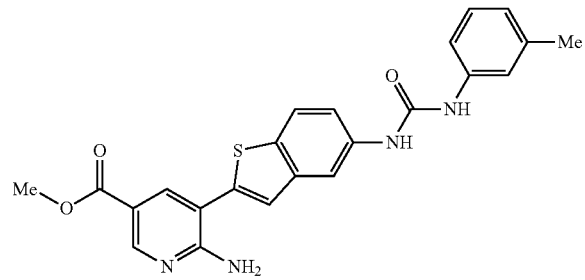

methyl 6-amino-5-[5-({[(3-methylphenyl)amino]carbonyl}amino)-1-benzothein-2-yl]nicotinate To the solution of methyl 6-amino-5-(5-amino-1-benzothien-2-yl)nicotinate (120 mg, 0.4 mmol. 1 eq) in anhydrous THF (4 mL) at room temperature was added dropwise m-tolylisocyanate (0.051 mL, 1 eq). After the reaction was stirred at room temperature for 4 hours, the solid appeared in the reaction was directly filtered to give methyl 6-amino-5-[5-({[(3-methylphenyl)amino]carbonyl}amino)-1-benzothien-2-yl]nicotinate as a white solid in amount of 84 mg.

¹H NMR (DMSO-d₆) δ: 8.78 (s, 1H), 8.61 (s, 1H), 8.57 (d, J=2.1 Hz, 1H), 8.11 (d, J=2.1 Hz, 1H), 7.94 (d, J=2.3 Hz, 1H), 7.88 (d, J=8.8 Hz, 1H), 7.61 (s, 1H), 7.38 (dd, J=8.7, 2.2 Hz, 1H), 7.32 (s, 1H), 7.25 (d, J=8.2 Hz, 1H), 7.16 (t, J=7.8 Hz, 1H), 7.01 (br. s., 2H), 6.80 (d, J=7.3 Hz, 1H), 3.81 (s, 3H), 2.29 (s, 3H).

Example 12

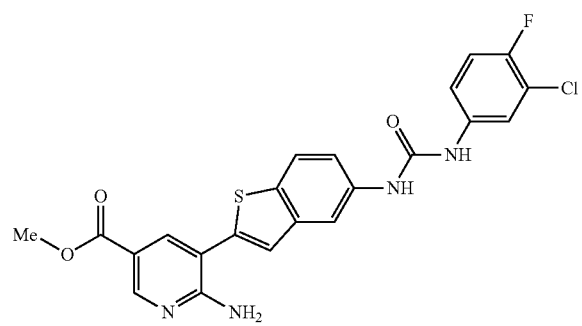

methyl 6-amino-5-[5-({[(3-chloro-4-fluorophenyl)amino]carbonyl}amino)-1-benzothien-2-yl]nicotinate In a manner similar to that described in Example 11, methyl 6-amino-5-(5-amino-1-benzothien-2-yl)nicotinate and 2-chloro-1-fluoro-4-isocyanatobenzene are converted to the title compound.

¹H NMR (DMSO-d₆) δ: 8.90 (s, 1H), 8.90 (s, 1H), 8.57 (d, J=2.3 Hz, 1H), 8.09 (d, J=2.1 Hz, 1H), 7.94 (d, J=2.1 Hz, 1H), 7.89 (d, J=8.5 Hz, 1H), 7.83 (dd, J=6.9, 1.9 Hz, 1H), 7.62 (s, 1H), 7.39 (dd, J=8.8, 2.1 Hz, 1H), 7.31-7.35 (m, 2H), 7.01 (br. s., 2H), 3.81 (s, 3H).

Example 13

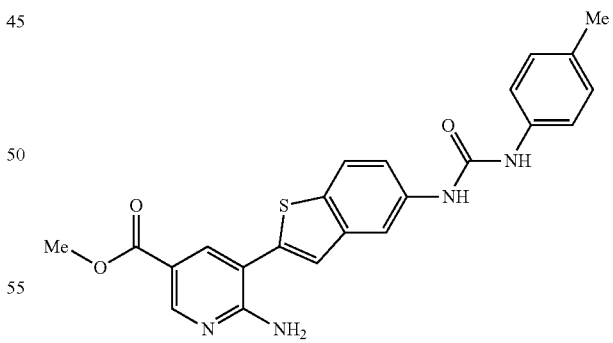

methyl 6-amino-5-[5-({[(4-methylphenyl)amino]carbonyl}amino)-1-benzothien-2-yl]nicotinate In a manner similar to that described in Example 11, methyl 6-amino-5-(5-amino-1-benzothien-2-yl)nicotinate and 1-isocyanato-4-methylbenzene are converted to the title compound.

¹H NMR (DMSO-d₆) δ: 8.75 (s, 1H), 8.57 (d, J=2.1 Hz, 2H), 8.09 (d, J=2.1 Hz, 1H), 7.94 (d, J=2.3 Hz, 1H), 7.87 (d,

J=8.8 Hz, 1H), 7.61 (s, 1H), 7.34-7.39 (m, 3H), 7.09 (d, J=8.2 Hz, 2H), 7.01 (br. s., 2H), 3.81 (s, 3H), 2.25 (s, 3H).

Example 14

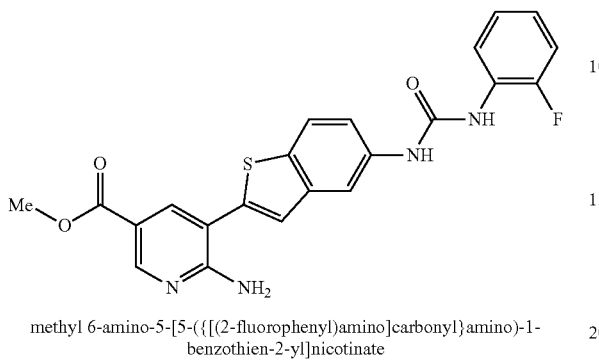

methyl 6-amino-5-[5-({[(2-fluorophenyl)amino]carbonyl}amino)-1-benzothien-2-yl]nicotinate In a manner similar to that described in Example 11, methyl 6-amino-5-(5-amino-1-benzothien-2-yl)nicotinate and 1-fluoro-2-isocyanatobenzene are converted to the title compound.

$^1$H NMR (DMSO-d$_6$) δ: 9.21 (s, 1H), 8.57-8.59 (m, 2H), 8.19 (td, J=8.3, 1.6 Hz, 1H), 8.12 (d, J=2.1 Hz, 1H), 7.94 (d, J=2.1 Hz, 1H), 7.90 (d, J=8.5 Hz, 1H), 7.63 (s, 1H), 7.37 (dd, J=8.8, 2.1 Hz, 1H), 7.25 (ddd, J=11.7, 8.1, 1.3 Hz, 1H), 7.15 (t, J=7.8 Hz, 1H), 6.99-7.04 (m, 3H), 3.81 (s, 3H).

Example 15

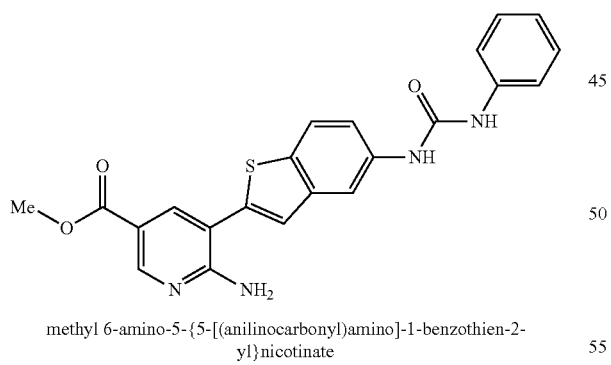

methyl 6-amino-5-{5-[(anilinocarbonyl)amino]-1-benzothien-2-yl}nicotinate

In a manner similar to that described in Example 11, methyl 6-amino-5-(5-amino-1-benzothien-2-yl)nicotinate and isocyanatobenzene are converted to the title compound.

$^1$H NMR (DMSO-d$_6$): 8.81 (s, 1H), 8.69 (s, 1H), 8.57 (d, J=2.3 Hz, 1H), 8.11 (d, J=2.1 Hz, 1H), 7.94 (d, J=2.3 Hz, 1H), 7.88 (d, J=8.5 Hz, 1H), 7.62 (s, 1H), 7.46-7.49 (m, 2H), 7.38 (dd, J=8.5, 2.1 Hz, 1H), 7.27-7.31 (m, 2H), 7.01 (br. s., 2H), 6.98 (tt, J=7.3, 1.0 Hz, 1H), 3.81 (s, 3H).

Example 16

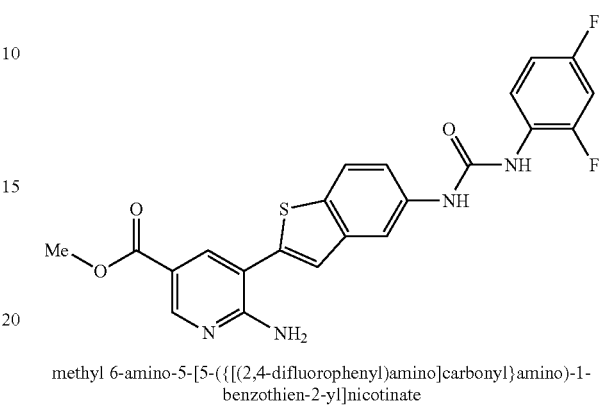

methyl 6-amino-5-[5-({[(2,4-difluorophenyl)amino]carbonyl}amino)-1-benzothien-2-yl]nicotinate In a manner similar to that described in Example 11, methyl 6-amino-5-(5-amino-1-benzothien-2-yl)nicotinate and 2,4-difluoro-1-isocyanatobenzene are converted to the title compound.

$^1$H NMR (DMSO-d$_6$) δ: 9.15 (s, 1H), 8.57 (d, J=2.3 Hz, 1H), 8.53 (d, J=2.1 Hz, 1H), 8.09-8.14 (m, 2H), 7.94 (d, J=2.1 Hz, 1H), 7.89 (d, J=8.5 Hz, 1H), 7.63 (s, 1H), 7.37 (dd, J=8.5, 2.1 Hz, 1H), 7.32 (ddd, J=11.5, 8.7, 2.9 Hz, 1H), 7.04-7.08 (m, 1H), 7.01 (br. s., 2H), 3.81 (s, 3H).

Example 17

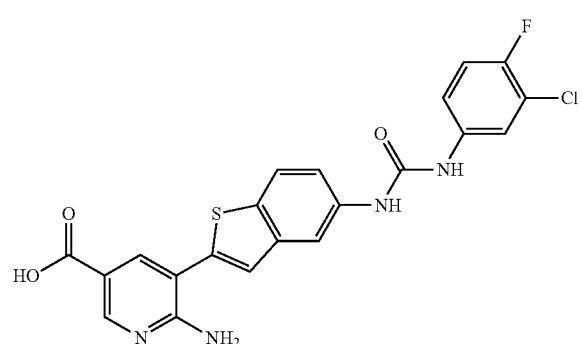

6-amino-5-[5-({[(3-chloro-4-fluorophenyl)amino]carbonyl}amino)-1-benzothien-2-yl]nicotinic acid In a manner similar to that described in Example 19, methyl 6-amino-5-[5-({[(3-chloro-4-fluorophenyl)amino] carbonyl}amino)-1-benzothien-2-yl]nicotinate was converted to the title compound.

$^1$H NMR (DMSO-d$_6$) δ: 12.65 (br. s., 1H), 8.96 (d, J=3.5 Hz, 2H), 8.55 (d, J=2.3 Hz, 1H), 8.09 (d, J=2.1 Hz, 1H), 7.95

(d, J=2.3 Hz, 1H), 7.89 (d, J=8.8 Hz, 1H), 7.80-7.86 (m, 1H), 7.62 (s, 1H), 7.39 (dd, J=8.8, 2.1 Hz, 1H), 7.30-7.36 (m, 2H), 6.99 (br. s., 2H).

Example 18

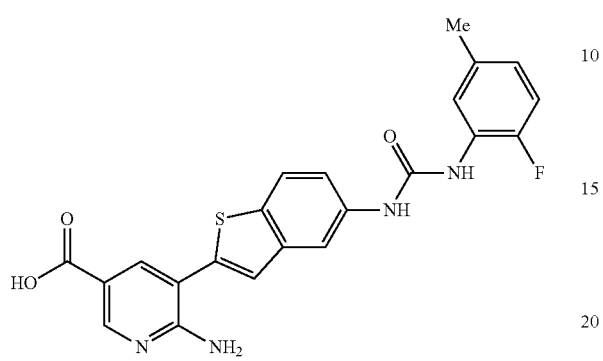

6-amino-5-[5-({[(2-fluoro-5-methylphenyl)amino]carbonyl}amino)-1-benzothien-2-yl]nicotinic acid In a manner similar to that described in Example 19, methyl 6-amino-5-[5-({[(2-fluoro-5-methylphenyl)amino]carbonyl}amino)-1-benzothien-2-yl]nicotinate was converted to the title compound.

$^1$H NMR (DMSO-$d_6$) δ: 12.73 (br. s., 1H), 9.27 (s, 1H), 8.51-8.58 (m, 2H), 8.14 (d, J=2.1 Hz, 1H), 8.02 (dd, J=7.9, 1.8 Hz, 1H), 7.97 (d, J=2.1 Hz, 1H), 7.90 (d, J=8.5 Hz, 1H), 7.63 (s, 1H), 7.37 (dd, J=8.6, 2.2 Hz, 1H), 7.04-7.20 (m, 3H), 6.80 (ddd, J=7.7, 5.2, 2.1 Hz, 1H), 2.28 (s, 3H)

Example 19

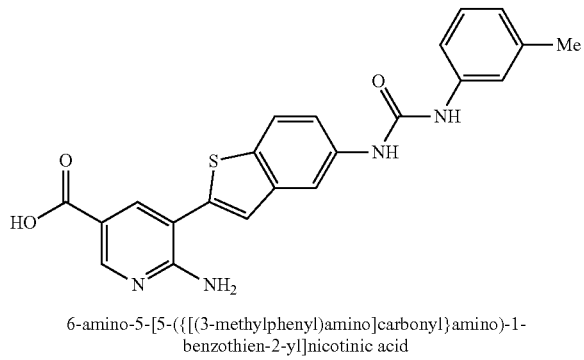 [SMILES: Cc1cccc(NC(=O)Nc2ccc3sc(-c4cc(C(=O)O)cnc4N)cc3c2)c1]

6-amino-5-[5-({[(3-methylphenyl)amino]carbonyl}amino)-1-benzothien-2-yl]nicotinic acid To the stirring mixture of methyl 6-amino-5-[5-({[(3-methylphenyl)amino]carbonyl}amino)-1-benzothien-2-yl]nicotinate (420 mg, 0.972 mmol, 1 eq) in MeOH—H$_2$O (3:1, 20 mL) at room temperature was added potassium hydroxide pellets (272 mg, 5 eq) and the reaction mixture was stirred at 65° C. for total of two hours, at which time the reaction mixture became a clear yellow solution. The solution was concentrated under reduced pressure to remove most part of methanol. The mixture was then cooled in an ice-bath, concentrated hydrochloride was added dropwise, and the pH was adjusted to about 3. After the mixture was stirred for about another 30 minutes, it was filtered through a Buchner funnel, rinsed with water, and 6-amino-5-[5-({[(3-methylphenyl)amino]carbonyl}amino)-1-benzothien-2-yl]nicotinic acid was obtained as a yellow solid in quantitative yield.

$^1$H NMR (DMSO-$d_6$) δ: 9.09 (s, 1H), 8.88 (s, 1H), 8.55 (d, J=2.1 Hz, 1H), 8.14 (d, J=2.1 Hz, 1H), 8.01 (d, J=2.1 Hz, 1H), 7.89 (d, J=8.8 Hz, 1H), 7.63 (s, 1H), 7.29-7.45 (m, 4H), 7.26 (d, J=8.2 Hz, 1H), 7.12-7.19 (m, 1H), 6.79 (d, J=7.3 Hz, 1H), 2.28 (s, 3H)

Example 20

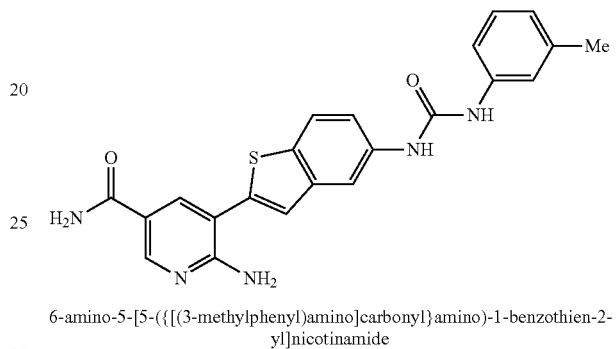

6-amino-5-[5-({[(3-methylphenyl)amino]carbonyl}amino)-1-benzothien-2-yl]nicotinamide To a seal tube containing 6-amino-5-[5-({[(3-methylphenyl)amino]carbonyl}amino)-1-benzothien-2-yl]nicotinic (84 mg, 0.2 mmol, 1 eq), DMAP (5 mg, 0.2 eq), and EDCI (46.1 mg, 1.2 eq) in anhydrous THF (3 mL) at room temperature, gaseous ammonia was bubbled through for about 5 minutes. The tube was quickly capped and the reaction was heated at 60° C. for one hour.

TLC indicated the reaction did not proceed.

After the reaction was cooled to room temperature, to the reaction mixture was added anhydrous DMF (3 mL), diisopropylethylamine (0.2 mL, 5 eq), ammonium chloride (32.1 mg, 3 eq), and (benzotriazol-1-yloxy)tris(dimethylamino)phosphonium hexafluorophosphate (97.3 mg, 1.1 eq). After the reaction was stirred at 60° C. for 30 minutes, it was partitioned between ethyl acetate and aqueous ammonium chloride. The organic layer was isolated, washed with saturated aqueous sodium bicarbonate, brine, and dried with anhydrous sodium sulfate. The clear solution was decanted, concentrated, the solid residue was subject to a gradient column chromatography (from DCM to MeOH-DCM 1:1). 6-amino-5-[5-({[(3-methylphenyl)amino]carbonyl}amino)-1-benzothien-2-yl]nicotinamide was obtained as white solid in two portions, 38 mg from the chromatography fractions and 16 mg from a remainder on top of the syringe column. Both were confirmed by proton NMR.

$^1$H NMR (DMSO-$d_6$) δ: 8.81 (s, 1H), 8.63 (s, 1H), 8.55 (d, J=2.1 Hz, 1H), 8.08 (d, J=1.8 Hz, 1H), 8.03 (d, J=2.3 Hz, 1H), 7.95-6.88 (br. s., 2H), 7.86 (d, J=8.5 Hz, 1H), 7.59 (s, 1H), 7.39 (dd, J=8.8, 2.1 Hz, 1H), 7.32 (s, 1H), 7.23-7.29 (m, 1H), 7.13-7.19 (m, 1H), 6.80 (d, J=7.3 Hz, 1H), 6.48 (s, 2H), 2.29 (s, 3H).

Example 21

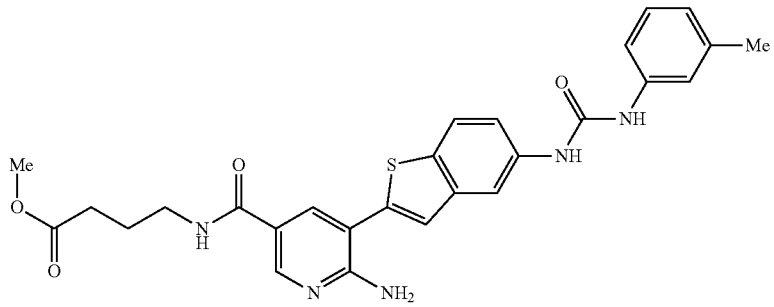

methyl 4-[({6-amino-5-[5-({[(3-methylphenyl)amino]carbonyl}amino)-1-benzothien-2-yl]pyridin-3-yl}carbonyl)amino]butanoate In a manner similar to that described in Example 22, 6-amino-5-[5-({[(3-methylphenyl)amino]carbonyl}amino)-1-benzothien-2-yl]nicotinic acid was converted to the title compound.

$^1$H NMR (DMSO-d$_6$) δ: 8.80 (s, 1H), 8.62 (s, 1H), 8.52 (d, J=2.3 Hz, 1H), 8.33 (t, J=5.6 Hz, 1H), 8.10 (d, J=2.1 Hz, 1H), 8.01 (d, J=2.3 Hz, 1H), 7.88 (d, J=8.8 Hz, 1H), 7.60 (s, 1H), 7.37 (dd, J=8.8, 2.1 Hz, 1H), 7.32 (s, 1H), 7.22-7.28 (m, 1H), 7.13-7.20 (m, 1H), 6.80 (d, J=7.6 Hz, 1H), 6.61 (s, 2H), 3.58 (s, 3H), 3.21-3.30 (m, 2H), 2.37 (t, J=7.3 Hz, 2H), 2.29 (s, 3H), 1.77 (quin, J=7.1 Hz, 2H)

Example 22

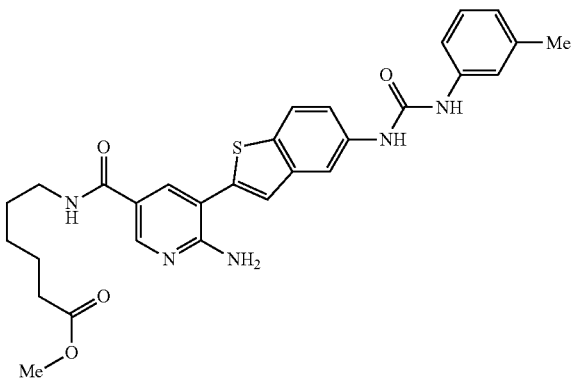

methyl 6-[({6-amino-5-[5-({[(3-methylphenyl)amino]carbonyl}amino)-1-benzothien-2-yl]pyridin-3-yl}carbonyl)amino]hexanoate The reaction mixture of 6-amino-5-[5-({[(3-methylphenyl)amino]carbonyl}amino)-1-benzothien-2-yl]nicotinic acid (84 mg, 0.2 mmol, 1 eq), methyl 6-aminohexanoate hydrochloride (43.7 mg, 1.2 eq), DMAP (5 mg, 0.2 eq), and EDCI (46.1 mg, 1.2 eq) in anhydrous 1,2-dichloroethane (3 mL) was stirred and heated at 50° C. for 2 hours. It was then diluted with ethyl acetate, washed sequentially with aqueous NH$_4$Cl, saturated aqueous NaHCO$_3$, and brine, and dried with anhydrous sodium sulfate. The upper clear solution was decanted, concentrated, and the solid residue was triturated with EtOAc-Hex (3:1) yielding methyl 6-[({6-amino-5-[5-({[(3-methylphenyl)amino]carbonyl}amino)-1-benzothien-2-yl]pyridin-3-yl}carbonyl)amino]hexanoate as a white solid in amount of 83 mg.

$^1$H NMR (DMSO-d$_6$) δ: 8.79 (s, 1H), 8.62 (s, 1H), 8.51 (d, J=2.3 Hz, 1H), 8.29 (t, J=5.6 Hz, 1H), 8.10 (d, J=1.8 Hz, 1H), 8.00 (d, J=2.3 Hz, 1H), 7.88 (d, J=8.5 Hz, 1H), 7.60 (s, 1H), 7.37 (dd, J=8.8, 2.1 Hz, 1H), 7.32 (s, 1H), 7.22-7.28 (m, 1H), 7.13-7.20 (m, 1H), 6.80 (d, J=7.3 Hz, 1H), 6.60 (s, 2H), 3.57 (s, 3H), 3.22 (q, J=6.4 Hz, 2H), 2.26-2.35 (m, 5H), 1.53 (tt, J=14.5, 7.3 Hz, 4H), 1.26-1.36 (m, 2H).

Example 23

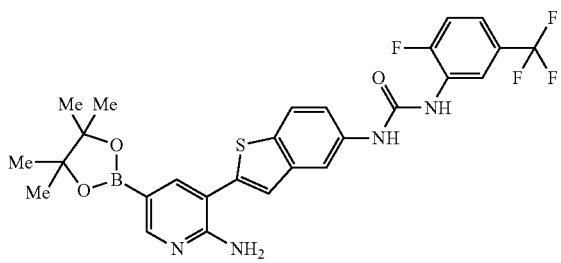

1-{2-[2-amino-5-(4,4,5,5-tetramethyl-1,3,2-dioxaborolan-2-yl)pyridin-3-yl]-1-benzothien-5-yl}-3-[2-fluoro-5-(trifluoromethyl)phenyl]urea In a manner similar to that described in Example 29, 3-(5-amino-1-benzothien-2-yl)-5-(4,4,5,5-tetramethyl-1,3,2-dioxaborolan-2-yl)pyridin-2-amine and 1-fluoro-2-isocyanato-4-(trifluoromethyl)benzene are converted to the title compound.

$^1$H NMR (DMSO-d$_6$) δ: 9.30 (s, 1H), 8.92 (d, J=2.6 Hz, 1H), 8.67 (dd, J=7.3, 2.1 Hz, 1H), 8.24 (d, J=1.8 Hz, 1H), 8.12 (d, J=1.8 Hz, 1H), 7.89 (d, J=8.5 Hz, 1H), 7.69 (d, J=1.8 Hz, 1H), 7.61 (s, 1H), 7.46-7.55 (m, 1H), 7.33-7.43 (m, 2H), 6.53 (s, 2H), 1.28 (s, 12H).

Example 24

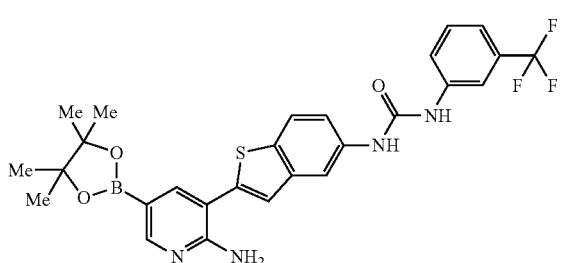

1-{2-[2-amino-5-(4,4,5,5-tetramethyl-1,3,2-dioxaborolan-2-yl)pyridin-3-yl]-1-benzothien-5-yl}-3-[3-(trifluoromethyl)phenyl]urea In a manner similar to that described in Example 29, 3-(5-amino-1-benzothien-2-yl)-5-(4,4,5,5-tetramethyl-1,3,2-dioxaborolan-2-yl)pyridin-2-amine and 1-isocyanato-3-(trifluoromethyl)benzene are converted to the title compound.

¹H NMR (DMSO-d₆) δ: 9.07 (s, 1H), 8.92 (s, 1H), 8.24 (d, J=1.8 Hz, 1H), 8.09 (d, J=1.8 Hz, 1H), 8.06 (s, 1H), 7.87 (d, J=8.8 Hz, 1H), 7.69 (d, J=1.8 Hz, 1H), 7.56-7.62 (m, 2H), 7.48-7.55 (m, 1H), 7.39 (dd, J=8.6, 2.2 Hz, 1H), 7.31 (d, J=7.6 Hz, 1H), 6.53 (s, 2H), 1.28 (s, 12H)

Example 25

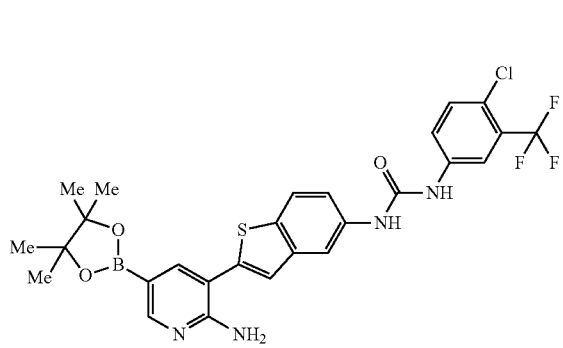

1-{2-[2-amino-5-(4,4,5,5-tetramethyl-1,3,2-dioxaborolan-2-yl)pyridin-3-yl]-1-benzothien-5-yl}-3-[4-chloro-3-(trifluoromethyl)phenyl]urea In a manner similar to that described in Example 29, 3-(5-amino-1-benzothien-2-yl)-5-(4,4,5,5-tetramethyl-1,3,2-dioxaborolan-2-yl)pyridin-2-amine and 1-chloro-4-isocyanato-2-(trifluoromethyl)benzene are converted to the title compound.

¹H NMR (DMSO-d₆) δ: 9.19 (s, 1H), 8.98 (s, 1H), 8.24 (d, J=1.8 Hz, 1H), 8.16 (d, J=2.1 Hz, 1H), 8.08 (d, J=2.1 Hz, 1H), 7.87 (d, J=8.5 Hz, 1H), 7.69 (d, J=1.8 Hz, 1H), 7.62-7.66 (m, 2H), 7.59 (s, 1H), 7.39 (dd, J=8.5, 2.1 Hz, 1H), 6.53 (s, 2H), 1.28 (s, 12H)

Example 26

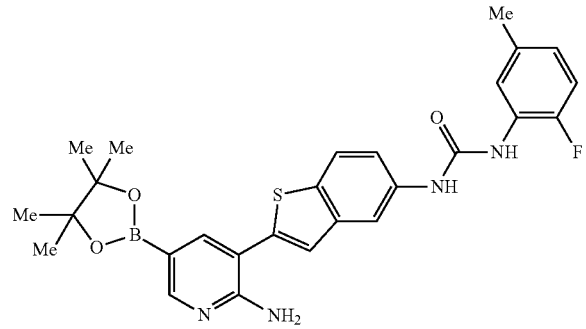

1-{2-[2-amino-5-(4,4,5,5-tetramethyl-1,3,2-dioxaborolan-2-yl)pyridin-3-yl]-1-benzothien-5-yl}-3-(2-fluoro-5-methylphenyl)urea In a manner similar to that described in Example 29, 3-(5-amino-1-benzothien-2-yl)-5-(4,4,5,5-tetramethyl-1,3,2-dioxaborolan-2-yl)pyridin-2-amine and 1-fluoro-2-isocyanato-4-methylbenzene are converted to the title compound.

¹H NMR (DMSO-d₆) δ: 9.18 (s, 1H), 8.50 (d, J=2.6 Hz, 1H), 8.24 (d, J=1.8 Hz, 1H), 8.09 (d, J=2.1 Hz, 1H), 8.03 (dd, J=7.9, 1.8 Hz, 1H), 7.87 (d, J=8.8 Hz, 1H), 7.69 (d, J=1.8 Hz, 1H), 7.58 (s, 1H), 7.36 (dd, J=8.8, 2.1 Hz, 1H), 7.11 (dd, J=11.4, 8.2 Hz, 1H), 6.77-6.84 (m, 1H), 6.53 (s, 2H), 2.28 (s, 3H), 1.28 (s, 12H)

Example 27

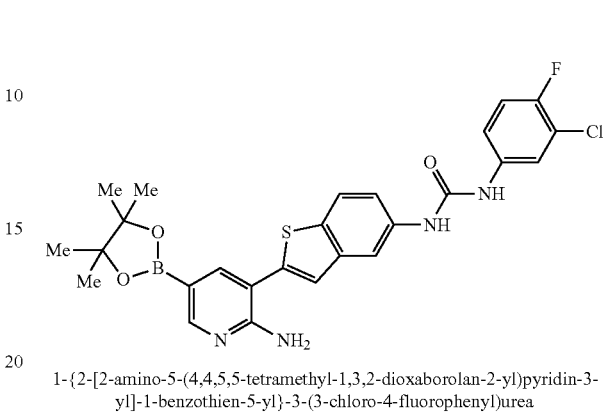

1-{2-[2-amino-5-(4,4,5,5-tetramethyl-1,3,2-dioxaborolan-2-yl)pyridin-3-yl]-1-benzothien-5-yl}-3-(3-chloro-4-fluorophenyl)urea In a manner similar to that described in Example 29, 3-(5-amino-1-benzothien-2-yl)-5-(4,4,5,5-tetramethyl-1,3,2-dioxaborolan-2-yl)pyridin-2-amine and 2-chloro-1-fluoro-4-isocyanatobenzene are converted to the title compound.

¹H NMR (DMSO-d₆) δ: 8.89 (s, 1H), 8.88 (s, 1H), 8.24 (d, J=1.8 Hz, 1H), 8.06 (d, J=2.1 Hz, 1H), 7.81-7.89 (m, 2H), 7.69 (d, J=1.8 Hz, 1H), 7.58 (s, 1H), 7.31-7.41 (m, 3H), 6.52 (s, 2H), 1.28 (s, 12H)

Example 28

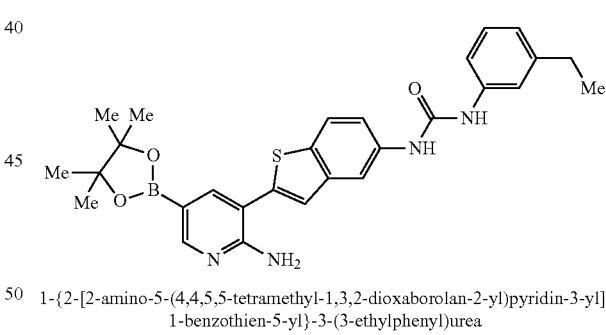

1-{2-[2-amino-5-(4,4,5,5-tetramethyl-1,3,2-dioxaborolan-2-yl)pyridin-3-yl]-1-benzothien-5-yl}-3-(3-ethylphenyl)urea In a manner similar to that described in Example 29, 3-(5-amino-1-benzothien-2-yl)-5-(4,4,5,5-tetramethyl-1,3,2-dioxaborolan-2-yl)pyridin-2-amine and 1-ethyl-3-isocyanatobenzene are converted to the title compound.

¹H NMR (DMSO-d₆) δ: 8.76 (s, 1H), 8.62 (s, 1H), 8.24 (d, J=1.8 Hz, 1H), 8.08 (d, J=2.1 Hz, 1H), 7.85 (d, J=8.8 Hz, 1H), 7.69 (d, J=1.8 Hz, 1H), 7.58 (s, 1H), 7.34-7.39 (m, 2H), 7.23-7.30 (m, 1H), 7.15-7.23 (m, 1H), 6.83 (d, J=7.3 Hz, 1H), 6.52 (s, 2H), 2.58 (q, J=7.5 Hz, 2H), 1.28 (s, 12H), 1.19 (t, J=7.6 Hz, 3H)

Example 29

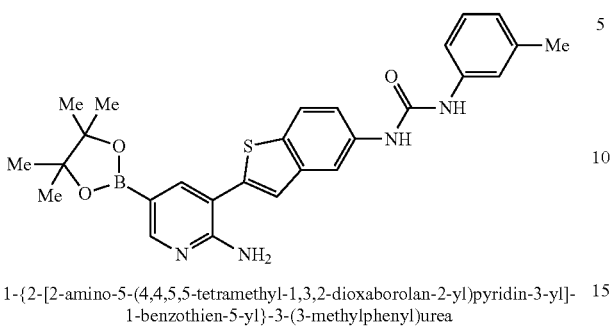

1-{2-[2-amino-5-(4,4,5,5-tetramethyl-1,3,2-dioxaborolan-2-yl)pyridin-3-yl]-1-benzothien-5-yl}-3-(3-methylphenyl)urea To the solution of 3-(5-amino-1-benzothien-2-yl)-5-(4,4,5,5-tetramethyl-1,3,2-dioxaborolan-2-yl)pyridin-2-amine (734.6 mg, 2 mmol. 1 eq) in anhydrous THF (10 mL) at room temperature was added dropwise m-tolylisocyanate (0.251 mL, 1 eq). After the reaction was stirred at room temperature for 4 hours, it was partitioned between ethyl acetate and aqueous ammonium chloride. The organic layer was isolated, washed with saturated aqueous sodium bicarbonate, brine, and dried with anhydrous sodium sulfate. The upper solution layer was decanted, concentrated, and the solid residue was subject to a gradient column chromatography (DCM to MeOH-DCM 1:5). The products' fractions were collected, concentrated, the solid was triturated with EtOAc-Hex (1:7) yielding 1-{2-[2-amino-5-(4,4,5,5-tetramethyl-1,3,2-dioxaborolan-2-yl)pyridin-3-yl]-1-benzothien-5-yl}-3-(3-methylphenyl)urea as a white powder upon filtration in amount of 407 mg.

$^1$H NMR (DMSO-$d_6$) δ: 8.77 (s, 1H), 8.60 (s, 1H), 8.24 (d, J=1.8 Hz, 1H), 8.07 (d, J=1.8 Hz, 1H), 7.85 (d, J=8.5 Hz, 1H), 7.69 (d, J=1.8 Hz, 1H), 7.57 (s, 1H), 7.37 (dd, J=8.6, 2.2 Hz, 1H), 7.32 (s, 1H), 7.22-7.28 (m, 1H), 7.13-7.20 (m, 1H), 6.79 (d, J=7.3 Hz, 1H), 6.52 (s, 2H), 2.29 (s, 3H), 1.28 (s, 12H).

Example 30

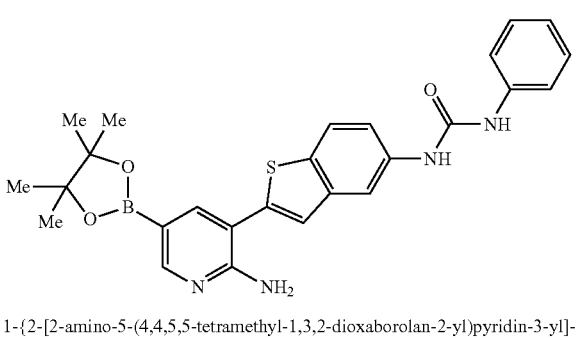

1-{2-[2-amino-5-(4,4,5,5-tetramethyl-1,3,2-dioxaborolan-2-yl)pyridin-3-yl]-1-benzothien-5-yl}-3-phenylurea In a manner similar to that described in Example 29, 3-(5-amino-1-benzothien-2-yl)-5-(4,4,5,5-tetramethyl-1,3,2-dioxaborolan-2-yl)pyridin-2-amine and isocyanatobenzene are converted to the title compound.

$^1$H NMR (DMSO-$d_6$) δ: 8.78 (s, 1H), 8.68 (s, 1H), 8.24 (d, J=1.5 Hz, 1H), 8.07 (d, J=1.5 Hz, 1H), 7.85 (d, J=8.8 Hz, 1H), 7.69 (d, J=1.8 Hz, 1H), 7.58 (s, 1H), 7.48 (d, J=7.6 Hz, 2H), 7.38 (dd, J=8.8, 1.8 Hz, 1H), 7.29 (t, J=7.8 Hz, 2H), 6.94-7.01 (m, 1H), 6.53 (s, 2H), 1.28 (s, 12H).

Example 31

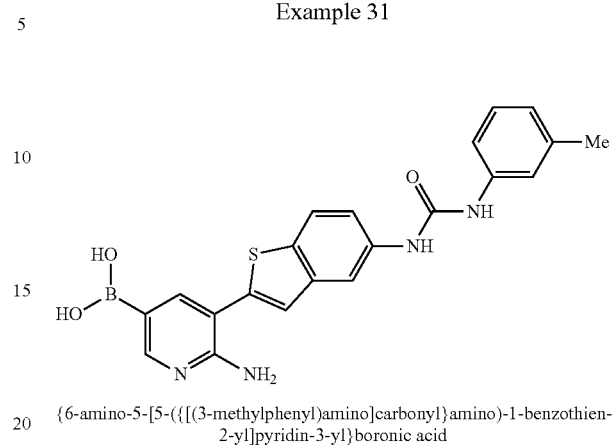

{6-amino-5-[5-({[(3-methylphenyl)amino]carbonyl}amino)-1-benzothien-2-yl]pyridin-3-yl}boronic acid To the solution of 1-{2-[2-amino-5-(4,4,5,5-tetramethyl-1,3,2-dioxaborolan-2-yl)pyridin-3-yl]-1-benzothien-5-yl}-3-(3-methylphenyl)urea (500 mg, 1 mmol, 1 eq) in tetrahydrofuran (6 mL) at room temperature was added dropwise aqueous HCl (3N, 6 mL) and the reaction was stirred at room temperature for 4 hours. The reaction mixture was filtered directly through a Buchner funnel, rinsed with isopropanol, followed by i-PrOH—H$_2$O (1:1) to give {6-amino-5-[5-({[(3-methylphenyl)amino]carbonyl}amino)-1-benzothien-2-yl]pyridin-3-yl}boronic acid as a white solid in amount of 384 mg.

$^1$H NMR (DMSO-$d_6$) δ: 9.26 (s, 1H), 9.02 (s, 1H), 8.54 (br. s., 2H), 8.27 (dd, J=12.0, 1.5 Hz, 2H), 8.20 (d, J=2.1 Hz, 1H), 8.16 (br. s., 2H), 7.94 (d, J=8.8 Hz, 1H), 7.65 (s, 1H), 7.42 (dd, J=8.8, 2.1 Hz, 1H), 7.32 (s, 1H), 7.27 (d, J=8.5 Hz, 1H), 7.12-7.19 (m, 1H), 6.79 (d, J=7.3 Hz, 1H), 2.28 (s, 3H).

Example 32

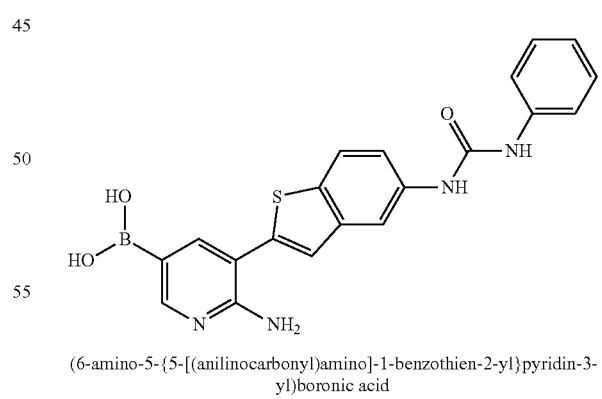

(6-amino-5-{5-[(anilinocarbonyl)amino]-1-benzothien-2-yl}pyridin-3-yl)boronic acid In a manner similar to that described in Example 31, 1-{2-[2-amino-5-(4,4,5,5-tetramethyl-1,3,2-dioxaborolan-2-yl)pyridin-3-yl]-1-benzothien-5-yl}-3-phenylurea was converted to the title compound.

$^1$H NMR (DMSO-$d_6$) δ: 9.13 (s, 1H), 8.97 (s, 1H), 8.52 (br. s., 2H), 8.26 (dd, J=6.4, 1.5 Hz, 2H), 8.19 (d, J=1.8 Hz, 1H), 8.04 (br. s., 2H), 7.94 (d, J=8.8 Hz, 1H), 7.65 (s, 1H), 7.48 (d, J=7.3 Hz, 2H), 7.41 (dd, J=8.8, 2.1 Hz, 1H), 7.29 (t, J=8.1 Hz, 2H), 6.94-7.01 (m, 1H)

Example 33

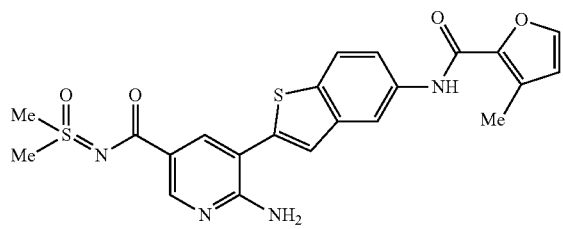

6-amino-N-[dimethyl(oxido)-λ⁴-sulfanylidene]-5-{5-[(3-methyl-2-furoyl)amino]-1-benzothien-2-yl}nicotinamide To the mixture of 6-amino-5-(5-amino-1-benzothien-2-yl)-N-[dimethyl(oxido)-λ⁴-sulfanylidene]nicotinamide (72 mg, 0.2 mmol, 1 eq) and 3-methylfuranylcarboxylic acid (25.2 mg, 1 eq) in dichloroethane (2 mL) at 50° C. was added catalytic amount of DMAP and EDCI (46.1 mg, 1.2 eq). The reaction was stirred at that temperature for 1 h and then at room temperature for 20 h. It was then partitioned between EtOAc and saturated aq NaHCO₃. The organic layer was further washed with brine and then dried with anhydrous sodium sulfate. The organic layer was decanted, concentrated, and the residue was subject to a gradient column chromatography (EtOAc-Hex 2:1 to neat EtOAc) rendering 6-amino-N-[dimethyl(oxido)-λ⁴-sulfanylidene]-5-{5-[(3-methyl-2-furoyl)amino]-1-benzothien-2-yl}nicotinamide as white solid in amount of 90 mg (96%).

$^1$H NMR (DMSO-$d_6$) δ: 10.17 (s, 1H), 8.61 (d, J=2.1 Hz, 1H), 8.41 (d, J=1.8 Hz, 1H), 8.03 (d, J=2.1 Hz, 1H), 7.92 (d, J=8.8 Hz, 1H), 7.81 (d, J=1.5 Hz, 1H), 7.71 (dd, J=8.8, 2.1 Hz, 1H), 7.62 (s, 1H), 6.76 (s, 2H), 6.61 (d, J=1.5 Hz, 1H), 3.44 (s, 6H), 2.37 (s, 3H)

Example 34

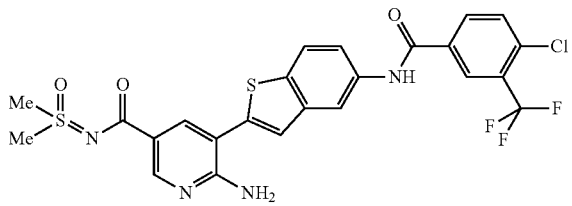

6-amino-5-(5-{[4-chloro-3-(trifluoromethyl)benzoyl]amino}-1-benzothien-2-yl)-N-[dimethyl(oxido)-λ⁴-sulfanylidene]nicotinamide In a manner similar to that described in Example 33, 6-amino-5-(5-amino-1-benzothien-2-yl)-N-[dimethyl(oxido)-λ⁴-sulfanylidene]nicotinamide and 4-chloro-3-(trifluoromethyl)benzoic acid were converted to the title compound.

$^1$H NMR (DMSO-$d_6$) δ: 10.66 (s, 1H), 8.62 (d, J=2.1 Hz, 1H), 8.43 (d, J=1.8 Hz, 1H), 8.38 (d, J=1.8 Hz, 1H), 8.31 (dd, J=8.2, 1.8 Hz, 1H), 8.04 (d, J=2.1 Hz, 1H), 7.99 (d, J=8.8 Hz, 1H), 7.95 (d, J=8.2 Hz, 1H), 7.70 (dd, J=8.5, 2.1 Hz, 1H), 7.68 (s, 1H), 6.79 (s, 2H), 3.44 (s, 6H)

Example 35

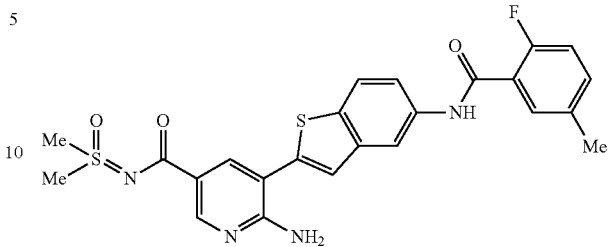

6-amino-N-[dimethyl(oxido)-λ⁴-sulfanylidene]-5-{5-[(2-fluoro-5-methylbenzoyl)amino]-1-benzothien-2-yl}nicotinamide In a manner similar to that described in Example 33, 6-amino-5-(5-amino-1-benzothien-2-yl)-N-[dimethyl(oxido)-λ⁴-sulfanylidene]nicotinamide and 2-fluoro-5-methylbenzoic acid were converted to the title compound.

$^1$H NMR (DMSO-$d_6$) δ: 10.50 (s, 1H), 8.61 (d, J=2.3 Hz, 1H), 8.39 (d, J=1.8 Hz, 1H), 8.04 (d, J=2.3 Hz, 1H), 7.95 (d, J=8.8 Hz, 1H), 7.66 (s, 1H), 7.62 (dd, J=8.7, 1.9 Hz, 1H), 7.50 (dd, J=6.5, 1.8 Hz, 1H), 7.36-7.40 (m, 1H), 7.22-7.26 (m, 1H), 6.78 (s, 2H), 3.44 (s, 6H), 2.36 (s, 3H)

Example 36

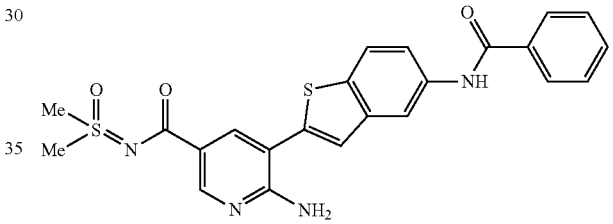

6-amino-5-[5-(benzoylamino)-1-benzothien-2-yl]-N-[dimethyl(oxido)-λ⁴-sulfanylidene]nicotinamide In a manner similar to that described in Example 33, 6-amino-5-(5-amino-1-benzothien-2-yl)-N-[dimethyl(oxido)-λ⁴-sulfanylidene]nicotinamide and benzoic acid were converted to the title compound.

$^1$H NMR (DMSO-$d_6$) δ: 10.39 (s, 1H), 8.61 (d, J=2.1 Hz, 1H), 8.42 (d, J=1.8 Hz, 1H), 8.04 (d, J=2.1 Hz, 1H), 8.00 (d, J=7.0 Hz, 2H), 7.95 (d, J=8.8 Hz, 1H), 7.72 (dd, J=8.7, 1.9 Hz, 1H), 7.66 (s, 1H), 7.59-7.63 (m, 1H), 7.53-7.57 (m, 2H), 6.78 (s, 2H), 3.44 (s, 6H)

Example 37

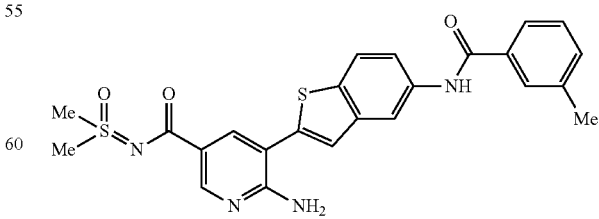

6-amino-N-[dimethyl(oxido)-λ⁴-sulfanylidene]-5-{5-[(3-methylbenzoyl)amino]-1-benzothien-2-yl}nicotinamide In a manner similar to that described in Example 33, 6-amino-5-(5-amino-1-benzothien-2-yl)-N-[dimethyl (oxido)-λ⁴-sulfanylidene]nicotinamide and 3-methylbenzoic acid were converted to the title compound.

¹H NMR (DMSO-d₆) δ: 10.34 (s, 1H), 8.61 (d, J=2.1 Hz, 1H), 8.41 (d, J=1.5 Hz, 1H), 8.04 (d, J=2.1 Hz, 1H), 7.95 (d, J=8.5 Hz, 1H), 7.81 (s, 1H), 7.78 (d, J=6.7 Hz, 1H), 7.71 (dd, J=8.5, 1.8 Hz, 1H), 7.65 (s, 1H), 7.40-7.44 (m, 2H), 6.78 (s, 2H), 3.44 (s, 6H), 2.42 (s, 3H)

Example 38

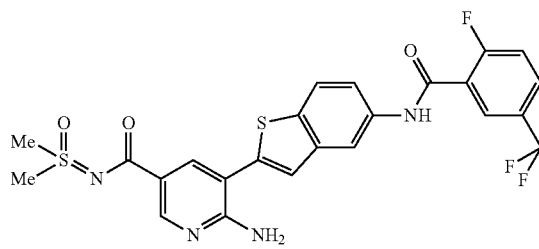

6-amino-N-[dimethyl(oxido)-λ⁴-sulfanylidene]-5-(5-{[2-fluoro-5-(trifluoromethyl)benzoyl]amino}-1-benzothien-2-yl)nicotinamide In a manner similar to that described in Example 33, 6-amino-5-(5-amino-1-benzothien-2-yl)-N-[dimethyl (oxido)-λ⁴-sulfanylidene]nicotinamide and 2-fluoro-5-(trifluoromethyl)benzoic acid were converted to the title compound.

¹H NMR (DMSO-d₆) δ: 10.73 (s, 1H), 8.61 (d, J=2.3 Hz, 1H), 8.37 (d, J=2.1 Hz, 1H), 8.10 (dd, J=6.2, 2.1 Hz, 1H), 8.04 (d, J=2.1 Hz, 1H), 7.99-8.02 (m, 1H), 7.98 (d, J=8.8 Hz, 1H), 7.68 (s, 1H), 7.64 (t, J=9.1 Hz, 1H), 7.61 (dd, J=8.8, 2.1 Hz, 1H), 6.79 (s, 2H), 3.44 (s, 6H)

Example 39

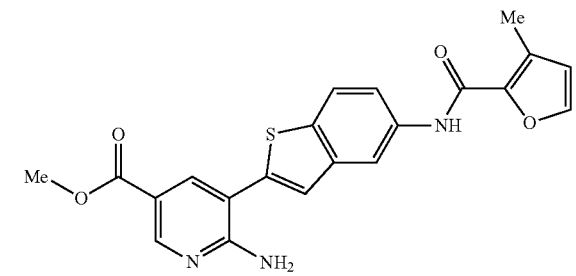

methyl 6-amino-5-{5-[(3-methyl-2-furoyl)amino]-1-benzothien-2-yl}nicotinate

To the mixture of methyl 6-amino-5-(5-amino-1-benzothien-2-yl)nicotinate (120 mg, 0.4 mmol, 1 eq) and 3-methylfuranylcarboxylic acid (50.4 mg, 1 eq) in 1,2-dichloroethane (3 mL) at 60° C. was added catalytic amount of DMAP (10 mg, 0.2 eq) and EDCI (92.2 mg, 1.2 eq). The reaction was stirred at that temperature for 2 h and then partitioned between EtOAc and saturated aq NaHCO₃. The organic layer was further washed with brine and then dried with anhydrous sodium sulfate. The organic layer was decanted, concentrated, and the solid residue which was treated with ethyl acetate with stirring at room temperature for an hour. Methyl 6-amino-5-{5-[(3-methyl-2-furoyl)amino]-1-benzothien-2-yl}nicotinate was obtained upon filtration as a white solid in amount of 128 mg.

¹H NMR (DMSO-d₆) δ: 10.18 (s, 1H), 8.58 (d, J=2.3 Hz, 1H), 8.42 (d, J=2.1 Hz, 1H), 7.95 (d, J=2.1 Hz, 1H), 7.92 (d, J=8.8 Hz, 1H), 7.81 (d, J=1.8 Hz, 1H), 7.72 (dd, J=8.8, 2.1 Hz, 1H), 7.64 (s, 1H), 7.02 (br. s., 2H), 6.61 (d, J=1.5 Hz, 1H), 3.81 (s, 3H), 2.37 (s, 3H)

Example 40

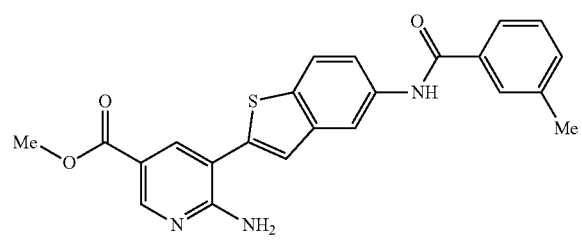

methyl 6-amino-5-{5-[(3-methylbenzoyl)amino]-1-benzothien-2-yl}nicotinate

In a manner similar to that described in Example 39, methyl 6-amino-5-(5-amino-1-benzothien-2-yl)nicotinate and 3-methylbenzoic acid were converted to the title compound.

¹H NMR (DMSO-d₆) δ: 10.34 (s, 1H), 8.58 (d, J=2.1 Hz, 1H), 8.42 (d, J=1.8 Hz, 1H), 7.94-7.97 (m, 2H), 7.81 (s, 1H), 7.78 (d, J=6.7 Hz, 1H), 7.72 (dd, J=8.7, 1.9 Hz, 1H), 7.68 (s, 1H), 7.40-7.45 (m, 2H), 7.03 (br. s., 2H), 3.81 (s, 3H), 2.42 (s, 3H)

Example 41

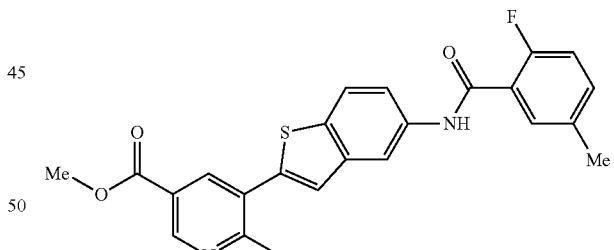

methyl 6-amino-5-{5-[(2-fluoro-5-methylbenzoyl)amino]-1-benzothien-2-yl}nicotinate In a manner similar to that described in Example 39, methyl 6-amino-5-(5-amino-1-benzothien-2-yl)nicotinate and 2-fluoro-5-methylbenzoic acid were converted to the title compound.

¹H NMR (DMSO-d₆) δ: 10.51 (s, 1H), 8.58 (d, J=2.1 Hz, 1H), 8.39 (d, J=1.2 Hz, 1H), 7.94-7.97 (m, 2H), 7.68 (s, 1H), 7.63 (dd, J=8.7, 1.9 Hz, 1H), 7.50 (dd, J=6.5, 1.5 Hz, 1H), 7.36-7.40 (m, 1H), 7.24 (t, J=9.2 Hz, 1H), 7.03 (br. s., 2H), 3.81 (s, 3H), 2.36 (s, 3H)

Example 42

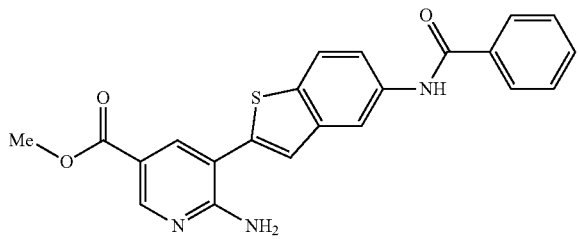

methyl 6-amino-5-[5-(benzoylamino)-1-benzothien-2-yl]nicotinate

In a manner similar to that described in Example 39, methyl 6-amino-5-(5-amino-1-benzothien-2-yl)nicotinate and benzoic acid were converted to the title compound.

$^1$H NMR (DMSO-$d_6$) δ: 10.39 (s, 1H), 8.58 (d, J=2.3 Hz, 1H), 8.43 (d, J=1.8 Hz, 1H), 8.00 (d, J=7.0 Hz, 2H), 7.96 (dd, J=5.6, 3.2 Hz, 2H), 7.73 (dd, J=8.8, 2.1 Hz, 1H), 7.68 (s, 1H), 7.59-7.63 (m, 1H), 7.53-7.58 (m, 2H), 7.04 (br. s., 2H), 3.81 (s, 3H)

Example 43

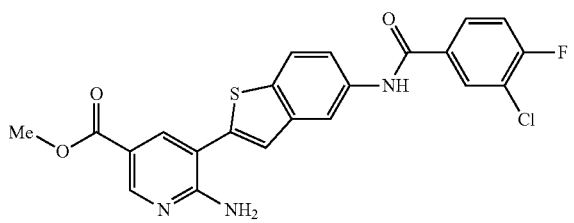

methyl 6-amino-5-{5-[(3-chloro-4-fluorobenzoyl)amino]-1-benzothien-2-yl}nicotinate In a manner similar to that described in Example 39, methyl 6-amino-5-(5-amino-1-benzothien-2-yl)nicotinate and 3-chloro-4-fluorobenzoic acid were converted to the title compound.

$^1$H NMR (DMSO-$d_6$) δ: 10.49 (s, 1H), 8.58 (d, J=2.1 Hz, 1H), 8.39 (d, J=1.8 Hz, 1H), 8.25 (dd, J=7.2, 2.2 Hz, 1H), 8.04 (ddd, J=8.7, 4.7, 2.2 Hz, 1H), 7.95-7.99 (m, 2H), 7.68-7.72 (m, 2H), 7.62 (t, J=9.0 Hz, 1H), 7.04 (br. s., 2H), 3.81 (s, 3H)

Example 44

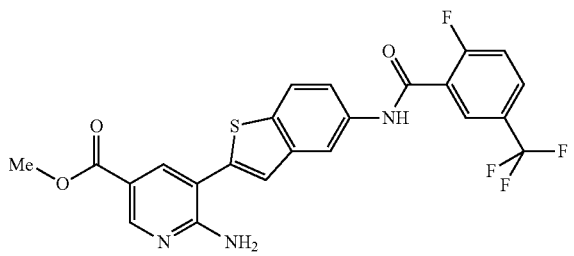

methyl 6-amino-5-(5-{[2-fluoro-5-(trifluoromethyl)benzoyl]amino}-1-benzothien-2-yl)nicotinate In a manner similar to that described in Example 39, methyl 6-amino-5-(5-amino-1-benzothien-2-yl)nicotinate and 2-fluoro-5-(trifluoromethyl)benzoic acid were converted to the title compound.

$^1$H NMR (DMSO-$d_6$) δ: 10.74 (s, 1H), 8.58 (d, J=2.1 Hz, 1H), 8.38 (d, J=2.1 Hz, 1H), 8.10 (dd, J=6.2, 2.1 Hz, 1H), 7.99-8.02 (m, 1H), 7.98 (d, J=8.5 Hz, 1H), 7.96 (d, J=2.1 Hz, 1H), 7.70 (s, 1H), 7.64-7.67 (m, 1H), 7.62 (dd, J=8.7, 1.9 Hz, 1H), 7.04 (br. s., 2H), 3.81 (s, 3H)

Example 45

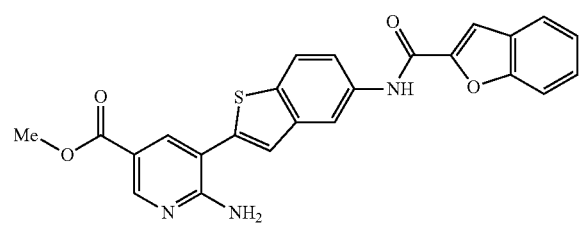

methyl 6-amino-5-{5-[(1-benzofuran-2-ylcarbonyl)amino]-1-benzothien-2-yl}nicotinate In a manner similar to that described in Example 39, methyl 6-amino-5-(5-amino-1-benzothien-2-yl)nicotinate and benzofuran-2-carboxylic acid were converted to the title compound.

$^1$H NMR (DMSO-$d_6$) δ: 10.68 (s, 1H), 8.58 (d, J=2.3 Hz, 1H), 8.45 (d, J=1.8 Hz, 1H), 7.99 (d, J=8.8 Hz, 1H), 7.96 (d, J=2.3 Hz, 1H), 7.85 (d, J=7.6 Hz, 1H), 7.81 (d, J=0.6 Hz, 1H), 7.78 (dd, J=8.7, 1.9 Hz, 1H), 7.75 (d, J=8.2 Hz, 1H), 7.70 (s, 1H), 7.50-7.54 (m, 1H), 7.37-7.40 (m, 1H), 7.05 (br. s., 2H), 3.81 (s, 3H)

Example 46

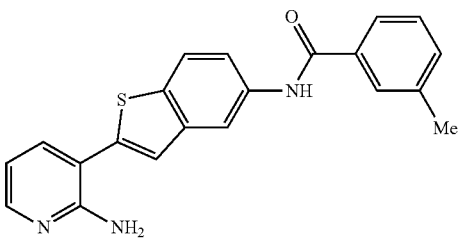

N-[2-(2-aminopyridin-3-yl)-1-benzothien-5-yl]-3-methylbenzamide

In a manner similar to that described in Example 39, 3-(5-aminobenzo[b]thiophen-2-yl)pyridin-2-amine and 3-methylbenzoic acid were converted to the title compound.

$^1$H NMR (DMSO-$d_6$) δ: 10.33 (s, 1H), 8.40 (d, J=1.8 Hz, 1H), 8.02 (dd, J=4.7, 1.8 Hz, 1H), 7.93 (d, J=8.8 Hz, 1H), 7.81 (s, 1H), 7.78 (d, J=6.7 Hz, 1H), 7.69 (dd, J=8.7, 1.9 Hz, 1H), 7.64 (s, 1H), 7.60 (dd, J=7.3, 1.8 Hz, 1H), 7.40-7.45 (m, 2H), 6.70 (dd, J=7.3, 5.0 Hz, 1H), 6.06 (s, 2H), 2.42 (s, 3H)

Example 47

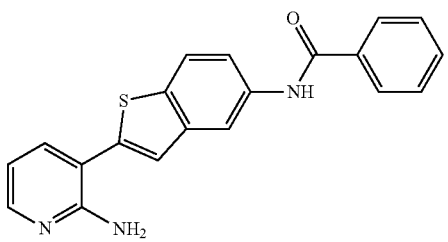

N-[2-(2-aminopyridin-3-yl)-1-benzothien-5-yl]benzamide

In a manner similar to that described in Example 39, 3-(5-aminobenzo[b]thiophen-2-yl)pyridin-2-amine and benzoic acid were converted to the title compound.

$^1$H NMR (DMSO-$d_6$) δ: 10.38 (s, 1H), 8.40 (d, J=1.8 Hz, 1H), 7.90-8.04 (m, 4H), 7.70 (dd, J=8.8, 1.8 Hz, 1H), 7.52-7.66 (m, 5H), 6.70 (dd, J=7.5, 4.8 Hz, 1H), 6.07 (s, 2H)

Example 48

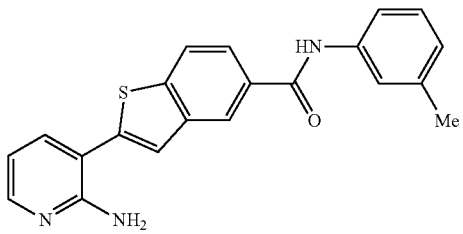

2-(2-aminopyridin-3-yl)-N-(3-methylphenyl)-1-benzothiophene-5-carboxamide

In a manner similar to that described in Example 51, 2-(2-aminopyridin-3-yl)-1-benzothiophene-5-carboxylic acid and m-toluidine were converted to the title compound.

$^1$H NMR (DMSO-$d_6$) δ: 10.27 (s, 1H), 8.48 (s, 1H), 8.13 (d, J=8.2 Hz, 1H), 8.04 (d, J=4.7 Hz, 1H), 7.95 (d, J=8.5 Hz, 1H), 7.77 (s, 1H), 7.67 (s, 1H), 7.62 (t, J=8.2 Hz, 2H), 7.25 (t, J=7.8 Hz, 1H), 6.94 (d, J=7.6 Hz, 1H), 6.72 (dd, J=7.2, 5.1 Hz, 1H), 6.10 (s, 2H), 2.33 (s, 3H)

Example 49

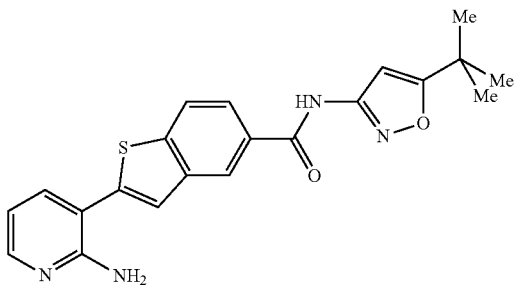

2-(2-aminopyridin-3-yl)-N-(5-tert-butylisoxazol-3-yl)-1-benzothiophene-5-carboxamide In a manner similar to that described in Example 51, 2-(2-aminopyridin-3-yl)-1-benzothiophene-5-carboxylic acid and 5-(tert-butyl)isoxazol-3-amine were converted to the title compound.

$^1$H NMR (DMSO-$d_6$) δ: 11.43 (s, 1H), 8.54 (s, 1H), 8.13 (d, J=8.5 Hz, 1H), 8.04 (dd, J=4.7, 1.5 Hz, 1H), 7.98 (dd, J=8.5, 1.5 Hz, 1H), 7.75 (s, 1H), 7.62 (dd, J=7.3, 1.5 Hz, 1H), 6.77 (s, 1H), 6.71 (dd, J=7.3, 4.7 Hz, 1H), 6.10 (s, 2H), 1.34 (s, 9H).

Example 50

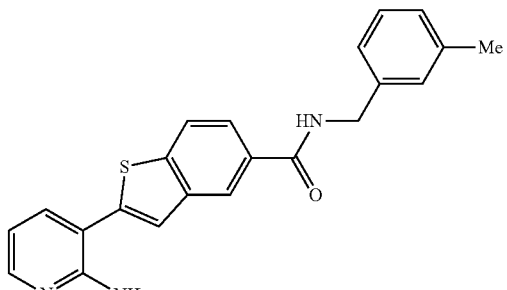

2-(2-aminopyridin-3-yl)-N-(3-methylbenzyl)-1-benzothiophene-5-carboxamide

In a manner similar to that described in Example 51, 2-(2-aminopyridin-3-yl)-1-benzothiophene-5-carboxylic acid and m-tolylmethanamine were converted to the title compound.

$^1$H NMR (DMSO-$d_6$) δ: 9.11 (t, J=5.9 Hz, 1H), 8.41 (s, 1H), 8.07 (d, J=8.2 Hz, 1H), 8.03 (dd, J=4.7, 1.5 Hz, 1H), 7.88 (dd, J=8.5, 1.2 Hz, 1H), 7.72 (s, 1H), 7.60 (dd, J=7.6, 1.5 Hz, 1H), 7.20-7.24 (m, 1H), 7.12-7.17 (m, 2H), 7.06 (d, J=7.6 Hz, 1H), 6.70 (dd, J=7.3, 5.0 Hz, 1H), 6.08 (s, 2H), 4.49 (d, J=5.9 Hz, 2H), 2.29 (s, 3H)

Preparation 5

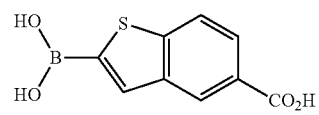

2-(dihydroxyboryl)-1-benzothiophene-5-carboxylic acid

Benzothiophene-5-carboxylic acid (2 g, 11.2 mmol, 1 eq) was dissolved in anhydrous THF (50 mL). To the solution was added dropwise tert-BuLi petane solution (1.7M, 20 mL, 3 eq) at −78° C. for 5 minutes under nitrogen atmosphere. The reaction mixture was allowed to warm to room temperature, stirred for 30 minutes, and cooled to −78° C. again, followed by an addition of triisopropyl borate (3.97 mL, 1.5 eq). The reaction was then allowed to warm to room temperature and stirred at that temperature for one hour. To the reaction mixture was added saturated aqueous ammonium chloride (50 mL) and 10% aqueous potassium hydrogensulfate solution (50 mL) to adjust pH to 2. After the mixture was stirred at room temperature for 30 minutes, it was extracted with ethyl acetate. The organic layer was washed with saturated brine and dried over anhydrous sodium sulfate. The upper solution was decanted, concentrated, and the residue was suspended in Hexane/CHCl$_3$/MeOH (40:4:1). The solid was filtered, rinsed with hexane. 2-(dihydroxyboryl)-1-benzothiophene-5-carboxylic acid was obtained as a grayish solid in amount of 1.325 g (53%).

$^1$H NMR (DMSO-$d_6$) δ: 12.94 (br. s., 1H), 8.57 (br. s., 2H), 8.49 (s, 1H), 8.05-8.09 (m, 2H), 7.90 (d, J=8.5 Hz, 1H).

Preparation 6

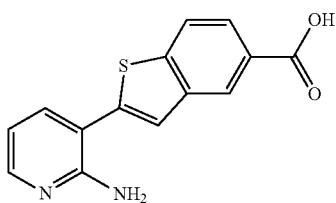

2-(2-aminopyridin-3-yl)-1-benzothiophene-5-carboxylic acid

To the degassed mixture of 2-amino-3-iodpyridine (1.12 g, 5.09 mmol, 1 eq), 2-(dihydroxyboryl)-1-benzothiophene-5-carboxylic acid, [2-(dihydroxyboryl)-1-benzothiophene-5-carboxylic acid (1.3 g, 1.15 eq)], and aqueous sodium carbonate (2M, 7.6 mL, 3 eq) in dioxane (10 mL) was added Ph$_3$P (267 mg, 0.2 eq) and Pd(OAc)$_2$ (114.3 mg, 0.1 eq). The mixture was heated to 50° C. with vigorous stirring for 30 minutes. The yellow mixture was then partitioned between aq NH$_4$Cl and MeOH—CHCl$_3$ (1:5). Some solids precipitation was observed. After the pH was carefully adjusted to around 6, the whole mixture was filtered through a Buchner funnel to obtain a yellow solid. The solid was further triturated with MeOH/H$_2$O to give 2-(2-aminopyridin-3-yl)-1-benzothiophene-5-carboxylic acid as a white-off solid in amount of 1.18 g after dried in vacuo (86%).

$^1$H NMR (DMSO-d$_6$) δ: 12.97 (br. s., 1H), 8.46 (s, 1H), 8.09 (d, J=8.5 Hz, 1H), 8.03 (d, J=3.5 Hz, 1H), 7.90 (dd, J=8.4, 1.3 Hz, 1H), 7.77 (s, 1H), 7.60 (dd, J=7.3, 1.2 Hz, 1H), 6.70 (dd, J=7.3, 5.0 Hz, 1H), 6.09 (br. s., 2H)

Example 51

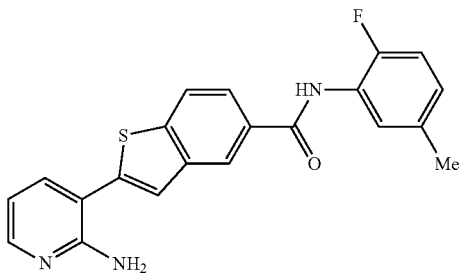

2-(2-aminopyridin-3-yl)-N-(2-fluoro-5-methylphenyl)-1-benzothiophene-5-carboxamide The reaction mixture of 2-(2-aminopyridin-3-yl)-1-benzothiophene-5-carboxylic acid (54 mg, 0.2 mmol, 1 eq), 2-fluoro-5-methylaniline (0.048 mL, 2.1 eq), DMAP (5 mg, 0.2 eq), and EDCI (46.1 mg, 1.2 eq) in anhydrous 1,2-dichloroethane (2 mL) and anhydrous DMF (0.5 mL) was stirred and heated at 60° C. for 1 hour. It was then diluted with ethyl acetate, washed sequentially with aqueous NH$_4$Cl, saturated aqueous NaHCO$_3$, and brine, and finally dried with anhydrous sodium sulfate. The upper, clear solution-layer was decanted, concentrated, and the solid residue was subject to a gradient column chromatography (EtOAc-Hex 1:4 to 1:1) to yield 2-(2-aminopyridin-3-yl)-N-(2-fluoro-5-methylphenyl)-1-benzothiophene-5-carboxamide as a white solid in amount of 39.8 mg.

$^1$H NMR (DMSO-d$_6$) δ: 10.14 (s, 1H), 8.49 (s, 1H), 8.13 (d, J=8.5 Hz, 1H), 8.04 (dd, J=4.7, 1.2 Hz, 1H), 7.95 (dd, J=8.5, 0.9 Hz, 1H), 7.77 (s, 1H), 7.62 (dd, J=7.3, 1.2 Hz, 1H), 7.45 (d, J=6.2 Hz, 1H), 7.18 (dd, J=10.0, 8.8 Hz, 1H), 7.06-7.09 (m, 1H), 6.71 (dd, J=7.3, 5.0 Hz, 1H), 6.10 (s, 2H), 2.32 (s, 3H).

Example 52

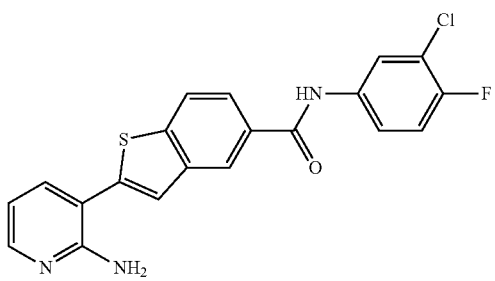

2-(2-aminopyridin-3-yl)-N-(3-chloro-4-fluorophenyl)-1-benzothiophene-5-carboxamide In a manner similar to that described in Example 51, 2-(2-aminopyridin-3-yl)-1-benzothiophene-5-carboxylic acid and 3-chloro-4-fluoroaniline were converted to the title compound.

$^1$H NMR (DMSO-d$_6$) δ: 10.54 (s, 1H), 8.47 (s, 1H), 8.16 (d, J=8.5 Hz, 1H), 8.13 (dd, J=6.7, 2.6 Hz, 1H), 8.04 (dd, J=4.7, 1.5 Hz, 1H), 7.94 (dd, J=8.5, 1.2 Hz, 1H), 7.76-7.79 (m, 2H), 7.62 (dd, J=7.3, 1.5 Hz, 1H), 7.44 (t, J=9.1 Hz, 1H), 6.71 (dd, J=7.3, 5.0 Hz, 1H), 6.10 (s, 2H)

Example 53

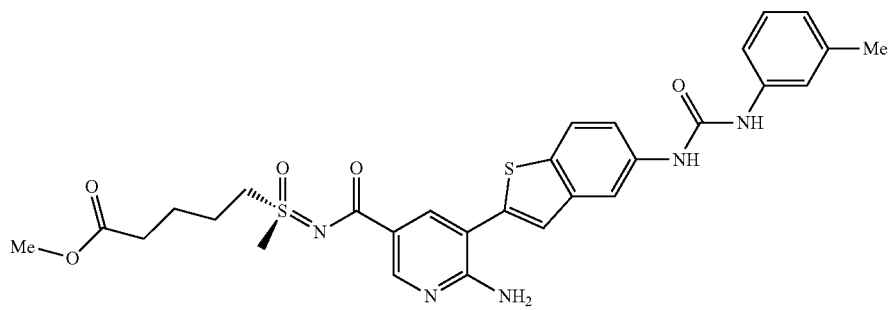

methyl 5-[N-({6-amino-5-[5-({[(3-methylphenyl)amino]carbonyl}amino)-1-benzothien-2-yl]pyridin-3-yl}carbonyl)-S-methylsulfonimidoyl]pentanoate To 6-amino-5-[5-({[(3-methylphenyl)amino]carbonyl}amino)-1-benzothien-2-yl]nicotinic acid (418 mg, 1 mmol, 1 equiv.) and (S)-methyl 5-(S-methylsulfonimidoyl)pentanoate (232 mg, 1.2 equiv.) in anhydrous DMF (6 mL) under nitrogen atmosphere was added diisopropylethylamine (0.348 mL, 2.0 equiv.) and (benzotriazol-1-yloxy)tris(dimethylamino)phosphonium hexafluorophosphate (486.5 mg, 1.1 equiv.). The reaction mixture was heated to 60° C. and stirred for 2 hours. After the reaction was cooled to room temperature, it was diluted with EtOAc and washed sequentially with saturated aqueous NaHCO₃, brine, aqueous NH₄Cl, and brine. After the organic layer was dried (anhydrous Na₂SO₄), it was decanted, concentrated, and the brown oily residue was subject to a column chromatography (EtOAc-Hex 1:4 to 6:1). methyl 5-[N-({6-amino-5-[5-({[(3-methylphenyl)amino]carbonyl}amino)-1-benzothien-2-yl]pyridin-3-yl}carbonyl)-S-methylsulfonimidoyl]pentanoate was obtained as a yellow foam in amount of 394 mg (66%).

$^1$H NMR (DMSO-d$_6$) δ: 8.78 (s, 1H), 8.61 (s, 1H), 8.60 (s, 1H), 8.10 (d, J=2.1 Hz, 1H), 8.02 (d, J=2.3 Hz, 1H), 7.87 (d, J=8.5 Hz, 1H), 7.59 (s, 1H), 7.37 (dd, J=8.8, 2.1 Hz, 1H), 7.33 (s, 1H), 7.22-7.28 (m, 1H), 7.13-7.20 (m, 1H), 6.80 (d, J=7.6 Hz, 1H), 6.75 (s, 2H), 3.55-3.63 (m, 5H), 3.41 (s, 3H), 2.39 (t, J=7.2 Hz, 2H), 2.29 (s, 3H), 1.76-1.87 (m, 2H), 1.63-1.74 (m, 2H)

Example 54

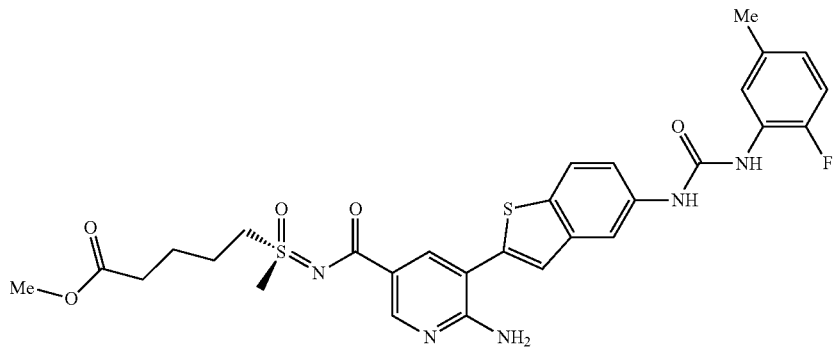

methyl 5-[N-({6-amino-5-[5-({[(2-fluoro-5-methylphenyl)amino]carbonyl}amino)-1-benzothien-2-yl]pyridin-3-yl}carbonyl)-S-methylsulfonimidoyl]pentanoate In a manner similar to that described in Example 53, 6-amino-5-(5-(3-(2-fluoro-5-methylphenyl)ureido)benzo[b]thiophen-2-yl)nicotinic acid and (S)-methyl 5-(S-methylsulfonimidoyl)pentanoate were converted to the title compound.

$^1$H NMR (DMSO-d$_6$) δ: 9.19 (s, 1H), 8.61 (d, J=2.1 Hz, 1H), 8.51 (d, J=2.3 Hz, 1H), 8.12 (d, J=1.8 Hz, 1H), 8.00-8.05 (m, 2H), 7.88 (d, J=8.5 Hz, 1H), 7.60 (s, 1H), 7.36 (dd, J=8.8, 2.1 Hz, 1H), 7.11 (dd, J=11.4, 8.2 Hz, 1H), 6.77-6.84 (m, 1H), 6.76 (s, 2H), 3.53-3.65 (m, 5H), 3.41 (s, 3H), 2.40 (t, J=7.0 Hz, 2H), 2.28 (s, 3H), 1.75-1.88 (m, 2H), 1.64-1.74 (m, 2H)

Example 55

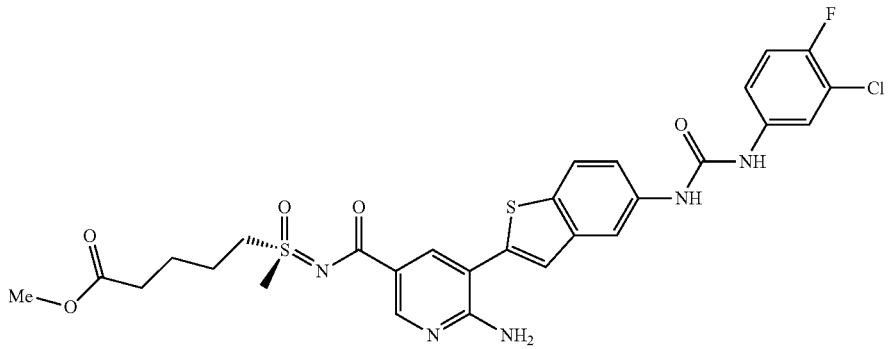

methyl 5-[N-({6-amino-5-[5-({[(3-chloro-4-fluorophenyl)amino]carbonyl}amino)-1-benzothien-2-yl]pyridin-3-yl}carbonyl)-S-methylsulfonimidoyl]pentanoate In a manner similar to that described in Example 53, 6-amino-5-(5-(3-(3-chloro-4-fluorophenyl)ureido)benzo[b]thiophen-2-yl)nicotinic acid and (S)-methyl 5-(S-methylsulfonimidoyl)pentanoate were converted to the title compound.

$^1$H NMR (DMSO-d$_6$) δ: 8.90 (s, 1H), 8.90 (s, 1H), 8.61 (d, J=2.3 Hz, 1H), 8.08 (d, J=2.1 Hz, 1H), 8.01 (d, J=2.3 Hz, 1H), 7.88 (d, J=8.8 Hz, 1H), 7.81-7.86 (m, 1H), 7.60 (s, 1H), 7.31-7.41 (m, 3H), 6.76 (s, 2H), 3.54-3.63 (m, 5H), 3.41 (s, 3H), 2.39 (t, J=7.2 Hz, 2H), 1.75-1.88 (m, 2H), 1.63-1.74 (m, 2H)

Preparation 7

2,2,3,3,13,13,14,14-octamethyl-4,12-dioxa-8-thia-3,13-disilapentadecane

To the solution of 3,3'-thiodipropanol (5 g, 32.6 mmol, 1 eq) and tert-butyldimethylsilyl chloride (13.18 g, 2.6 eq) in anhydrous DMF (25 mL) at 0° C. was added imidazole (11.21 g, 5 eq). After the reaction was stirred at room temperature for one hour, it was partitioned between ethyl acetate and water. The organic layer was isolated, washed once more with water, then brine, and lastly dried with anhydrous sodium sulfate. The upper clear solution was decanted, concentrated, and the oily residue was subject to a column chromatography (EtOC-Hex: from 1:9 to 4:1). 2,2,3,3,13,13,14,14-octamethyl-4,12-dioxa-8-thia-3,13-disilapentadecane, was obtained as clear oil in 12.32 g.

$^1$H NMR (DMSO-d$_6$) δ: 3.64 (t, J=6.2 Hz, 4H), 2.49-2.53 (m, 4H), 1.65-1.71 (m, 4H), 0.86 (s, 18H), 0.03 (s, 12H)

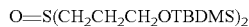

Preparation 8

2,2,3,3,13,13,14,14-octamethyl-4,12-dioxa-8-thia-3,13-disilapentadecane 8-oxide A solution of sodium (meta)periodate (7.751 g, 1.1 eq) in water (40 mL) was slowly poured into a solution of 2,2,3,3,13,13,14,14-octamethyl-4,12-dioxa-8-thia-3,13-disilapentadecane, (12.32 g, 1 eq) in methanol (150 mL) at 0° C. and the reaction mixture was stirred at room temperature for 2 hours. The reaction mixture was then filtered through a pad of celite and silica gel which was washed with methanol. The filtrate was concentrated under reduced pressure at a temperature below 25° C. The residue was diluted with brine and extracted a couple of times with chloroform. All organic solvents were combined, dried with anhydrous sodium sulfate, and concentrated to give a clear oil as crude 2,2,3,3,13,13,14,14-octamethyl-4,12-dioxa-8-thia-3,13-disilapentadecane 8-oxide, in amount of 12.84 g.

$^1$H NMR (DMSO-d$_6$) δ: 3.69 (t, J=6.2 Hz, 4H), 2.59-2.83 (m, 4H), 1.80 (tdd, J=6.8, 6.7, 6.4 Hz, 4H), 0.86 (s, 18H), 0.04 (s, 12H)

Preparation 9

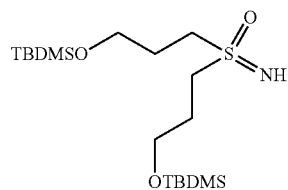

8-imino-2,2,3,3,13,13,14,14-octamethyl-4,12-dioxa-8λ$^4$-thia-3,13-disilapentadecane 8-oxide To the solution of above obtained crude oil 2,2,3,3,13,13,14,14-octamethyl-4,12-dioxa-8-thia-3,13-disilapentadecane 8-oxide, in anhydrous dichloromethane (150 mL) was added trifluoroacetamide (7.60 g, 2 eq), magnesium oxide (5.256 g, 4 eq), rhodium acetate dimer (432 mg, 0.03 eq), and (diacetoxyiodo)benzene (15.75 g, 1.5 eq) under nitrogen atmosphere at room temperature. The greenish reaction mixture was stirred at room temperature for 18 hours. Then additional amount of trifluoroacetamide (3.0 g), rhodium acetate dimer (300 mg), (diacetoxyiodo)benzene (5.0 g), and anhydrous dichloromethane (100 mL) was added. The mixture was continued being stirred at room temperature for another 3 hours and then filtered through a pad of celite and silica gel. The pad was washed first with dichloromethane followed by MeOH-DCM (1:5). The filtrate was concentrated and the brown oil was taken up into methanol (200 mL). Potassium carbonate (22.53 g, 5 eq) was added to the newly formed solution. After the mixture was stirred at room temp for 2 hours, it was filtered through a pad of celite and silica gel. The pad was washed first with DCM-EtOAC (1:1) followed by a later 10% (v/v) addition of MeOH with stirring of the sediment on top of the pad. The filtrate was concentrated and the residue mixture was treated with DCM-EtOAc (2:3) with stirring at room temp for 30 minutes. The mixture was filtered again through a pad of celite and silica gel. This filtration and concentration circle may be repeated a couple of times such that most of the solid by-product was removed and a redish oil was obtained. Upon a gradient column chromatography (EtOAc-HEX 1:20 to 1:1) 8-imino-2,2,3,3,13,13,14,14-octamethyl-4,12-dioxa-8λ$^4$-thia-3,13-disilapentadecane 8-oxide, was obtained as a reddish oil in amount of 9.538 g with a total yield of 72% for 4 steps.

$^1$H NMR (DMSO-d$_6$) δ: 3.67 (t, J=6.3 Hz, 4H), 3.65 (s, 1H), 2.99 (t, J=7.9 Hz, 4H), 1.82-1.88 (m, 4H), 0.86 (s, 18H), 0.04 (s, 12H)

Example 56

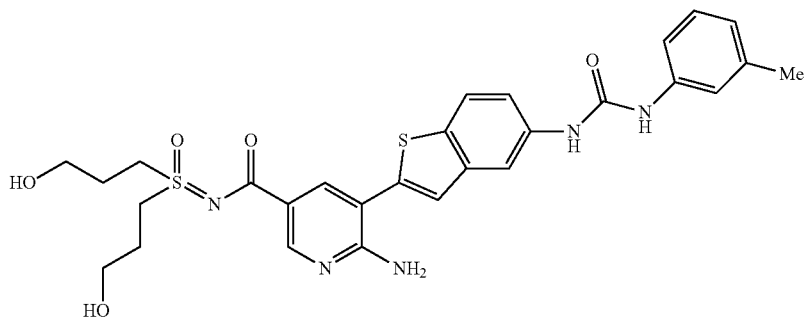

6-amino-N-[bis(3-hydroxypropyl)(oxido)-λ⁴-sulfanylidene]-5-[5-({[(3-methylphenyl)amino]carbonyl}amino)-1-benzothien-2-yl]nicotinamide The reaction mixture of 8-imino-2,2,3,3,13,13,14,14-octamethyl-4,12-dioxa-8λ⁴-thia-3,13-disilapentadecane 8-oxide, (102.25 mg, 0.25 mmol, 1 eq), 6-amino-5-[5-({[(3-methylphenyl)amino]carbonyl}amino)-1-benzothien-2-yl] nicotinic acid (89 mg, 1 eq), DMAP (6.125 mg, 0.2 eq), and EDCI (57.6 mg, 1.2 eq) in anhydrous DCE (2.5 mL) was heated at 70° C. for 2 hours. It was then diluted with DCM, washed sequentially with aqueous NH₄Cl, saturated aqueous NaHCO₃, and brine, and dried with anhydrous sodium sulfate. The upper clear solution was decanted, concentrated, and the oily residue was subject to gradient column chromatography (EtOAc-Hex 1:30 to 2:1) yielding 6-amino-N-[bis(3-{[tert-butyl(dimethyl)silyl]oxy}propyl)(oxido)-λ⁴-sulfanylidene]-5-[5-({[(3-methylphenyl)amino]carbonyl}amino)-1-benzothien-2-yl]nicotinamide as a white foam in amount of 70 mg.

¹H NMR (DMSO-d₆) δ: 8.77 (s, 1H), 8.59-8.61 (m, 2H), 8.10 (d, J=2.1 Hz, 1H), 8.01 (d, J=2.1 Hz, 1H), 7.85 (d, J=8.8 Hz, 1H), 7.57 (s, 1H), 7.37 (dd, J=8.8, 2.1 Hz, 1H), 7.33 (s, 1H), 7.25 (d, J=8.2 Hz, 1H), 7.16 (t, J=7.8 Hz, 1H), 6.80 (d, J=7.6 Hz, 1H), 6.76 (br. s., 2H), 3.71 (t, J=6.2 Hz, 4H), 3.62-3.70 (m, 4H), 2.29 (s, 3H), 1.89-1.98 (m, 4H), 0.85 (s, 18H), 0.03 (s, 12H)

To the solution of 6-amino-N-[bis(3-{[tert-butyl(dimethyl)silyl]oxy}propyl)(oxido)-λ⁴-sulfanylidene]-5-[5-({[(3-methylphenyl)amino]carbonyl}amino)-1-benzothien-2-yl]nicotinamide (70 mg, 0.086 mmol, 1 eq) in anhydrous THF (2 mL) at 0° C. was added dropwise tetrabutylammonium fluoride (0.355 mL, 1.0M in anhyd. THF, 4.1 eq) and the reaction was stirred at that temp for 2 hours. The reaction was then partitioned between saturated aqueous NaHCO₃ and ethyl acetate. The organic layer was further washed with aqueous NH₄Cl, brine, lastly dried with anhydrous Na₂SO₄. The upper solution was decanted, concentrated, and the solid residue was wrapped with silica gel which was subject to a gradient column chromatography (EtOAc-Hex 6:1 to MeOH-EtOAc 1:9) to give 6-amino-N-[bis(3-hydroxypropyl)(oxido)-λ⁴-sulfanylidene]-5-[5-({[(3-methylphenyl)amino]carbonyl}amino)-1-benzothien-2-yl]nicotinamide as a slightly brown solid in amount of 42 mg.

¹H NMR (DMSO-d₆) δ: 8.84 (s, 1H), 8.67 (s, 1H), 8.62 (d, J=2.3 Hz, 1H), 8.10 (d, J=1.8 Hz, 1H), 8.01 (d, J=2.1 Hz, 1H), 7.87 (d, J=8.8 Hz, 1H), 7.59 (s, 1H), 7.37 (dd, J=8.5, 2.1 Hz, 1H), 7.33 (s, 1H), 7.25 (d, J=8.2 Hz, 1H), 7.16 (t, J=7.8 Hz, 1H), 6.79 (d, J=7.3 Hz, 1H), 6.76 (s, 2H), 4.74 (t, J=5.3 Hz, 2H), 3.62-3.68 (m, 2H), 3.55-3.60 (m, 2H), 3.52 (q, J=6.1 Hz, 4H), 2.29 (s, 3H), 1.84-1.96 (m, 4H)

Example 57

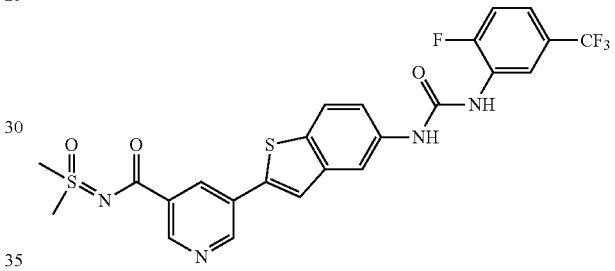

N-[dimethyl(oxido)-λ⁴-sulfanylidene]-5-{5-[({[2-fluoro-5-(trifluoromethyl)phenyl]amino}carbonyl)amino]-1-benzothien-2-yl}nicotinamide Synthesized using a procedure similar to Example 1.

¹H NMR (600 MHz, DMSO-d₆) δ ppm 9.35 (s, 1H) 9.18 (d, J=2.35 Hz, 1H) 9.09 (d, J=2.05 Hz, 1H) 8.94 (d, J=2.93 Hz, 1H) 8.66 (dd, J=7.19, 2.20 Hz, 1H) 8.51 (t, J=2.05 Hz, 1H) 8.19 (d, J=1.76 Hz, 1H) 8.08 (s, 1H) 7.96 (d, J=8.80 Hz, 1H) 7.51 (dd, J=10.56, 8.80 Hz, 1H) 7.38-7.42 (m, 2H) 3.54 (s, 6H)

Example 58

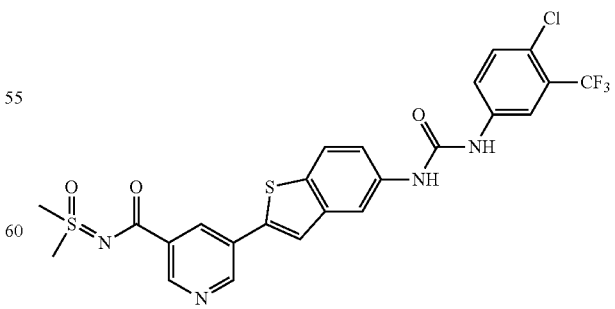

5-{5-[({[4-chloro-3-(trifluoromethyl)phenyl]amino}carbonyl)amino]-1-benzothien-2-yl}-N-[dimethyl(oxido)-λ⁴-sulfanylidene]nicotinamide Synthesized using a procedure similar to Example 1.

$^1$H NMR (600 MHz, DMSO-d$_6$) δ ppm 9.22 (s, 1H) 9.18 (d, J=2.35 Hz, 1H) 9.08 (d, J=1.76 Hz, 1H) 9.03 (s, 1H) 8.51 (t, J=2.20 Hz, 1H) 8.15 (dd, J=4.70, 2.35 Hz, 2H) 8.07 (s, 1H) 7.94 (d, J=8.51 Hz, 1H) 7.65-7.68 (m, 1H) 7.61-7.64 (m, 1H) 7.42 (dd, J=8.51, 2.05 Hz, 1H) 3.54 (s, 6H) The compounds represented by Formula II can be synthesized according to the following example.

Example 60

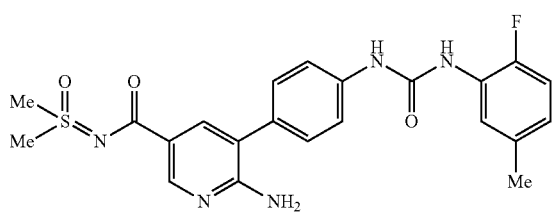

6-amino-N-[dimethyl(oxido)-λ$^4$-sulfanylidene]-5-[4-({[(2-fluoro-5-methylphenyl)amino]carbonyl}amino)phenyl]nicotinamide 1-(2-fluoro-5-methylphenyl)-3-(4-(4,4,5,5-tetramethyl-1,3,2-dioxaborolan-2-yl)phenyl)urea (212 mg, 0.6 mmoles) and 6-amino-N-[dimethyl(oxido)-λ$^4$-sulfanylidene]-5-iodonicotinamide (170 mg, 0.5 mmoles) was added to a mixture of 6 ml of dioxane and 2 ml of 2M aqueous Sodium Carbonate. Next, Palladium(II) Acetate (~5 mol %, 6 mg) and Triphenylphosphene (~20 mol %, 27 mg) was added, followed by 2 ml of dioxane. Dry nitrogen was bubbled through the resulting solution for 15 minutes. Following this, the reaction mixture was set up with a reflux condenser, under nitrogen atmosphere, and heated at 95 C for 2 hours. The reaction was then cooled to room temperature and 40 ml of ethyl acetate was added. The mixture was transferred to a separatory funnel and extracted with saturated Sodium Bicarbonate (3×40 ml) followed by saturated NaCl (3×40 ml). The organic layer was dried with anhydrous Sodium Sulfate, loaded onto silica and columned using ethyl acetate/hexanes, to give 120 mg of the product.

$^1$H NMR (dmso) δ: 9.18 (s, 1H), 8.55 (d, J=2.0 Hz, 1H), 8.50 (d, J=2.6 Hz, 1H), 8.00 (dd, J=7.8, 1.9 Hz, 1H), 7.75 (d, J=2.3 Hz, 1H), 7.52-7.59 (m, 2H), 7.30-7.38 (m, 2H), 7.10 (dd, J=11.4, 8.2 Hz, 1H), 6.79 (s, 1H), 6.24 (s, 2H), 3.41 (s, 6H), 2.27 (s, 3H)

Example 64

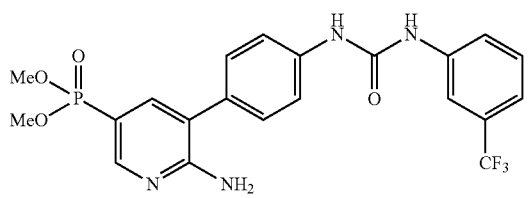

dimethyl (6-amino-5-(4-(3-(3-(trifluoromethyl)phenyl)ureido)phenyl)pyridin-3-yl)phosphonate The reaction mixture of dimethyl (6-amino-5-(4-aminophenyl)pyridin-3-yl)phosphonate (30 mg, 0.10 mmol, 1 eq) and 1-isocyanato-3-(trifluoromethyl)benzene (0.018 mL, 1.2 eq) in anhydrous DMF (0.5 mL) under anhydrous nitrogen atmosphere was stirred at room temperature for an hour. It was then diluted with ethyl acetate, washed sequentially with aqueous ammonium chloride, saturated aqueous sodium bicarbonate, brine, and lastly dried with anhydrous sodium sulfate. The upper clear solution was decanted, concentrated, and the solid residue was subject to a gradient column chromatography (EtOAc-Hex 2:1 to MeOH-EtOAc 1:20) to yield dimethyl (6-amino-5-(4-(3-(3-(trifluoromethyl)phenyl)ureido)phenyl)pyridin-3-yl)phosphonate as a white solid in amount of 41 mg.

$^1$H NMR (300 MHz, DMSO-d$_6$) δ ppm 9.12 (s, 1H) 9.01 (s, 1H) 8.19 (dd, J=6.37, 2.12 Hz, 1H) 8.03 (s, 1H) 7.56-7.64 (m, 3H) 7.49-7.55 (m, 1H) 7.29-7.42 (m, 4H) 6.44 (br. s., 2H) 3.65 (s, 3H) 3.62 (s, 3H).

Example 65

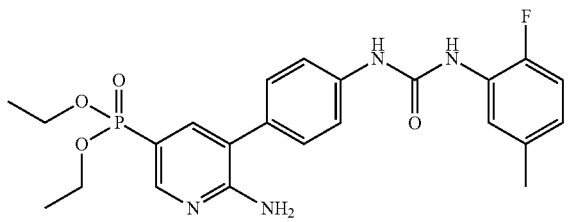

dimethyl [6-amino-5-(4-{[(2-fluoro-5-methylphenyl)carbamoyl]amino}phenyl)pyridin-3-yl]phosphonate Synthesized using a procedure similar to Example 64.

$^1$H NMR (300 MHz, DMSO-d$_6$) δ ppm 9.22 (s, 1H) 8.51 (d, J=2.49 Hz, 1H) 8.19 (dd, J=6.37, 2.12 Hz, 1H) 8.00 (dd, J=7.84, 1.83 Hz, 1H) 7.57 (d, J=8.64 Hz, 2H) 7.33-7.42 (m, 3H) 7.11 (dd, J=11.28, 8.35 Hz, 1H) 6.77-6.85 (m, 1H) 6.40 (br. s., 2H) 3.93-4.05 (m, 4H) 2.28 (s, 3H) 1.23 (t, J=7.03 Hz, 6H)

Example 66

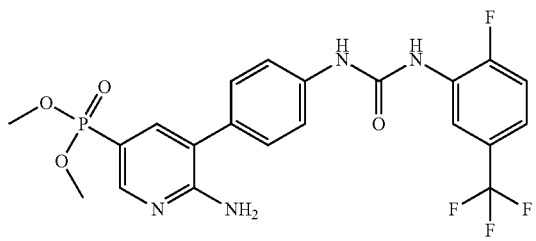

dimethyl {6-amino-5-[4-({[2-fluoro-5-(trifluoromethyl)phenyl]carbamoyl}amino)phenyl]pryidin-3-yl}phosphonate Synthesized using a procedure similar to Example 64.

$^1$H NMR (300 MHz, DMSO-d$_6$) δ ppm 9.36 (br. s., 1H) 8.95 (br. s., 1H) 8.63 (dd, J=7.33, 2.20 Hz, 1H) 8.19 (dd, J=6.37, 2.12 Hz, 1H) 7.55-7.61 (m, 2H) 7.51 (dd, J=10.99, 8.94 Hz, 1H) 7.36-7.44 (m, 4H) 6.45 (br. s., 2H) 3.66 (s, 3H) 3.62 (s, 3H)

Example 67

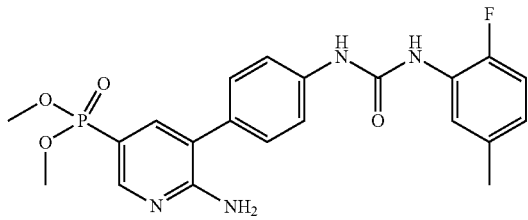

dimethyl [6-amino-5-(4-{[(2-fluoro-5-methylphenyl)carbamoyl]amino}phenyl)pryidin-3-yl]phosphonate Synthesized using a procedure similar to Example 64.
$^1$H NMR (300 MHz, DMSO-$d_6$) δ ppm 9.23 (s, 1H) 8.53 (d, J=1.90 Hz, 1H) 8.19 (dd, J=6.30, 2.05 Hz, 1H) 7.97-8.02 (m, 1H) 7.56 (d, J=8.50 Hz, 2H) 7.34-7.42 (m, 3H) 7.11 (dd, J=11.28, 8.50 Hz, 1H) 6.77-6.84 (m, 1H) 6.44 (br. s., 2H) 3.65 (s, 3H) 3.62 (s, 3H) 2.28 (s, 3H)

Example 63

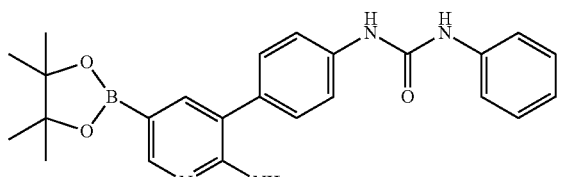

1-{4-[2-amino-5-(4,4,5,5-tetramethyl-1,3,2-dioxaborolan-2-yl)pyridin-3-yl]phenyl}-3-phenylurea Synthesized using a procedure similar to Example 62.
$^1$H NMR (600 MHz, DMSO-$d_6$) δ ppm 8.81 (br. s., 1H) 8.71 (br. s., 1H) 8.18 (d, J=1.76 Hz, 1H) 7.91-7.97 (m, 1H) 7.53-7.57 (m, 2H) 7.47 (d, J=7.92 Hz, 2H) 7.32-7.37 (m, 2H) 7.26-7.31 (m, 2H) 6.97 (t, J=7.34 Hz, 1H) 5.98 (br. s., 2H) 1.27 (s, 12H)

Example 59

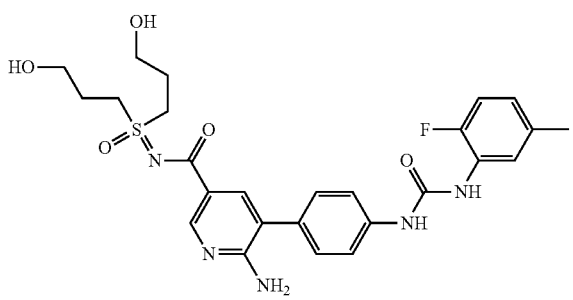

6-amino-N-[dimethyl(oxido)-λ$^4$-sulfanylidene]-5-[4-({[(2-fluoro-5-methylphenyl)amino]carbonyl}amino)phenyl]nicotinamide Synthesized using a procedure similar to Example 69.
$^1$H NMR (600 MHz, DMSO-$d_6$) δ ppm 9.22 (s, 1H) 8.56 (d, J=2.20 Hz, 1H) 8.53 (d, J=2.05 Hz, 1H) 8.00 (dd, J=7.78, 1.61 Hz, 1H) 7.74 (d, J=2.05 Hz, 1H) 7.56 (d, J=8.51 Hz, 2H) 7.36 (d, J=8.51 Hz, 2H) 7.11 (dd, J=11.30, 8.36 Hz, 1H) 6.79-6.83 (m, 1H) 6.24 (br. s., 2H) 4.73 (t, J=5.36 Hz, 2H) 3.54-3.66 (m, 4H) 3.51 (q, J=6.02 Hz, 4H) 2.28 (s, 3H) 1.83-1.95 (m, 4H)

Example 70

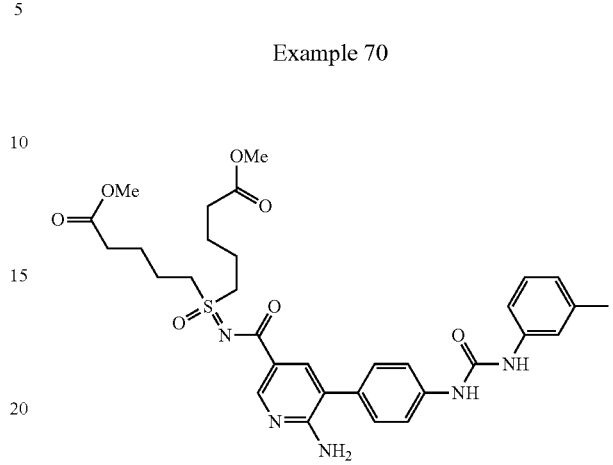

dimethyl 5,5'-(N-{[6-amino-5-(4-{[(3-methylphenyl)carbamoyl]amino}phenyl)pyridin-3-yl]carbonyl}sulfonimidoyl)dipentanoate Synthesized using a procedure similar to Example 69.
$^1$H NMR (600 MHz, DMSO-$d_6$) δ ppm 8.79 (s, 1H) 8.61 (s, 1H) 8.55 (d, J=2.20 Hz, 1H) 7.73 (d, J=2.05 Hz, 1H) 7.56 (d, J=8.66 Hz, 2H) 7.34 (d, J=8.51 Hz, 2H) 7.31 (s, 1H) 7.24 (d, J=8.36 Hz, 1H) 7.16 (t, J=7.78 Hz, 1H) 6.80 (d, J=7.34 Hz, 1H) 6.23 (br. s., 2H) 3.49-3.63 (m, 10H) 2.38 (t, J=7.26 Hz, 4H) 2.28 (s, 3H) 1.62-1.85 (m, 8H)

Example 71

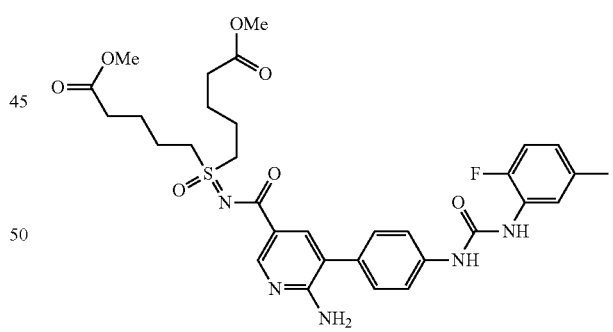

dimethyl 5,5'-(N-{[6-amino-5-(4-{[(2-fluoro-5-methylphenyl)carbamoyl]amino}phenyl)pyridin-3-yl]carbonyl}sulfonimidoyl)dipentanoate Synthesized using a procedure similar to Example 69.
$^1$H NMR (600 MHz, DMSO-$d_6$) δ ppm 9.19 (s, 1H) 8.55 (d, J=2.20 Hz, 1H) 8.50 (d, J=2.35 Hz, 1H) 8.00 (dd, J=7.92, 1.76 Hz, 1H) 7.74 (d, J=2.05 Hz, 1H) 7.56 (d, J=8.66 Hz, 2H) 7.35 (d, J=8.51 Hz, 2H) 7.11 (dd, J=11.30, 8.36 Hz, 1H) 6.79-6.83 (m, 1H) 6.24 (br. s., 2H) 3.50-3.62 (m, 10H) 2.38 (t, J=7.26 Hz, 4H) 2.28 (s, 3H) 1.63-1.84 (m, 8H)

Example 72

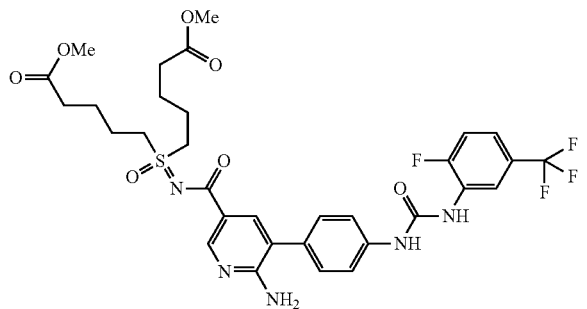

dimethyl 5,5'-[N-({6-amino-5-[4-({[(3-(trifuloromethyl)phenyl]carbamoyl}amino)phenyl]pyridin-3-yl}carbonyl)sulfonimidoyl]dipentanoate Synthesized using a procedure similar to Example 69.

$^1$H NMR (600 MHz, DMSO-d$_6$) δ ppm 9.08 (s, 1H) 8.95 (s, 1H) 8.55 (d, J=2.20 Hz, 1H) 8.03 (s, 1H) 7.74 (d, J=2.20 Hz, 1H) 7.56-7.61 (m, 3H) 7.52 (t, J=8.00 Hz, 1H) 7.36 (d, J=8.51 Hz, 2H) 7.32 (d, J=7.63 Hz, 1H) 6.24 (br. s., 2H) 3.50-3.62 (m, 10H) 2.38 (t, J=7.34 Hz, 4H) 1.72-1.84 (m, 4H) 1.64-1.70 (m, 4H)

Example 68

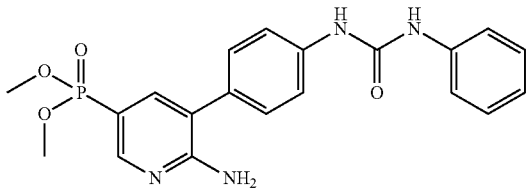

dimethyl (6-amino-5-{4-[(phenylcarbamoyl)amino]phenyl}pyridin-3-yl)phosphonate

Synthesized using a procedure similar to Example 64.

$^1$H NMR (300 MHz, DMSO-d$_6$) δ ppm 8.85 (s, 1H) 8.71 (s, 1H) 8.19 (dd, J=6.37, 2.12 Hz, 1H) 7.54-7.60 (m, 2H) 7.44-7.49 (m, 2H) 7.33-7.41 (m, 3H) 7.29 (t, J=7.91 Hz, 2H) 6.94-7.01 (m, 1H) 6.43 (br. s., 2H) 3.65 (s, 3H) 3.62 (s, 3H)

Example 62

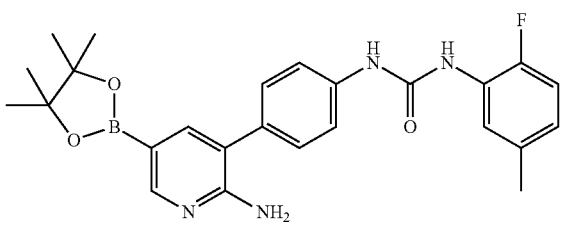

1-(4-(2-amino-5-(4,4,5,5-tetramethyl-1,3,2-dioxaborolan-2-yl)pyridin-3-yl)phenyl)-3-(2-fluoro-5-methylphenyl)urea To the nitrogen bubbled mixture of 1-(4-(2-amino-5-bromopyridin-3-yl)phenyl)-3-(2-fluoro-5-methylphenyl)urea (487 mg, 1.17 mmol, 1 eq), bis(pinacolato)diboron (0.36 g, 1.2 eq), and potassium acetate (0.46 g, 4 eq) in anhydrous 1,4-dioxane (6 mL) was added [1,1'-bis(diphenylphosphino)ferrocene]dichloropalladium(II) complex with dichloromethane (1:1) (0.14 g, 0.15 eq) and the mixture was heated at 120° C. for one and half hours. After the reaction was cooled to room temperature, it was filtered through a celite pad and washed with ethyl acetate. The filtrate was collected, washed sequentially with aqueous ammonium chloride, saturated aqueous sodium bicarbonate, brine, and lastly dried with anhydrous sodium sulfate. The upper clear solution was decanted, concentrated, and the brown oily residue was subject to a gradient column chromatography (EtOAc-Hex 1:4 to 4:1) to yield 1-(4-(2-amino-5-(4,4,5,5-tetramethyl-1,3,2-dioxaborolan-2-yl)pyridin-3-yl)phenyl)-3-(2-fluoro-5-methylphenyl)urea as a brown oil which solidified in vacuo in amount of 101 mg.

$^1$H NMR (600 MHz, DMSO-d$_6$) δ ppm 9.17 (s, 1H) 8.49 (br. s., 1H) 8.18 (d, J=1.76 Hz, 1H) 8.00 (d, J=7.92 Hz, 1H) 7.51-7.57 (m, 2H) 7.42 (d, J=1.76 Hz, 1H) 7.33-7.37 (m, 2H) 7.11 (dd, J=11.30, 8.36 Hz, 1H) 6.78-6.84 (m, 1H) 5.99 (s, 2H) 2.28 (s, 3H) 1.27 (s, 12H).

Example 61

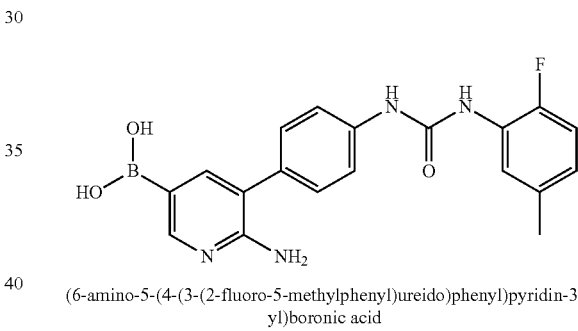

(6-amino-5-(4-(3-(2-fluoro-5-methylphenyl)ureido)phenyl)pyridin-3-yl)boronic acid To the solution of 1-(4-(2-amino-5-(4,4,5,5-tetramethyl-1,3,2-dioxaborolan-2-yl)pyridin-3-yl)phenyl)-3-(2-fluoro-5-methylphenyl)urea (AGN-227971, 108 mg, 0.234 mmol, 1 eq) in anhydrous tetrahydrofuran (2 mL) was added aq HCl (3N, 2 mL) and the reaction was first stirred at room temperature for two hours. Additional conc. HCl (0.5 mL) was dropwise added to the reaction and the mixture was stirred at 50° C. for further four hours. The reaction was then poured into saturated aqueous sodium bicarbonate and extracted with ethyl acetate. The organic layer was isolated, washed with brine, and dried with anhydrous sodium sulfate. The upper clear solution was decanted, concentrated to lesser amount, and the solid crashed-out was filtered. This solid was further purified by a reversed phase chromatography (from WATER-CH$_3$CN 9:1 to CH$_3$CN) to give (6-amino-5-(4-(3-(2-fluoro-5-methylphenyl)ureido)phenyl)pyridin-3-yl)boronic acid as a grey solid in amount of 7 mg.

$^1$H NMR (600 MHz, DMSO-d$_6$) δ ppm 9.15 (s, 1H) 8.48 (d, J=2.49 Hz, 1H) 8.31 (d, J=1.76 Hz, 1H) 8.00 (dd, J=7.85, 1.83 Hz, 1H) 7.80 (s, 2H) 7.68 (d, J=1.91 Hz, 1H) 7.52-7.56 (m, 2H) 7.34-7.38 (m, 2H) 7.11 (dd, J=11.30, 8.36 Hz, 1H) 6.78-6.83 (m, 1H) 5.71 (s, 2H) 2.28 (s, 3H)

Example 69

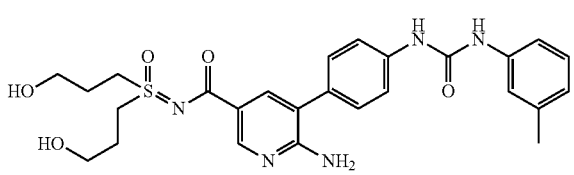

6-amino-N-[bis(3-hydroxypropyl)(oxido)-λ⁴-sulfanylidene]-5-[4-({[(3-methylphenyl)amino]carbonyl}amino)phenyl]nicotinamide To the solution of 6-amino-5-(4-aminophenyl)-N-[bis(3-hydroxypropyl)(oxido)-λ⁴-sulfanylidene]nicotinamide (39 mg, 0.1 mmol, 1.0 eq) in anhydrous THF (1 mL) was added 1-isocyanato-3-methylbenzene (0.013 mL, 1.0 eq) dropwise. The reaction was stirred at room temperature for 1 hour and then diluted with EtOAc. The organic layer was washed sequentially with saturated aq NaHCO₃, aq NH₄Cl, brine, and finally dried with anhydrous Na₂SO₄. The supernatant liquid was decanted, concentrated, and the oily residue was subject to a gradient column chromatography (EtOAc-Hex 7:1 to MeOH-EtOAc 1:9) yielding 6-amino-N-[bis(3-hydroxypropyl)(oxido)-λ⁴-sulfanylidene]-5-[4-({[(3-methylphenyl)amino]carbonyl}amino)phenyl]nicotinamide as a white solid in amount of 30 mg.

$^1$H NMR (600 MHz, DMSO-d$_6$) δ ppm 8.82 (br. s., 1H) 8.64 (br. s., 1H) 8.56 (d, J=2.05 Hz, 1H) 7.74 (d, J=2.05 Hz, 1H) 7.56 (d, J=8.51 Hz, 2H) 7.34 (d, J=8.22 Hz, 2H) 7.31 (s, 1H) 7.24 (d, J=7.63 Hz, 1H) 7.16 (t, J=7.78 Hz, 1H) 6.80 (d, J=7.34 Hz, 1H) 6.23 (br. s., 2H) 4.72 (t, J=5.28 Hz, 2H) 3.49-3.66 (m, 8H) 2.28 (s, 3H) 1.82-1.95 (m, 4H)

Example 74

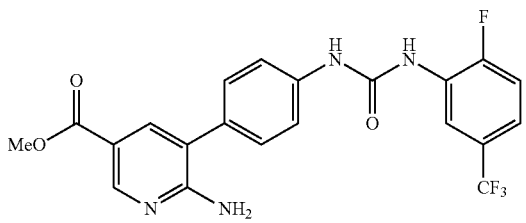

methyl 6-amino-5-[4-({[2-fluoro-5-(trifluoromethyl)phenyl]carbamoyl}amino)phenyl]pyridine-3-carboxylate To methyl 6-amino-5-(4-aminophenyl)nicotinate (0.18 mmoles) in 3 ml of tetrahydrofuran(THF) under nitrogen atmosphere was added a solution of 1-fluoro-2-isocyanato-4-(trifluoromethyl)benzene (0.22 mmoles, 1.2 equivalents) in 1 ml THF. The reaction was stirred at room temperature under nitrogen atmosphere for 30 minutes. Following this, the reaction was loaded onto silica and columned using ethyl acetate-hexanes, to give 25 mg of the product.

$^1$H NMR (dmso-d$^6$) δ: 9.29-9.34 (m, 1H), 8.92 (br. s., 1H), 8.60-8.65 (m, 1H), 8.51 (d, J=2.4 Hz, 1H), 7.68 (d, J=2.2 Hz, 1H), 7.57 (d, J=8.6 Hz, 2H), 7.46-7.52 (m, 1H), 7.38 (d, J=8.6 Hz, 3H), 6.52 (br. s., 2H), 3.78 (s, 3H)

Example 75

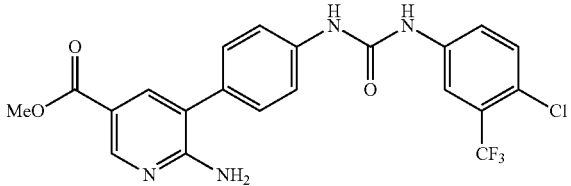

methyl 6-amino-5-[4-({[4-chloro-3-(trifluoromethyl)phenyl]carbamoyl}amino)phenyl]pyridine-3-carboxylate Synthesized using a procedure similar to methyl 6-amino-5-[4-({[2-fluoro-5-(trifluoromethyl)phenyl]carbamoyl}amino)phenyl]pyridine-3-carboxylate.

$^1$H NMR (dmso-d6) δ: 9.20-9.25 (m, 1H), 9.04 (s, 1H), 8.50 (d, J=2.2 Hz, 1H), 8.11 (d, J=2.4 Hz, 1H), 7.59-7.68 (m, 3H), 7.57 (d, J=8.6 Hz, 2H), 7.37 (d, J=8.6 Hz, 2H), 6.51 (br. s., 2H), 3.77 (s, 3H)

Example 73

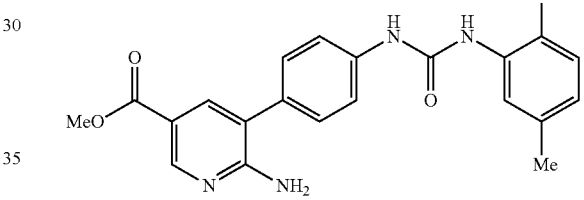

methyl 6-amino-5-(4-{[(2-fluoro-5-methylphenyl)carbamoyl]amino}phenyl)pyridine-3-carboxylate Synthesized using a procedure similar to methyl 6-amino-5-[4-({[2-fluoro-5-(trifluoromethyl)phenyl]carbamoyl}amino)phenyl]pyridine-3-carboxylate.

$^1$H NMR (dmso-d$^6$) δ: 9.21 (s, 1H), 8.50 (d, J=2.2 Hz, 2H), 7.97-8.01 (m, 1H), 7.67 (d, J=2.2 Hz, 1H), 7.54-7.57 (m, 2H), 7.36 (d, J=8.6 Hz, 2H), 7.10 (dd, J=11.5, 8.3 Hz, 1H), 6.77-6.82 (m, 1H), 6.51 (br. s., 2H), 3.78 (s, 3H), 2.27 (s, 3H).

Example 76

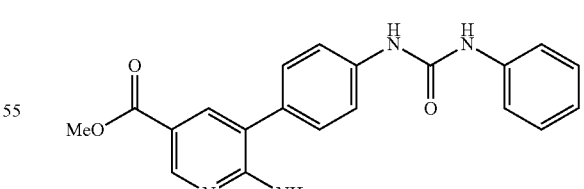

methyl 6-amino-5-{4-[(phenylcarbamoyl)amino]phenyl}pyridine-3-carboxylate

Synthesized using a procedure similar to methyl 6-amino-5-[4-({[2-fluoro-5-(trifluoromethyl)phenyl]carbamoyl}amino)phenyl]pyridine-3-carboxylate.

$^1$H NMR (dmso-d$^6$) δ: 8.81 (s, 1H), 8.68 (s, 1H), 8.50 (d, J=2.2 Hz, 1H), 7.66-7.68 (m, 1H), 7.54-7.57 (m, J=8.6 Hz, 2H), 7.46 (dd, J=8.6, 1.0 Hz, 2H), 7.35 (d, J=8.6 Hz, 2H), 7.28 (t, J=7.9 Hz, 2H), 6.97 (t, J=7.4 Hz, 1H), 6.51 (br. s., 2H), 3.77 (s, 3H).

Biological data for the compounds of the present invention was generated by use of the following assays.

VEGFR2 Kinase Assay

Biochemical KDR kinase assays were performed in 96 well microtiter plates that were coated overnight with 75 μg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 2.7 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of 0-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

VEGFR2 Cellular Assay

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 384-well fibronectin coated black-walled plates overnight @ 37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 uM) or at concentrations ranging from 0.0001 to 10.0 uM followed by $VEGF_{165}$ stimulation (10 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of VEGF stimulated responses in the absence of inhibitor.

PDGFRβ Kinase Assay

Biochemical PDGFRβ kinase assays were performed in 96 well microtiter plates that were coated overnight with 75 μg of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 36 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain PDGFR-b protein (Millipore). Following a 60 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 ρl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

PDGFRβ Cellular Assay

Automated FLIPR (Fluorometric Imaging Plate Reader) technology was used to screen for inhibitors of PDGF-induced increases in intracellular calcium levels in fluorescent dye loaded endothelial cells. NHDF-Ad (Normal Human Dermal Fibroblasts, Adult; Lonza) were seeded in 384-well fibronectin coated black-walled plates overnight @ 37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 uM) or at concentrations ranging from 0.0001 to 10.0 uM followed by PDGF-BB stimulation (30 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of PDGF-BB stimulated responses in the absence of inhibitor.

PKR KinaseGlo Assay

Commercially available recombinant human GST-PKR (SignalChem, Canada; 1.5 uM-2 uM stock) is diluted to 500 nM in assay buffer (20 mM Tris-HCl, pH 7.2, 10 mM KCl, 10 mM MgCl2, 10% glycerol). Preactivated PKR is dispensed to 384/96-well black plates at 3.125/12.5 uls/well using the liquid handler Janus. Appropriate dilutions of inhibitors are added to 384/96-well plate followed by 6.6 uM ATP (final) and incubated for 10 minutes at room temperature. The remaining ATP/well is determined by adding 6.25/25 uls/well Kinase-Glo assay mix (Promega) and luminescence is measured on EnVision luminescence plate reader (integration time, 0.2 sec; Perkin-Elmer, Massachusetts, USA). The % inhibition for the compounds is calculated using ATP only (100% inhibition) and PKR+ATP (0% inhibition). 1050 values are determined by plotting % activity versus inhibitor concentration. Curves are fitted using Activity base XLfit (IDBS, UK) using the formula—

4 Parameter Logistic Model $$\text{fit}=(A+((B-A)/(1+(10^{((C-x)*D)}))))$$

$$\text{inv}=(C-(\log(((B-A)/(y-A))-1)/D))$$

$$\text{res}=(y-\text{fit})$$

The biological results for the various compounds are shown in Tables 2, 3, 4, 5, 6, 7, 8, 9, 10, 11 and 12 below.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered orally, subcutaneously, intravenously, intrathecally or some suitable combination(s) thereof.

In addition to the common dosage forms set out above, the compounds of this invention may also be administered by controlled release means and/or delivery devices such as those described in U.S. Pat. Nos. 3,845,770; 3,916,899; 3,536,809; 3,598,123; 3,630,200; 4,008,719; and 5,366,738.

For use where a composition for intravenous administration is employed, a suitable daily dosage range for anti-inflammatory, anti-atherosclerotic or anti-allergic use is from about 0.001 mg to about 25 mg (preferably from 0.01 mg to about 1 mg) of a compound of this invention per kg of body weight per day and for cytoprotective use from about 0.1 mg to about 100 mg (preferably from about 1 mg to about 100 mg and more preferably from about 1 mg to about 10 mg) of a compound of this invention per kg of body weight per day. For the treatment of diseases of the eye, ophthalmic preparations for ocular administration comprising 0.001-1% by weight solutions or suspensions of the compounds of this invention in an acceptable ophthalmic formulation may be used.

Preferably, the pharmaceutical preparation is in a unit dosage form. In such form, the preparation is subdivided into suitably sized unit doses containing appropriate quantities of the active component, e.g., an effective amount to achieve the desired purpose.

The magnitude of prophylactic or therapeutic dose of a compound of this invention will, of course, vary with the nature of the severity of the condition to be treated and with the particular compound and its route of administration. It will also vary according to the age, weight and response of the individual patient. It is understood that a specific daily dosage amount can simultaneously be both a therapeutically effective amount, e.g., for treatment to slow progression of an existing condition, and a prophylactically effective amount, e.g., for prevention of condition.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the compounds of the present invention. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

In one aspect, the present invention provides a kit comprising a therapeutically effective amount of at least one compound of the present invention, or a pharmaceutically acceptable salt of said compound and a pharmaceutically acceptable carrier, vehicle or diluents, and directions for the use of said kit.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

TABLE 2

Sulfoximine/Urea

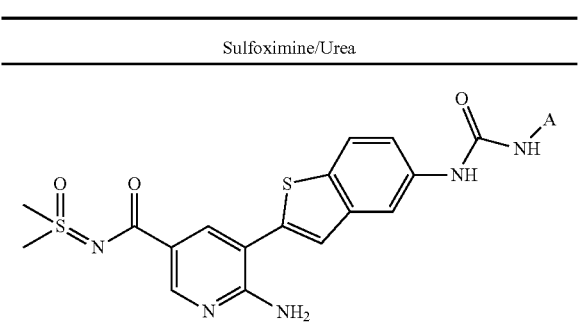

| Example | A | VEGFR2 Enzyme Assay (IC$_{50}$ nM) | VEGFR2 Cellular Assay (IC$_{50}$ nM) | PDGFRβ Enzyme Assay (IC$_{50}$ nM) |
|---|---|---|---|---|
| 1 | 3-methylphenyl | 8 | 20 | 20 |
| 2 | 4-F, 3-Cl phenyl | 3 | 25 | 17 |
| 3 | 5-methyl-2-F phenyl | 8 | 3 | 17 |
| 4 | phenyl | 42 | 68 | 73 |
| 5 | 3-CF$_3$, 4-Cl phenyl | 6 | 11 | 21 |
| 6 | 5-CF$_3$, 2-F phenyl | 6 | 5 | 27 |

TABLE 3

Ester/Urea

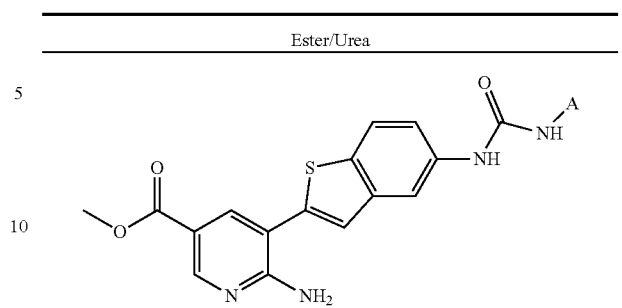

| Example | A | VEGFR2 Enzyme Assay (IC$_{50}$ nM) | VEGFR2 Cellular Assay (IC$_{50}$ nM) | PDGFRβ Enzyme Assay (IC$_{50}$ nM) |
|---|---|---|---|---|
| 7 | 3-CF$_3$ phenyl | 7 | 22 | 11 |
| 8 | 5-CF$_3$, 2-F phenyl | 10 | 12 | 24 |
| 9 | 3-CF$_3$, 4-Cl phenyl | 15 | 63 | 45 |
| 10 | 5-methyl-2-F phenyl | 17 | 27 | 15 |
| 11 | 5-methyl-2-F-3-... phenyl | 20 | 328 | 18 |
| 12 | 3-Cl, 4-F phenyl | 21 | 355 | 26 |

TABLE 3-continued
Ester/Urea
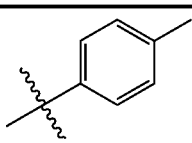
| Example | A | VEGFR2 Enzyme Assay (IC$_{50}$ nM) | VEGFR2 Cellular Assay (IC$_{50}$ nM) | PDGFRβ Enzyme Assay (IC$_{50}$ nM) |
| --- | --- | --- | --- | --- |
| 13 | 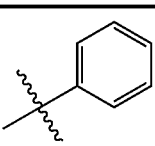 | 45 | 941 | 12 |
| 14 | 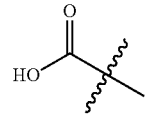 | 81 | 1595 | 10 |
| 15 | 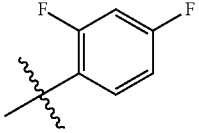 [SMILES: *c1ccc(F)cc1F] | 137 | 1352 | 28 |
| 16 | 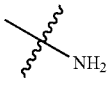 | NA | NA | 9 |
TABLE 4
Acid or Amide/Urea
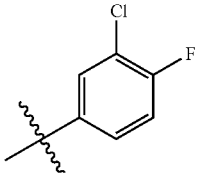 [SMILES: *c1ccc(F)c(Cl)c1]
| Example | Y | Z | A | VEGFR2 Enzyme Assay (IC$_{50}$ nM) | VEGFR2 Cellular Assay (IC$_{50}$ nM) | PDGFRβ Enzyme Assay (IC$_{50}$ nM) |
| --- | --- | --- | --- | --- | --- | --- |
| 17 | 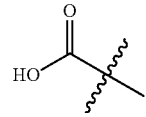 | 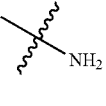 | 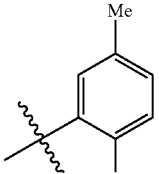 | 41 | N/A | N/A |
| 18 | 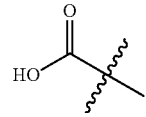 | 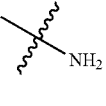 | 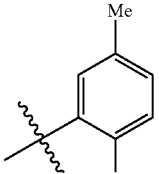 | 38 | N/A | N/A |

TABLE 4-continued
Acid or Amide/Urea
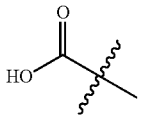
| Example | Y | Z | A | VEGFR2 Enzyme Assay (IC$_{50}$ nM) | VEGFR2 Cellular Assay (IC$_{50}$ nM) | PDGFRβ Enzyme Assay (IC$_{50}$ nM) |
|---|---|---|---|---|---|---|
| 19 | 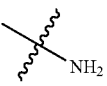 | 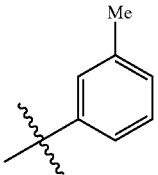 [SMILES: *c1cccc(C)c1] | 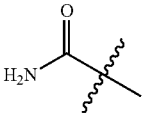 | 120 | N/A | 431 |
| 20 |  | 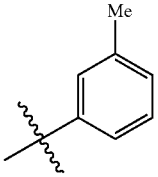 [SMILES: *c1cccc(C)c1] | 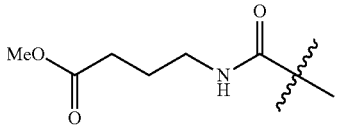 [SMILES: *C(=O)NCCCC(=O)OC] | 35 | N/A | N/A |
| 21 | 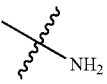 | 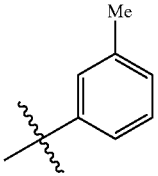 [SMILES: *c1cccc(C)c1] | 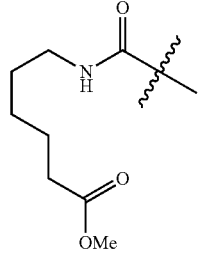 [SMILES: *C(=O)NCCCCCC(=O)OC] | 118 | N/A | N/A |
| 22 | 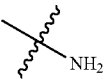 | 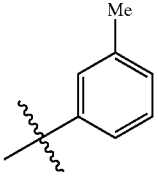 [SMILES: *c1cccc(C)c1] | | 132 | N/A | N/A |

TABLE 5

Boronate Ester/Urea

| Example | A | VEGFR2 Enzyme Assay (IC₅₀ nM) | VEGFR2 Cellular Assay (IC₅₀ nM) | PDGFRβ Enzyme Assay (IC₅₀ nM) |
|---|---|---|---|---|
| 23 | 2-F, 5-CF₃-phenyl | 10 | N/A | 17 |
| 24 | 3-CF₃-phenyl | 13 | N/A | N/A |
| 25 | 4-Cl, 3-CF₃-phenyl | 16 | N/A | 21 |
| 26 | 2-F, 5-Me-phenyl | 25 | N/A | 10 |
| 27 | 3-Cl, 4-F-phenyl | 37 | N/A | N/A |
| 28 | 3-Et-phenyl | 42 | N/A | 18 |
| 29 | 3-Me-phenyl | 54 | N/A | 20 |
| 30 | phenyl | 301 | N/A | 130 |

TABLE 6

Boronic Acid/Urea

| Example | A | VEGFR2 Enzyme Assay (IC₅₀ nM) | VEGFR2 Cellular Assay (IC₅₀ nM) | PDGFRβ Enzyme Assay (IC₅₀ nM) |
|---|---|---|---|---|
| 31 | 3-Me-phenyl | 93 | N/A | 42 |
| 32 | phenyl | 378 | N/A | 138 |

TABLE 7

Sulfoximine/Amide

| Example | Q | VEGFR2 Enzyme Assay (IC$_{50}$ nM) | VEGFR2 Cellular Assay (IC$_{50}$ nM) | PDGFRβ Enzyme Assay (IC$_{50}$ nM) |
|---|---|---|---|---|
| 33 | 3-methyl-furan-2-yl | 17 | 6 | 457 |
| 34 | 4-chloro-3-(trifluoromethyl)phenyl | 32 | 277 | 36 |
| 35 | 4-fluoro-3-methylphenyl | 50 | 45 | 258 |
| 36 | phenyl | 51 | N/A | N/A |
| 37 | 3-methylphenyl | 53 | N/A | 131 |
| 38 | 4-fluoro-3-(trifluoromethyl)phenyl | 178 | 1023 | 128 |

TABLE 8

Ester/Amide

| Example | Y | Q | VEGFR2 Enzyme Assay (IC$_{50}$ nM) | VEGFR2 Cellular Assay (IC$_{50}$ nM) | PDGFRβ Enzyme Assay (IC$_{50}$ nM) |
|---|---|---|---|---|---|
| 39 | MeO-C(O)-C(Me)$_2$- | 3-methyl-furan-2-yl | 31 | 75 | 61 |

TABLE 8-continued
Ester/Amide
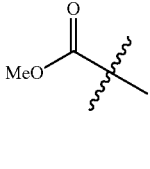
| Example | Y | Q | VEGFR2 Enzyme Assay (IC$_{50}$ nM) | VEGFR2 Cellular Assay (IC$_{50}$ nM) | PDGFRβ Enzyme Assay (IC$_{50}$ nM) |
|---|---|---|---|---|---|
| 40 | 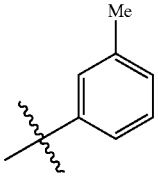 [SMILES: *c1cccc(C)c1] | 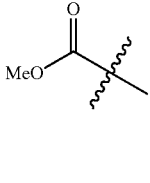 | 57 | 145 | 25 |
| 41 | 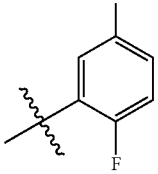 | 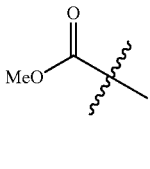 | 199 | 1102 | 38 |
| 42 | 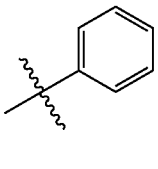 | 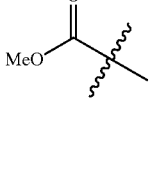 | 224 | 3945 | 503 |
| 43 | 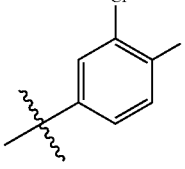 | 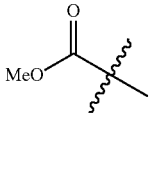 | 264 | 2488 | 25 |
| 44 | 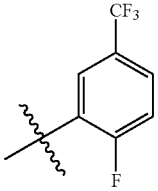 [SMILES: *c1cc(C(F)(F)F)ccc1F] | 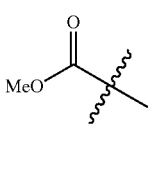 | 930 | 8722 | 29 |
| 45 | 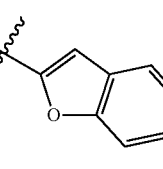 | | N/A | N/A | 936 |

TABLE 8-continued
Ester/Amide
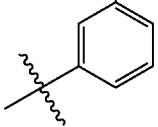 [SMILES: *c1ccccc1]
| Example | Y | Q | VEGFR2 Enzyme Assay (IC$_{50}$ nM) | VEGFR2 Cellular Assay (IC$_{50}$ nM) | PDGFRβ Enzyme Assay (IC$_{50}$ nM) |
|---|---|---|---|---|---|
| 46 | H | Me- (3-methylphenyl) | 1171 | 5110 | 1278 |
| 47 | H | phenyl | 1488 | 1815 | N/A |
TABLE 9
Reverse Amides
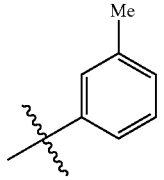 [SMILES: *c1cccc(C)c1]
| Example | T | VEGFR2 Enzyme Assay (IC$_{50}$ nM) | VEGFR2 Cellular Assay (IC$_{50}$ nM) | PDGFRβ Enzyme Assay (IC$_{50}$ nM) |
|---|---|---|---|---|
| 48 | Me- (3-methylphenyl) | 3570 | N/A | >10,000 |

TABLE 10

Other Sulfoximine substituents/Ureas

| Example | Y | A | VEGFR2 Enzyme Assay (IC$_{50}$ nM) | VEGFR2 Cellular Assay (IC$_{50}$ nM) | PDGFRβ Enzyme Assay (IC$_{50}$ nM) |
|---|---|---|---|---|---|
| 53 | MeO-C(O)-(CH₂)₃-S(O)(Me)=N- | 3-Me-phenyl | 5 | N/A | 16 |
| 54 | MeO-C(O)-(CH₂)₃-S(O)(Me)=N- | 4-F-3-Me-phenyl | 3 | N/A | N/A |
| 55 | MeO-C(O)-(CH₂)₃-S(O)(Me)=N- | 3-Cl-4-F-phenyl | 4 | N/A | N/A |
| 56 | (HO-(CH₂)₃)₂-S(O)=N- | 3-Me-phenyl | 8 | N/A | 8 |

TABLE 11
PKR data for Pyridyl Benzothiophenes
| Example | Structure | PKR KINASEGLO Enzyme Assay IC50 (nM) |
|---|---|---|
| 5 | 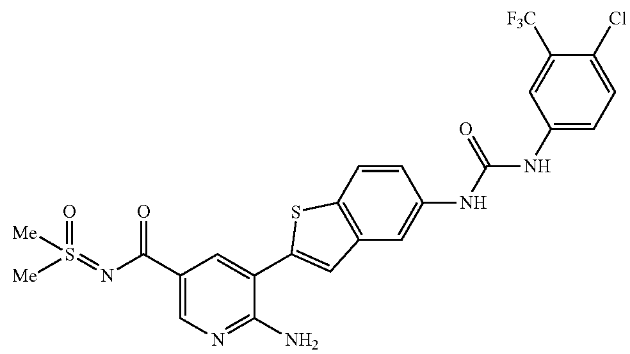 [SMILES: CS(C)(=O)=NC(=O)c1cnc(N)c(-c2cc3cc(NC(=O)Nc4ccc(Cl)c(C(F)(F)F)c4)ccc3s2)c1] | 69 |
| 6 | 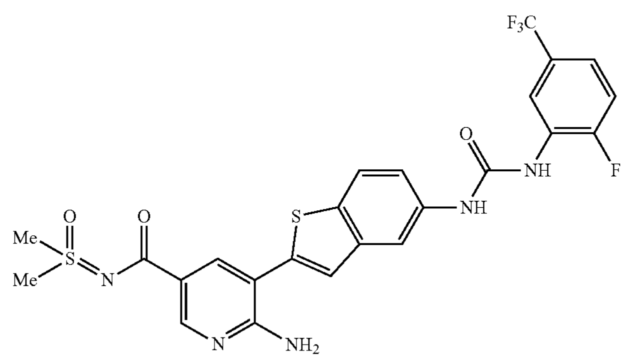 [SMILES: CS(C)(=O)=NC(=O)c1cnc(N)c(-c2cc3cc(NC(=O)Nc4cc(C(F)(F)F)ccc4F)ccc3s2)c1] | 167 |
TABLE 12
| Example | Structure | VEGFR2 Enzyme Assay (IC$_{50}$ nM) | PKR KINASEGLO Enzyme Assay IC50 (nM) |
|---|---|---|---|
| 57 | 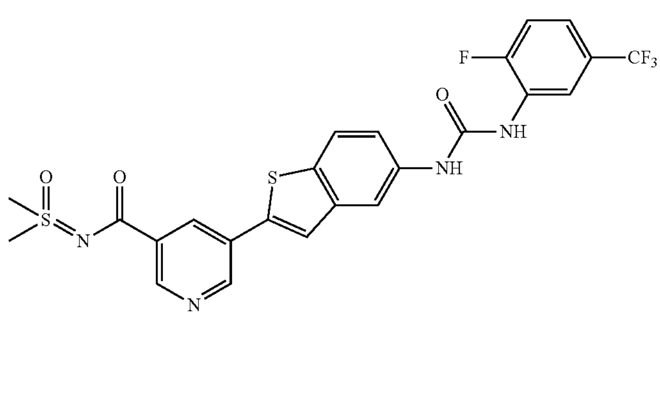 [SMILES: CS(C)(=O)=NC(=O)c1cncc(-c2cc3cc(NC(=O)Nc4cc(C(F)(F)F)ccc4F)ccc3s2)c1] | 7 | 551 |

TABLE 12-continued

| Example | Structure | VEGFR2 Enzyme Assay (IC$_{50}$ nM) | PKR KINASEGLO Enzyme Assay IC50 (nM) |
|---|---|---|---|
| 58 | 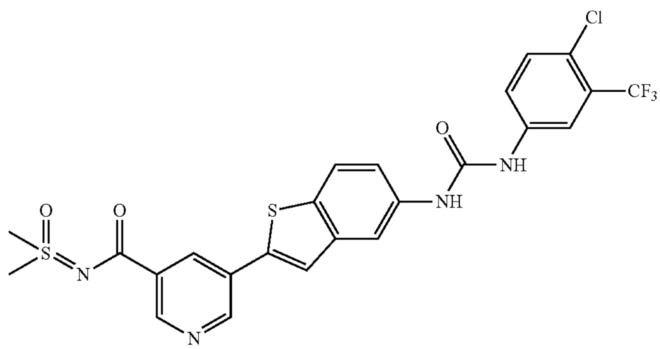 [SMILES: CS(C)(=O)=NC(=O)c1cncc(-c2cc3cc(NC(=O)Nc4ccc(Cl)c(C(F)(F)F)c4)ccc3s2)c1] | 14 | 390 |

TABLE 13

| Example Number | Structure | VEGFR2 Kinase IC$_{50}$ nM | VEGFR2 Cellular IC$_{50}$ nM | PDGFRβ Kinase IC$_{50}$ nM | PDGFRβ Cellular IC$_{50}$ nM |
|---|---|---|---|---|---|
| 59 | 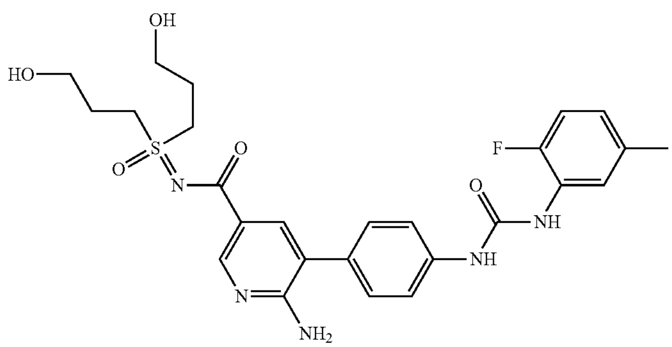 [SMILES: Cc1ccc(F)c(NC(=O)Nc2ccc(-c3cc(C(=O)N=S(=O)(CCCO)CCCO)cnc3N)cc2)c1] | 26 | na | 100 | na |
| 60 | 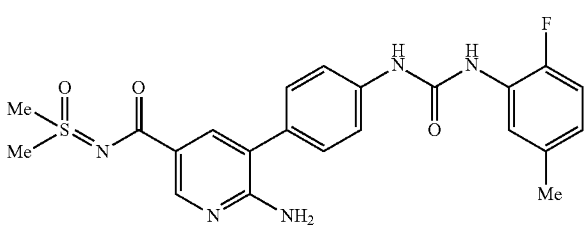 [SMILES: Cc1ccc(F)c(NC(=O)Nc2ccc(-c3cc(C(=O)N=S(C)(C)=O)cnc3N)cc2)c1] | 6 | 12 | na | na |
| 61 | 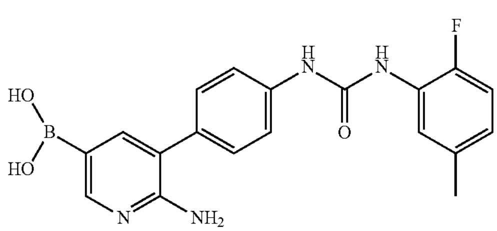 [SMILES: Cc1ccc(F)c(NC(=O)Nc2ccc(-c3cc(B(O)O)cnc3N)cc2)c1] | 25 | na | 58 | 150 |

TABLE 13-continued

| Example Number | Structure | VEGFR2 Kinase IC$_{50}$ nM | VEGFR2 Cellular IC$_{50}$ nM | PDGFRβ Kinase IC$_{50}$ nM | PDGFRβ Cellular IC$_{50}$ nM |
| --- | --- | --- | --- | --- | --- |
| 62 | 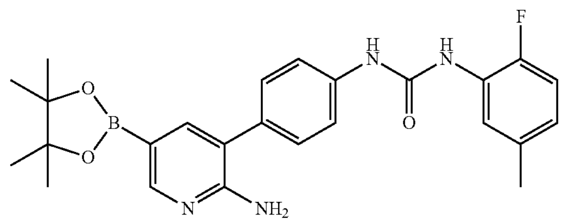 [SMILES: Cc1ccc(F)c(NC(=O)Nc2ccc(-c3cc(B4OC(C)(C)C(C)(C)O4)cnc3N)cc2)c1] | 53 | na | 24 | na |
| 63 | 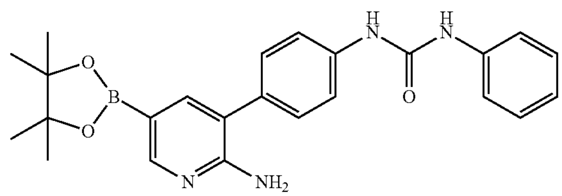 [SMILES: CC1(C)OB(c2cnc(N)c(-c3ccc(NC(=O)Nc4ccccc4)cc3)c2)OC1(C)C] | 206 | na | na | na |
| 64 | 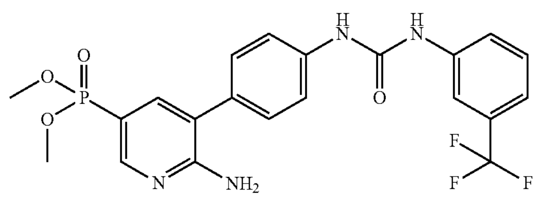 [SMILES: COP(=O)(OC)c1cnc(N)c(-c2ccc(NC(=O)Nc3cccc(C(F)(F)F)c3)cc2)c1] | 57 | 10 | na | 66 |
| 65 | 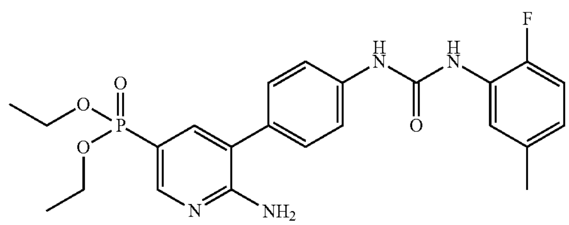 [SMILES: CCOP(=O)(OCC)c1cnc(N)c(-c2ccc(NC(=O)Nc3cc(C)ccc3F)cc2)c1] | 99 | 35 | 82 | 118 |
| 66 | 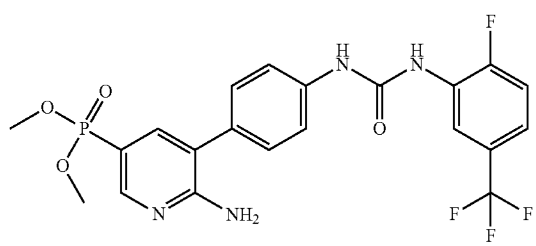 [SMILES: COP(=O)(OC)c1cnc(N)c(-c2ccc(NC(=O)Nc3cc(C(F)(F)F)ccc3F)cc2)c1] | 115 | 25 | na | na |
| 67 | 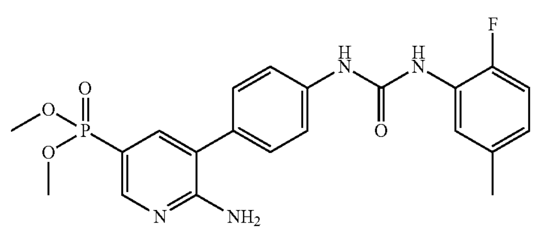 [SMILES: COP(=O)(OC)c1cnc(N)c(-c2ccc(NC(=O)Nc3cc(C)ccc3F)cc2)c1] | 133 | 30 | na | na |
| 68 | 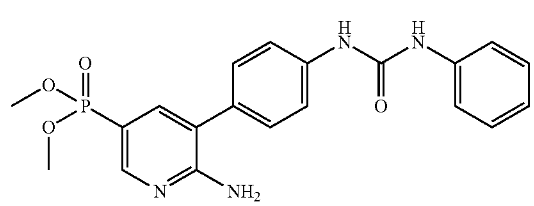 [SMILES: COP(=O)(OC)c1cnc(N)c(-c2ccc(NC(=O)Nc3ccccc3)cc2)c1] | 891 | na | na | na |

TABLE 13-continued

| Example Number | Structure | VEGFR2 Kinase IC$_{50}$ nM | VEGFR2 Cellular IC$_{50}$ nM | PDGFRβ Kinase IC$_{50}$ nM | PDGFRβ Cellular IC$_{50}$ nM |
|---|---|---|---|---|---|
| 69 | 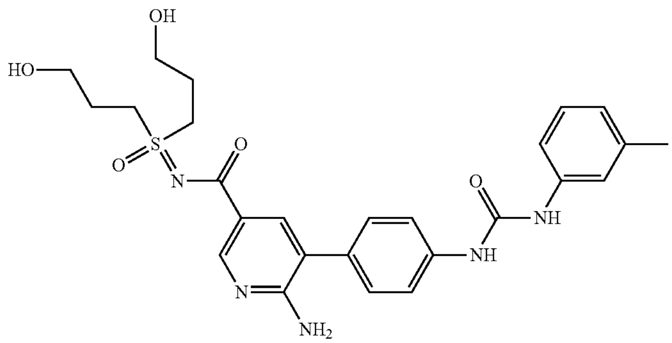 [SMILES: Cc1cccc(NC(=O)Nc2ccc(-c3cc(C(=O)N=S(=O)(CCCO)CCCO)cnc3N)cc2)c1] | 13 | na | 83 | na |
| 70 | 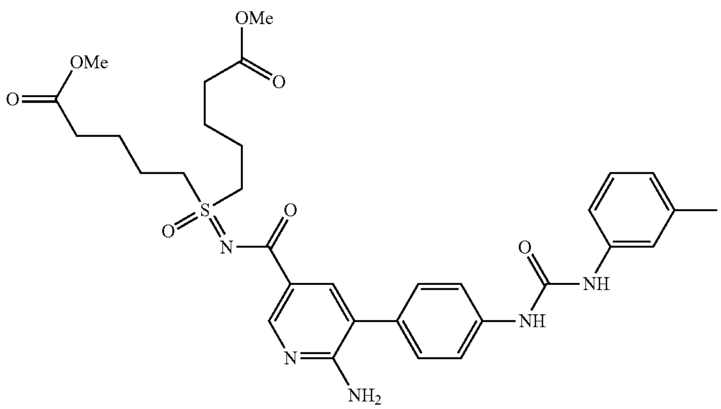 [SMILES: COC(=O)CCCCS(=O)(CCCCC(=O)OC)=NC(=O)c1cnc(N)c(-c2ccc(NC(=O)Nc3cccc(C)c3)cc2)c1] | 14 | 3 | 138 | 173 |
| 71 | 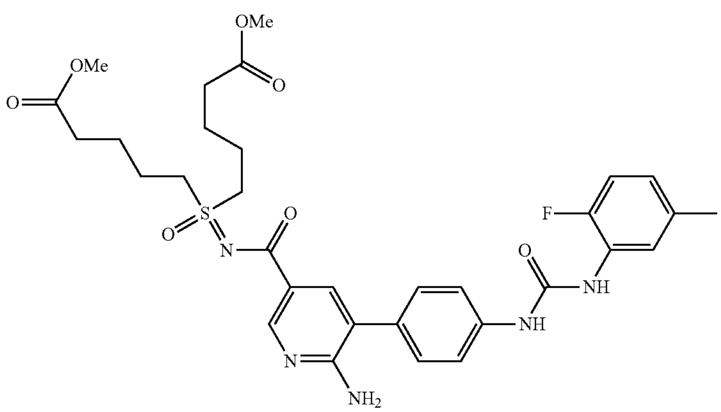 [SMILES: COC(=O)CCCCS(=O)(CCCCC(=O)OC)=NC(=O)c1cnc(N)c(-c2ccc(NC(=O)Nc3cc(C)ccc3F)cc2)c1] | 33 | 13 | 88 | 141 |
| 72 | 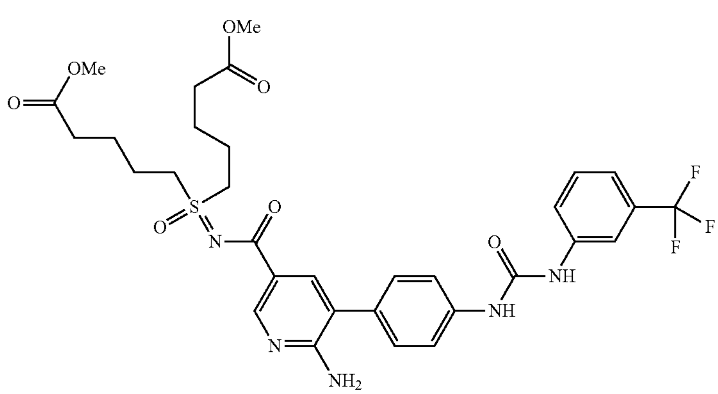 [SMILES: COC(=O)CCCCS(=O)(CCCCC(=O)OC)=NC(=O)c1cnc(N)c(-c2ccc(NC(=O)Nc3cccc(C(F)(F)F)c3)cc2)c1] | 42 | 11 | 13 | 192 |

TABLE 13-continued

| Example Number | Structure | VEGFR2 Kinase IC$_{50}$ nM | VEGFR2 Cellular IC$_{50}$ nM | PDGFRβ Kinase IC$_{50}$ nM | PDGFRβ Cellular IC$_{50}$ nM |
|---|---|---|---|---|---|
| 73 | 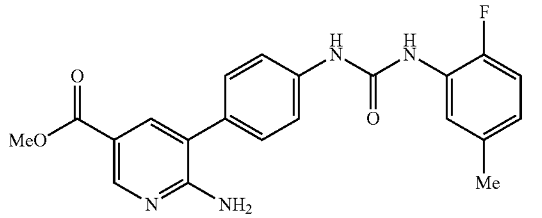 [SMILES: COC(=O)c1cnc(N)c(-c2ccc(NC(=O)Nc3cc(C)ccc3F)cc2)c1] | 9 | 14 | na | na |
| 74 | 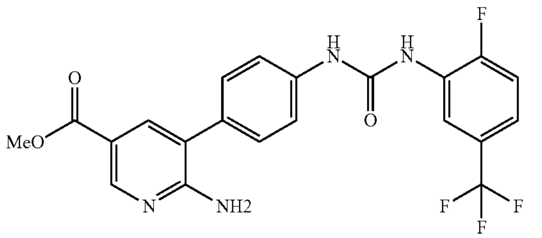 [SMILES: COC(=O)c1cnc(N)c(-c2ccc(NC(=O)Nc3cc(C(F)(F)F)ccc3F)cc2)c1] | 7 | 41 | na | na |
| 75 | 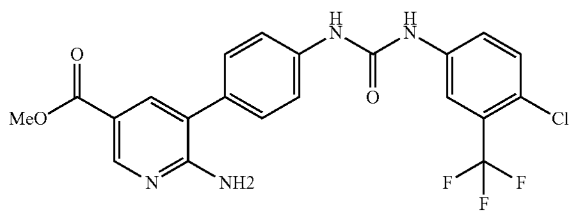 [SMILES: COC(=O)c1cnc(N)c(-c2ccc(NC(=O)Nc3ccc(Cl)c(C(F)(F)F)c3)cc2)c1] | 7 | 74 | na | na |
| 76 | 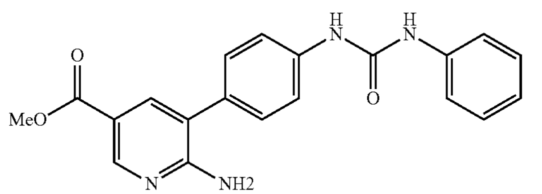 [SMILES: COC(=O)c1cnc(N)c(-c2ccc(NC(=O)Nc3ccccc3)cc2)c1] | 29 | 115 | na | na |

What is claimed is:

1. A compound represented by Formula I, its enantiomers, diastereoisomers, or a pharmaceutically acceptable salt thereof:

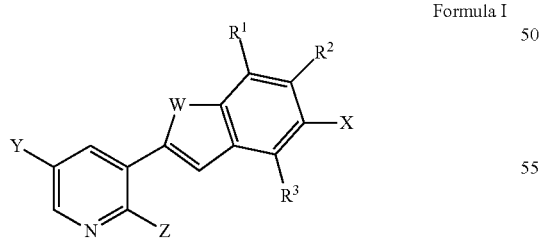

Formula I wherein:
W is S;
R$^1$ is hydrogen, C$_{1-8}$ alkyl, halo or haloalkyl;
R$^2$ is —N(R$^4$)C(O)N(R$^4$R$^5$), —N(R$^4$)C(O)R$^5$, —C(O)N(R$^4$R$^5$), hydrogen, C$_{1-8}$ alkyl, halo or haloalkyl;
R$^3$ is hydrogen, C$_{1-8}$ alkyl, halo or haloalkyl;
X is —N(R$^4$)C(O)N(R$^4$R$^5$), —N(R$^4$)C(O)R$^5$, or —C(O)N(R$^4$R$^5$);
R$^4$ is hydrogen or alkyl;
R$^5$ is phenyl, optionally substituted with one or more substituents selected from the group consisting of methyl, ethyl, fluoro, chloro, and trifluoromethyl;
Y is hydrogen, —C(O)—N=S(O)R$^7$R$^6$, —N(R$^4$)C(O)R$^8$, —COOR$^9$, —C(O)NHR$^{10}$, —B(OH)$_2$, —B(OR$^{12}$)(OR$^{13}$) or

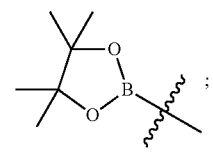

R$^7$ is C$_{1-8}$ alkyl optionally substituted with one or more substituents selected from the group consisting of hydroxyl and —COOCH$_3$, or R$^7$ is aryl;
R$^6$ is C$_{1-8}$ alkyl optionally substituted with one or more substituents selected from the group consisting of hydroxyl and —COOCH$_3$, or R$^6$ is aryl;
R$^8$ is C$_{1-8}$ alkyl optionally substituted with one or more substituents selected from the group consisting of —COOCH$_3$, or R$^8$ is aryl;

R⁹ is hydrogen, C₁₋₈ alkyl, or R⁹ is aryl;
R¹⁰ is hydrogen, C₁₋₈ alkyl optionally substituted with one or more substituents selected from the group consisting of —COOCH₃, or R¹⁰ is aryl;
Z is —NHR¹¹;
R¹¹ is hydrogen or C₁₋₈ alkyl;
R¹² is hydrogen or C₁₋₈ alkyl; and
R¹³ is hydrogen or C₁₋₈ alkyl.

2. The compound according to claim 1, wherein:
R¹ is hydrogen;
R² is hydrogen;
R³ is hydrogen;
X is —N(R⁴)C(O)N(R⁴R⁵), —N(R⁴)C(O)R⁵, or —C(O)N(R⁴R⁵);
Y is hydrogen, —C(O)—N═S(O)R⁷R⁶, —COOR⁹, —C(O)NHR¹⁰, —B(OH)₂, or

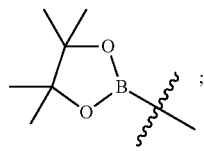

R⁷ is C₁₋₈ alkyl optionally substituted with one or more substituents selected from the group consisting of hydroxyl and —COOCH₃;
R⁶ is C₁₋₈ alkyl optionally substituted with one or more substituents selected from the group consisting of hydroxyl and —COOCH₃;
R⁹ is hydrogen or C₁₋₈ alkyl; and
R¹⁰ is hydrogen or C₁₋₈ alkyl optionally substituted with one or more substituents selected from the group consisting of —COOCH₃.

3. The compound according to claim 1, wherein:
R¹ is hydrogen;
R² is hydrogen;
R³ is hydrogen;
X is —N(R⁴)C(O)N(R⁴R⁵);
Y is hydrogen, —C(O)—N═S(O)R⁷R⁶, —COOR⁹, —C(O)NHR¹⁰, —B(OH)₂, or

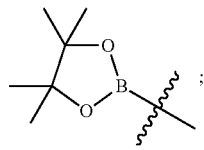 [SMILES: *B1OC(C)(C)C(C)(C)O1]

R⁷ is C₁₋₈ alkyl optionally substituted with one or more substituents selected from the group consisting of hydroxyl and —COOCH₃;
R⁶ is C₁₋₈ alkyl optionally substituted with one or more substituents selected from the group consisting of hydroxyl and —COOCH₃.

4. The compound according to claim 1, wherein:
R¹ is hydrogen;
R² is hydrogen;
R³ is hydrogen;
X is —N(R⁴)C(O)N(R⁴R⁵);
Y is —C(O)—N═S(O)R⁷R⁶,
R⁷ is C₁₋₈ alkyl optionally substituted with one or more substituents selected from the group consisting of hydroxyl and —COOCH₃;
R⁶ is C₁₋₈ alkyl optionally substituted with one or more substituents selected from the group consisting of hydroxyl and —COOCH₃.

5. The compound according to claim 1, wherein:
R¹ is hydrogen;
R² is hydrogen;
R³ is hydrogen;
X is —N(R⁴)C(O)N(R⁴R⁵);
Y is —C(O)—N═S(O)R⁷R⁶;
R⁷ is C₁₋₈ alkyl optionally substituted with one or more substituents selected from the group consisting of hydroxyl and —COOCH₃;
R⁶ is C₁₋₈ alkyl optionally substituted with one or more substituents selected from the group consisting of hydroxyl and —COOCH₃; and
R¹¹ is hydrogen.

6. The compound according to claim 1, wherein:
R¹ is hydrogen;
R² is hydrogen;
R³ is hydrogen;
X is —N(R⁴)C(O)N(R⁴R⁵);
R⁴ is hydrogen; and
Y is —C(O)—N═S(O)R⁷R⁶.

7. The compound according to claim 1, wherein:
R¹ is hydrogen;
R² is hydrogen;
R³ is hydrogen;
X is —N(R⁴)C(O)N(R⁴R⁵);
R⁴ is hydrogen;
Y is —C(O)—N═S(O)R⁷R⁶;
R⁷ is C₁₋₈ alkyl optionally substituted with one or more substituents selected from the group consisting of hydroxyl and —COOCH₃; and
R⁶ is C₁₋₈ alkyl optionally substituted with one or more substituents selected from the group consisting of hydroxyl and —COOCH₃.

8. The compound according to claim 1, wherein:
R¹ is hydrogen;
R² is hydrogen;
R³ is hydrogen;
X is —N(R⁴)C(O)R⁵;
R⁴ is hydrogen;
Y is hydrogen, —C(O)—N═S(O)R⁷R⁶, —COOR⁹, —C(O)NHR¹⁰, —B(OH)₂, or

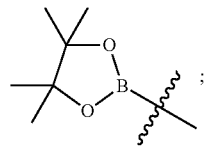

R⁷ is C₁₋₈ alkyl optionally substituted with one or more substituents selected from the group consisting of hydroxyl and —COOCH₃;
R⁶ is C₁₋₈ alkyl optionally substituted with one or more substituents selected from the group consisting of hydroxyl and —COOCH₃; and
R¹⁰ is hydrogen or C₁₋₈ alkyl optionally substituted with one or more substituents selected from the group consisting —COOCH₃.

9. The compound according to claim 1, wherein:
R¹ is hydrogen;
R² is hydrogen;
R³ is hydrogen;
X is —N(R⁴)C(O)R⁵;

R⁴ is hydrogen;
Y is hydrogen, —C(O)—N=S(O)R⁷R⁶, —COOR⁹, —C(O)NHR¹⁰, —B(OH)₂, or

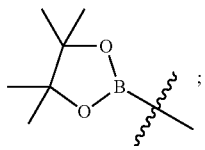 [SMILES: *B1OC(C)(C)C(C)(C)O1]

R⁷ is $C_{1-8}$ alkyl optionally substituted with one or more substituents selected from the group consisting of hydroxyl and —COOCH₃;
R⁶ is $C_{1-8}$ alkyl optionally substituted with one or more substituents selected from the group consisting of hydroxyl and —COOCH₃;
R⁹ is hydrogen or $C_{1-8}$ alkyl; and
R¹⁰ is hydrogen or $C_{1-8}$ alkyl optionally substituted with one or more substituents selected from the group consisting —COOCH₃.

10. The compound according to claim 1, wherein:
R¹ is hydrogen;
R² is hydrogen;
R³ is hydrogen;
X is —C(O)N(R⁴R⁵);
R⁴ is hydrogen;
Y is —COOR⁹; and
R⁹ is hydrogen or $C_{1-8}$ alkyl.

11. The compound according to claim 1, wherein:
R¹ is hydrogen;
R² is hydrogen;
R³ is hydrogen;
X is —N(R⁴)C(O)N(R⁴R⁵);
R⁴ is hydrogen;
Y is —C(O)NHR¹⁰; and
R¹⁰ is hydrogen or $C_{1-8}$ alkyl optionally substituted with one or more substituents selected from the group consisting —COOCH₃.

12. The compound according to claim 1, wherein:
R¹ is hydrogen;
R² is hydrogen;
R³ is hydrogen;
X is —N(R⁴)C(O)N(R⁴R⁵);
R⁴ is hydrogen; and
Y is

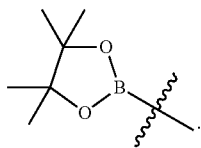 [SMILES: *B1OC(C)(C)C(C)(C)O1]

13. The compound according to claim 1, wherein:
R¹ is hydrogen;
R² is hydrogen;
R³ is hydrogen;
X is —N(R⁴)C(O)N(R⁴R⁵);
R⁴ is hydrogen; and
Y is —B(OH)₂.

14. The compound according to claim 1, wherein:
R¹ is hydrogen;
R² is hydrogen;
R³ is hydrogen;

X is —N(R⁴)C(O)R⁵;
R⁴ is hydrogen; and
Y is hydrogen.

15. The compound according to claim 1, wherein:
R¹ is hydrogen;
R² is hydrogen;
R³ is hydrogen;
X is —C(O)N(R⁴R⁵); and
Y is hydrogen.

16. A compound according to claim 1, selected from:
6-amino-N-[dimethyl(oxido)-λ⁴-sulfanylidene]-5-[5-({[(3-methylphenyl)amino]carbonyl}amino)-1-benzothien-2-yl]nicotinamide;
6-amino-5-[5-({[(3-chloro-4-fluorophenyl)amino]carbonyl}amino)-1-benzothien-2-yl]-N-[dimethyl(oxido)-λ⁴-sulfanylidene]nicotinamide;
6-amino-N-[dimethyl(oxido)-λ⁴-sulfanylidene]-5-[5-({[(2-fluoro-5-methylphenyl)amino]carbonyl}amino)-1-benzothien-2-yl]nicotinamide;
6-amino-5-{5-[(anilinocarbonyl)amino]-1-benzothien-2-yl}-N-[dimethyl(oxido)-λ⁴-sulfanylidene]nicotinamide;
6-amino-5-{5-[({[4-chloro-3-(trifluoromethyl)phenyl]amino}carbonyl)amino]-1-benzothien-2-yl}-N-[dimethyl(oxido)-λ⁴-sulfanylidene]nicotinamide;
6-amino-N-[dimethyl(oxido)-λ⁴-sulfanylidene]-5-{5-[({[2-fluoro-5-(trifluoromethyl)phenyl]amino}carbonyl)amino]-1-benzothien-2-yl}nicotinamide;
methyl 6-amino-5-{5-[({[3-(trifluoromethyl)phenyl]amino}carbonyl)amino]-1-benzothien-2-yl}nicotinate;
methyl 6-amino-5-{5-[({[2-fluoro-5-(trifluoromethyl)phenyl]amino}carbonyl)amino]-1-benzothien-2-yl}nicotinate;
methyl 6-amino-5-{5-[({[4-chloro-3-(trifluoromethyl)phenyl]amino}carbonyl)amino]-1-benzothien-2-yl}nicotinate;
methyl 6-amino-5-[5-({[(2-fluoro-5-methylphenyl)amino]carbonyl}amino)-1-benzothien-2-yl]nicotinate;
methyl 6-amino-5-[5-({[(3-methylphenyl)amino]carbonyl}amino)-1-benzothien-2-yl]nicotinate;
methyl 6-amino-5-[5-({[(3-chloro-4-fluorophenyl)amino]carbonyl}amino)-1-benzothien-2-yl]nicotinate;
methyl 6-amino-5-[5-({[(4-methylphenyl)amino]carbonyl}amino)-1-benzothien-2-yl]nicotinate;
methyl 6-amino-5-[5-({[(2-fluorophenyl)amino]carbonyl}amino)-1-benzothien-2-yl]nicotinate;
methyl 6-amino-5-{5-[(anilinocarbonyl)amino]-1-benzothien-2-yl}nicotinate;
methyl 6-amino-5-[5-({[(2,4-difluorophenyl)amino]carbonyl}amino)-1-benzothien-2-yl]nicotinate;
6-amino-5-[5-({[(3-chloro-4-fluorophenyl)amino]carbonyl}amino)-1-benzothien-2-yl]nicotinic acid;
6-amino-5-[5-({[(2-fluoro-5-methylphenyl)amino]carbonyl}amino)-1-benzothien-2-yl]nicotinic acid;
6-amino-5-[5-({[(3-methylphenyl)amino]carbonyl}amino)-1-benzothien-2-yl]nicotinic acid;
6-amino-5-[5-({[(3-methylphenyl)amino]carbonyl}amino)-1-benzothien-2-yl]nicotinamide;
methyl 4-[({6-amino-5-[5-({[(3-methylphenyl)amino]carbonyl}amino)-1-benzothien-2-yl]pyridin-3-yl}carbonyl)amino]butanoate;
methyl 6-[({6-amino-5-[5-({[(3-methylphenyl)amino]carbonyl}amino)-1-benzothien-2-yl]pyridin-3-yl}carbonyl)amino]hexanoate;
1-{2-[2-amino-5-(4,4,5,5-tetramethyl-1,3,2-dioxaborolan-2-yl)pyridin-3-yl]-1-benzothien-5-yl}-3-[2-fluoro-5-(trifluoromethyl)phenyl]urea;

1-{2-[2-amino-5-(4,4,5,5-tetramethyl-1,3,2-dioxaborolan-2-yl)pyridin-3-yl]-1-benzothien-5-yl}-3-[3-(trifluoromethyl)phenyl]urea;
1-{2-[2-amino-5-(4,4,5,5-tetramethyl-1,3,2-dioxaborolan-2-yl)pyridin-3-yl]-1-benzothien-5-yl}-3-[4-chloro-3-(trifluoromethyl)phenyl]urea;
1-{2-[2-amino-5-(4,4,5,5-tetramethyl-1,3,2-dioxaborolan-2-yl)pyridin-3-yl]-1-benzothien-5-yl}-3-(2-fluoro-5-methylphenyl)urea;
1-{2-[2-amino-5-(4,4,5,5-tetramethyl-1,3,2-dioxaborolan-2-yl)pyridin-3-yl]-1-benzothien-5-yl}-3-(3-chloro-4-fluorophenyl)urea;
1-{2-[2-amino-5-(4,4,5,5-tetramethyl-1,3,2-dioxaborolan-2-yl)pyridin-3-yl]-1-benzothien-5-yl}-3-(3-ethylphenyl)urea;
1-{2-[2-amino-5-(4,4,5,5-tetramethyl-1,3,2-dioxaborolan-2-yl)pyridin-3-yl]-1-benzothien-5-yl}-3-(3-methylphenyl)urea;
1-{2-[2-amino-5-(4,4,5,5-tetramethyl-1,3,2-dioxaborolan-2-yl)pyridin-3-yl]-1-benzothien-5-yl}-3-phenylurea;
{6-amino-5-[5-({[(3-methylphenyl)amino]carbonyl}amino)-1-benzothien-2-yl]pyridin-3-yl}boronic acid;
(6-amino-5-{5-[(anilinocarbonyl)amino]-1-benzothien-2-yl}pyridin-3-yl)boronic acid;
6-amino-5-(5-{[4-chloro-3-(trifluoromethyl)benzoyl]amino}-1-benzothien-2-yl)-N-[dimethyl(oxido)-$\lambda^4$-sulfanylidene]nicotinamide;
6-amino-N-[dimethyl(oxido)-$\lambda^4$-sulfanylidene]-5-{5-[(2-fluoro-5-methylbenzoyl)amino]-1-benzothien-2-yl}nicotinamide;
6-amino-5-[5-(benzoylamino)-1-benzothien-2-yl]-N-[dimethyl(oxido)-$\lambda^4$-sulfanylidene]nicotinamide;
6-amino-N-[dimethyl(oxido)-$\lambda^4$-sulfanylidene]-5-{5-[(3-methylbenzoyl)amino]-1-benzothien-2-yl}nicotinamide;
6-amino-N-[dimethyl(oxido)-$\lambda^4$-sulfanylidene]-5-(5-{[2-fluoro-5-(trifluoromethyl)benzoyl]amino}-1-benzothien-2-yl)nicotinamide;
methyl 6-amino-5-{5-[(3-methylbenzoyl)amino]-1-benzothien-2-yl}nicotinate;
methyl 6-amino-5-{5-[(2-fluoro-5-methylbenzoyl)amino]-1-benzothien-2-yl}nicotinate;
methyl 6-amino-5-[5-(benzoylamino)-1-benzothien-2-yl]nicotinate;
methyl 6-amino-5-{5-[(3-chloro-4-fluorobenzoyl)amino]-1-benzothien-2-yl}nicotinate;
methyl 6-amino-5-(5-{[2-fluoro-5-(trifluoromethyl)benzoyl]amino}-1-benzothien-2-yl)nicotinate;
N-[2-(2-aminopyridin-3-yl)-1-benzothien-5-yl]-3-methylbenzamide;
N-[2-(2-aminopyridin-3-yl)-1-benzothien-5-yl]benzamide;
2-(2-aminopyridin-3-yl)-N-(3-methylphenyl)-1-benzothiophene-5-carboxamide;
2-(2-aminopyridin-3-yl)-N-(2-fluoro-5-methylphenyl)-1-benzothiophene-5-carboxamide;
2-(2-aminopyridin-3-yl)-N-(3-chloro-4-fluorophenyl)-1-benzothiophene-5-carboxamide;
methyl 5-[N-({6-amino-5-[5-({[(3-methylphenyl)amino]carbonyl}amino)-1-benzothien-2-yl]pyridin-3-yl}carbonyl)-S-methylsulfonimidoyl]pentanoate;
methyl 5-[N-({6-amino-5-[5-({[(2-fluoro-5-methylphenyl)amino]carbonyl}amino)-1-benzothien-2-yl]pyridin-3-yl}carbonyl)-S-methylsulfonimidoyl]pentanoate;
methyl 5-[N-({6-amino-5-[5-({[(3-chloro-4-fluorophenyl)amino]carbonyl}amino)-1-benzothien-2-yl]pyridin-3-yl}carbonyl)-S-methylsulfonimidoyl]pentanoate; and
6-amino-N-[bis(3-hydroxypropyl)(oxido)-$\lambda^4$-sulfanylidene]-5-[5-({[(3-methylphenyl)amino]carbonyl}amino)-1-benzothien-2-yl]nicotinamide.

17. A pharmaceutical composition comprising as active ingredient a therapeutically effective amount of a compound according to claim 1 and a pharmaceutically acceptable adjuvant, diluent or carrier.

18. A compound selected from:
N-[dimethyl(oxido)-$\lambda^4$-sulfanylidene]-5-{5-[({[2-fluoro-5-(trifluoromethyl)phenyl]amino}carbonyl)amino]-1-benzothien-2-yl}nicotinamide; and
5-{5-[({[4-chloro-3-(trifluoromethyl)phenyl]amino}carbonyl)amino]-1-benzothien-2-yl}-N-[dimethyl(oxido)-$\lambda^4$-sulfanylidene]nicotinamide.

* * * * *